(12) United States Patent
Rosenblum

(10) Patent No.: US 7,774,097 B2
(45) Date of Patent: Aug. 10, 2010

(54) AUTOMATIC PRESCRIPTION DRUG DISPENSER

(75) Inventor: Ken Rosenblum, Mendota Heights, MN (US)

(73) Assignee: InstyMeds Corporation, Eden Prairie, MN (US)

( * ) Notice: Subject to any disclaimer, the term of this patent is extended or adjusted under 35 U.S.C. 154(b) by 0 days.

(21) Appl. No.: 12/258,822

(22) Filed: Oct. 27, 2008

(65) Prior Publication Data

US 2009/0048712 A1 Feb. 19, 2009

Related U.S. Application Data

(60) Continuation of application No. 11/821,004, filed on Jun. 21, 2007, now Pat. No. 7,444,203, which is a division of application No. 10/852,010, filed on May 24, 2004, now Pat. No. 7,471,993, which is a division of application No. 10/229,923, filed on Aug. 27, 2002, now Pat. No. 6,892,941.

(51) Int. Cl.
*G06F 17/00* (2006.01)

(52) U.S. Cl. ............... 700/236; 700/244; 700/242

(58) Field of Classification Search ......... 700/236, 700/244
See application file for complete search history.

(56) References Cited

U.S. PATENT DOCUMENTS

| | | | |
|---|---|---|---|
| 4,567,358 A | 1/1986 | Takamatsu et al. | |
| 4,732,411 A | 3/1988 | Siegel | |
| 4,891,502 A | 1/1990 | Motoi et al. | |
| 4,918,604 A | 4/1990 | Baum | |
| 5,348,061 A | 9/1994 | Riley et al. | |
| 5,385,265 A | 1/1995 | Schlamp | |
| 5,480,062 A * | 1/1996 | Rogers et al. | ............... 221/174 |
| 5,597,995 A | 1/1997 | Williams et al. | |
| 5,713,485 A | 2/1998 | Liff et al. | |

(Continued)

FOREIGN PATENT DOCUMENTS

EP 0764314 B1 9/1999

(Continued)

*Primary Examiner*—Gene Crawford
*Assistant Examiner*—Timothy R Waggoner
(74) *Attorney, Agent, or Firm*—Schwegman, Lundberg & Woessner, P.A.

(57) ABSTRACT

An automatic prescription drug dispenser including a remote dispenser, a prescription entry system, and a communications network. The remote dispenser transmits and receives information from the communications network and dispenses prescription drugs to the patient. The prescription entry system transmits and receives information from the communications network and provides an input system for the prescriber to electronically enter individual prescriptions for each patient. The communications network coordinates communications between the doctor, insurance carrier, and the remote dispenser. The remote dispenser stores, retrieves, and labels prescription drug and over-the-counter products directly to patients through a remote automated dispenser, a prescription entry system, and a communications network. The remote dispenser transmits and receives information from the communications network and dispenses drugs to the patient. The prescription entry system transmits and receives information from the communications network and provides an input system for the doctor to electronically enter individual prescriptions for each patient. The communications network coordinates communications between the prescriber, insurance carrier, and the remote dispenser. Also described are various embodiments of apparatus and method of the invention useful in pharmacy settings as for example found in drug stores or "big box" retailers or other such settings. Other methods include providing a remote dispenser in virtually any location.

13 Claims, 56 Drawing Sheets

U.S. PATENT DOCUMENTS

| | | | |
|---|---|---|---|
| 5,720,154 A | 2/1998 | Lasher et al. | |
| 5,758,095 A | 5/1998 | Albaum et al. | |
| 5,797,515 A | 8/1998 | Liff et al. | |
| 5,812,410 A | 9/1998 | Lion et al. | |
| 5,838,575 A | 11/1998 | Lion | |
| 5,883,370 A | 3/1999 | Walker et al. | |
| 5,883,806 A * | 3/1999 | Meador et al. | 700/244 |
| 5,907,493 A | 5/1999 | Boyer et al. | |
| 5,930,145 A | 7/1999 | Yuyama et al. | |
| 5,945,651 A | 8/1999 | Chorosinski et al. | |
| 5,963,453 A | 10/1999 | East | |
| 6,006,946 A | 12/1999 | Williams et al. | |
| 6,036,812 A | 3/2000 | Williams et al. | |
| 6,039,251 A | 3/2000 | Holowko et al. | |
| 6,068,156 A | 5/2000 | Liff et al. | |
| 6,125,844 A | 10/2000 | Samiotes | |
| 6,152,364 A | 11/2000 | Schoonen et al. | |
| 6,181,979 B1 | 1/2001 | Murakami | |
| 6,202,923 B1 | 3/2001 | Boyer et al. | |
| 6,219,587 B1 | 4/2001 | Ahlin et al. | |
| 6,230,927 B1 | 5/2001 | Schoonen et al. | |
| 6,249,717 B1 | 6/2001 | Nicholson et al. | |
| 6,283,322 B1 | 9/2001 | Liff et al. | |
| 6,305,377 B1 | 10/2001 | Portwood et al. | |
| 6,311,163 B1 | 10/2001 | Sheehan et al. | |
| 6,330,491 B1 | 12/2001 | Lion | |
| 6,335,907 B1 | 1/2002 | Momich et al. | |
| 6,352,200 B1 | 3/2002 | Schoonen et al. | |
| 6,361,263 B1 * | 3/2002 | Dewey et al. | 414/331.05 |
| 6,370,841 B1 | 4/2002 | Chudy et al. | |
| RE37,829 E | 9/2002 | Charhut et al. | |
| 6,464,142 B1 | 10/2002 | Denenberg et al. | |
| 6,471,089 B2 | 10/2002 | Liff et al. | |
| 6,493,427 B1 | 12/2002 | Kobylevsky et al. | |
| 6,529,801 B1 | 3/2003 | Rosenblum | |
| 6,564,121 B1 | 5/2003 | Wallace et al. | |
| 6,588,548 B1 | 7/2003 | Dewitt | |
| 6,604,019 B2 * | 8/2003 | Ahlin et al. | 700/231 |
| 6,697,704 B2 | 2/2004 | Rosenblum | |
| 6,766,218 B2 | 7/2004 | Rosenblum | |
| 6,883,681 B1 | 4/2005 | Coughlin et al. | |
| 6,892,941 B2 | 5/2005 | Rosenblum | |
| 7,006,893 B2 | 2/2006 | Hart et al. | |
| 7,093,755 B2 | 8/2006 | Jordan et al. | |
| 7,444,203 B2 | 10/2008 | Rosenblum | |
| 7,469,820 B2 | 12/2008 | Rosenblum | |
| 7,471,993 B2 | 12/2008 | Rosenblum | |
| 7,547,155 B2 * | 6/2009 | Windorski | 401/195 |
| 2004/0164146 A1 | 8/2004 | Rosenblum | |
| 2005/0021175 A1 | 1/2005 | Bain | |
| 2005/0049746 A1 | 3/2005 | Rosenblum | |
| 2007/0293982 A1 | 12/2007 | Rosenblum | |

FOREIGN PATENT DOCUMENTS

| | | |
|---|---|---|
| NL | 0942206 | 1/1996 |

* cited by examiner

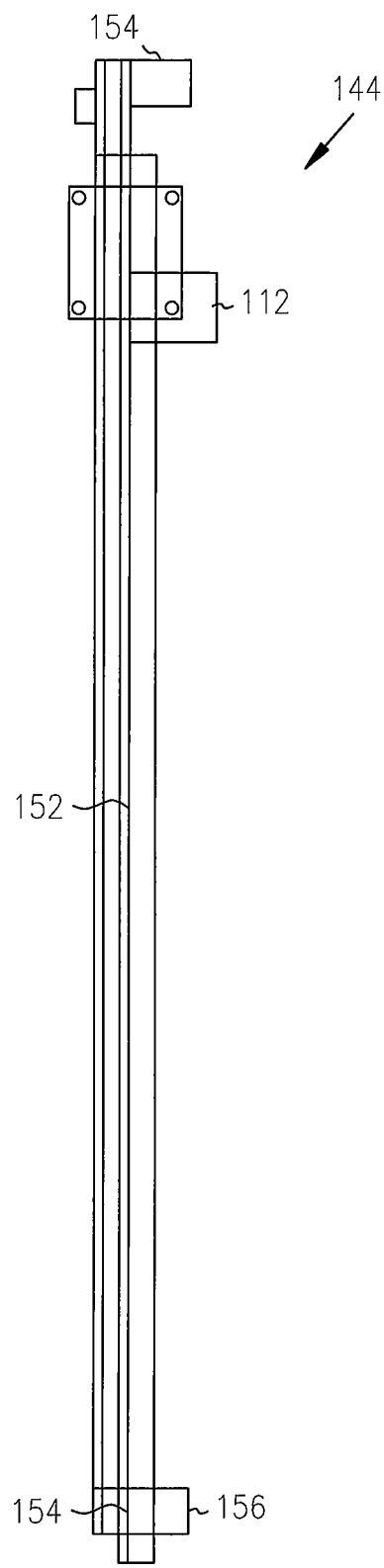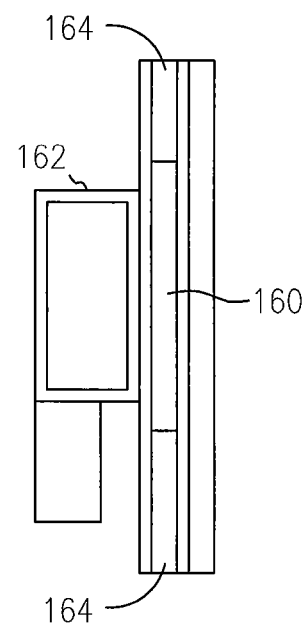
FIG. 16
FIG. 17

NEW PRESCRIPTION – FIND DRUG

- CHOOSE WHETHER TO DISPLAY PERSONAL MEDS LIST OR ALL MEDS. DEFAULT IS "MY MEDS". WHICHEVER YOU CHOOSE WILL BECOME THE DEFAULT FOR FUTURE PRESCRIPTIONS.
- SCROLL UP OR DOWN TO THE 1ST LETTERS OF THE MEDICATION AND PRESS ENTER. IF IN "ALL MEDS" MODE, SCROLL UP OR DOWN THE NEXT LIST TO PICK THE 1ST FOUR LETTERS OF THE MEDICATION AND PRESS ENTER. THE LIST COMPRISES BOTH BRAND AND GENERIC DRUG NAMES.

CHILDREN'S WEST   AUG. 12, 99
DR. S. KILEY              12:00 PM
NEW \ DONE \ REJECTED \ UTILITIES
AB   JONATHAN PATIENTOWRITZ
CD
EF
GH
IJK
LM                        ~4300
NO
PQR   MY MEDS
ST    ALL MEDS
UV
WXYZ

TAB BETWEEN SCREENS     CANCEL
GO BACK   SCROLL UP   ENTER AND MOVE
ONE FIELD   AND DOWN   TO NEXT FIELD

FIG. 23C

NEW PRESCRIPTION – CHOOSE DRUG

- SCROLL DOWN AND PRESS ENTER TO SELECT A MEDICATION.
- AT THE BOTTOM OF THE SCREEN, SCROLLING BEGINS 1 SCREEN AT A TIME.
- AT THE FIRST CHANGE OF DIRECTION, SCROLLING WILL OCCUR 1 RECORD AT A TIME.
- WHEN YOU REACH THE TOP OR BOTTOM OF SCREEN, SCROLLING WILL AGAIN OCCUR 1 SCREEN AT A TIME.
- THE LETTER 'D' AT THE END OF THE LINE SIGNIFIES THAT THE DRUG IS IN THE MEDIVENDOR
- IF THE DRUG IS CHOSEN FROM THE EXTENSIVE "ALL MEDS" LIST IN FROM THE PDR, YOU WILL BE ASKED IF YOU WISH TO MOVE THIS DRUG TO YOUR MUCH SHORTER "MY MEDS" LIST.
- IF THE DRUG HAS MORE THAN ONE DOSAGE FORM OR STRENGTH, A LIST OF DOSAGES AND STRENGTHS WILL APPEAR TO PICK FROM.

CHILDREN'S WEST   AUG. 12, 99
DR. S. KILEY              12:00 PM
NEW \ DONE \ REJECTED \ UTILITIES
JONATHAN PATIENTOWRITZ

ALLLLLLLLLLLLLLLLL      D
ALLLLLLLLLLLLLLLL
ALLLLLLLLLLLLLLLL
ALLLLLLLLLLLLLLLL       D     ~4300
ALLLLLLLLLLLLLLLL       D
ALLLLLLLLLLLLLLLL
ALLLLLLLLLLLLLLLL       D
ALLLLLLLLLLLLLLLL
ALLLL  XXXXXXXXXXX      D

TAB BETWEEN SCREENS     CANCEL
GO BACK   SCROLL UP   ENTER AND MOVE
ONE FIELD   AND DOWN   TO NEXT FIELD

FIG. 23D

NEW PRESCRIPTION – CHOOSE SIG

- SCROLL UP OR DOWN AND PRESS ENTER TO PICK A COMMON SIG.
- PRESS ENTER ON THE DOTTED LINE TO MANUALLY ENTER A SIG.
- WHEN YOU BEGIN USING THE SYSTEM, NOTICE THAT COMMON SIGS ARE PROVIDED FOR YOU. IF YOU CHOOSE TO MAKE UP YOU OWN SIG, IT WILL BE ADDED TO YOUR LIST FOR THIS MED EACH TIME YOU PRESCRIBE THIS MED IN THE FUTURE.
- THE CURSOR WILL FIRST APPEAR ON THE LAST SIG YOU WROTE FOR THIS MED.

CHILDREN'S WEST    AUG. 12, 99
DR. S. KILEY    12:00 PM
NEW \ DONE \ REJECTED \ UTILITIES

JONATHAN PATIENTOWRITZ
20 YO MALE 50 kg. (1 OF 1)
AMPICILLIN 250mg CAPS    (D)

TAKE ONE CAP OID X 70
TAKE TWO CAPS OID X 70
TAKE ONE CAP OID UNTIL GONE
TAKE TWO CAPS OID X 70
. . . . . . . . . . . .

~4300

TAB BETWEEN SCREENS | CANCEL
GO BACK ONE FIELD | SCROLL UP AND DOWN | ENTER AND MOVE TO NEXT FIELD

NEW PRESCRIPTION – CREATE SIG 1

- SCROLL UP OR DOWN AND PRESS ENTER
- PRESS ENTER ON THE DOTTED LINE TO SPELL OUT A WORD THAT DOESN'T APPEAR.
- ONLY THOSE WORDS APPLICABLE TO THIS MED WILL APPEAR.

CHILDREN'S WEST    AUG. 12, 99
DR. S. KILEY    12:00 PM
NEW \ DONE \ REJECTED \ UTILITIES

JONATHAN PATIENTOWRITZ
20 YO MALE 50 kg. (1 OF 1)
AMPICILLIN 250mg CAPS    (D)

TAKE
. . . . . .

~4300

TAB BETWEEN SCREENS | CANCEL
GO BACK ONE FIELD | SCROLL UP AND DOWN | ENTER AND MOVE TO NEXT FIELD

NEW PRESCRIPTION – CREATE SIG 2

CHILDREN'S WEST    AUG. 12, 99
DR. S. KILEY           12:00 PM
NEW \ DONE \ REJECTED \ UTILITIES

JONATHAN PATIENTOWRITZ
20 YO MALE 50 kg. (1 OF 1)
AMPICILLIN 250mg CAPS (D)

TAKE  1
      2
      ...                         ~4300

- SCROLL UP OR DOWN AND PRESS ENTER

- PRESS ENTER ON THE DOTTED LINE TO SPELL OUT A WORD THAT DOESN'T APPEAR.

- ONLY THOSE WORDS APPLICABLE TO THIS MED WILL APPEAR.

TAB BETWEEN SCREENS — CANCEL
GO BACK ONE FIELD | SCROLL UP AND DOWN | ENTER AND MOVE TO NEXT FIELD

FIG. 24C

NEW PRESCRIPTION – CREATE SIG 3

CHILDREN'S WEST    AUG. 12, 99
DR. S. KILEY           12:00 PM
NEW \ DONE \ REJECTED \ UTILITIES

JONATHAN PATIENTOWRITZ
20 YO MALE 50 kg. (1 OF 1)
AMPICILLIN 250mg CAPS (D)

TAKE  CAPSULE
      TABLET
      .......                     ~4300

- SCROLL UP OR DOWN AND PRESS ENTER

- PRESS ENTER ON THE DOTTED LINE TO SPELL OUT A WORD THAT DOESN'T APPEAR.

- ONLY THOSE WORDS APPLICABLE TO THIS MED WILL APPEAR.

TAB BETWEEN SCREENS — CANCEL
GO BACK ONE FIELD | SCROLL UP AND DOWN | ENTER AND MOVE TO NEXT FIELD

NEW PRESCRIPTION — CREATE SIG 6

- SCROLL UP OR DOWN AND PRESS ENTER

- PRESS ENTER ON THE DOTTED LINE TO SPELL OUT A WORD THAT DOESN'T APPEAR.

- ONLY THOSE WORDS APPLICABLE TO THIS MED WILL APPEAR.

```
CHILDREN'S WEST      AUG. 12, 99
DR. S. KILEY              12:00 PM
NEW \ DONE \ REJECTED \ UTILITIES

JONATHAN PATIENTOWRITZ
20 YO MALE 50 kg. (1 OF 1)
AMPICILLIN 250mg CAPS  (D)

TAKE 1 CAPSULE PO QID
........
UNTIL BOTTLE IS EMPTY
FOR 7 DAYS
FOR 10 DAYS
FOR 14 DAYS
```
~4300

TAB BETWEEN SCREENS — CANCEL
GO BACK ONE FIELD | SCROLL UP AND DOWN | ENTER AND MOVE TO NEXT FIELD

NEW PRESCRIPTION — ADD NEW SIG TO PERSONAL LIST?

- ENTER "YES" TO PLACE THIS NEW SIG ON YOUR "MY SIG" LIST.
  - WHEN A SIG ARE MANUALLY ENTERED SUCH AS THE ONE, IT WILL APPEAR ON YOUR PERSONALIZED "MY SIG" LIST FOR THIS MED. SIG INSTRUCTIONS CAN BE CONVENIENTLY PICKED FROM THE LIST WHENEVER YOU PRESCRIBE THIS DRUG. THE MOST RECENT SIG USED WILL APPEAR FIRST AND DEFAULT.
  - A MAXIMUM COMBINATION OF 5 PERSONAL OR STANDARD SIGS CAN BE ATTACHED TO EACH DRUG. IF AN ADDITIONAL SIG IS ENTERED. THE LAST SIG DROPS OFF FROM THE LIST.

```
CHILDREN'S WEST      AUG. 12, 99
DR. S. KILEY              12:00 PM
NEW \ DONE \ REJECTED \ UTILITIES

JONATHAN PATIENTOWRITZ
20 YO MALE 50 kg. (1 OF 1)
AMPICILLIN 250mg CAPS  (D)

TAKE 1 CAPSULE PO QID
WITH MEALS UNTIL BOTTLE IS
EMPTY.
```
~4300

TAB BETWEEN SCREENS — CANCEL
GO BACK ONE FIELD | SCROLL UP AND DOWN | ENTER AND MOVE TO NEXT FIELD

FIG. 25A

NEW PRESCRIPTION – CHOOSE # OF REFILLS AND DAW?

- SCROLL UP OR DOWN TO PICK THE NUMBER OF AUTHORIZED REFILL. THE DEFAULT IS ZERO
- SCROLL DOWN AND PRESS ENTER IF YOU WANT THE MEDICATION DAW (DISPENSED AS WRITTEN). THE DEFAULT IS "NO". IF DAW IS MARKED "YES", THE PRESCRIPTION LABEL WILL DISPLAY "DISPENSE AS WRITTEN".
- IF X REFILLS ARE AUTHORIZED AND THE MED IS DISPENSED FROM THE DISPENSER. A SCRIPT WILL ALSO PRINTOUT AUTHORIZING (X-1) REFILLS AND NOTING THAT AN ORIGINAL PRESCRIPTION WAS DISPENSED.

```
CHILDREN'S WEST    AUG. 12, 99
DR. S. KILEY            12:00 PM
NEW \ DONE \ REJECTED \ UTILITIES

JONATHAN PATIENTOWRITZ
20 YO MALE 50 kg. (1 OF 1)
AMPICILLIN 250mg CAPS   (D)

TAKE 1 CAPSULE PO OID
WITH MEALS UNTIL BOTTLE IS
EMPTY.

REFILLS [ 0 ]   DAW [ 11 ]
```
~4300

TAB BETWEEN SCREENS    CANCEL
GO BACK ONE FIELD    SCROLL UP AND DOWN    ENTER AND MOVE TO NEXT FIELD

FIG. 25B

NEW PRESCRIPTION – PICK QUANTITY

- SCROLL DOWN AND PRESS ENTER TO SELECT A COMMON QUANTITY. AT FIRST, THESE QUANTITIES WILL BE THOSE COMMONLY WRITTEN FOR THIS MED. A "D" AFTER THE NUMBER INDICATES THAT THIS QUANTITY IS IN THE DISPENSER.
- IF YOU ENTER A TIME PERIOD IN WHICH TO TAKE THE MEDICATION (I.E. 7 DAYS), THE SYSTEM WILL CALCULATE THE CORRECT QUANTITY TO DISPENSE. THE CURSOR WILL AT FIRST BE ON THE NEXT LARGER QUANTITY IN THE DISPENSER, IF ANY.
- IF YOU ENTER A NEW QUANTITY, IT WILL APPEAR ON YOUR COMMON QUANTITY LIST FOR THIS MED. YOU CAN CHOOSE UP TO 6 COMMON QUANTITIES IF ANOTHER QUANTITY IS CHOSEN, THE LAST QUANTITY DROPS OFF THE LIST.
- PRESS ENTER ON THE DOTTED LINE TO PICK A DIFFERENT QUANTITY.

```
CHILDREN'S WEST    AUG. 12, 99
DR. S. KILEY            12:00 PM
NEW \ DONE \ REJECTED \ UTILITIES
JONATHAN PATIENTOWRITZ
20 YO MALE 50 kg. (1 OF 1)
AMPICILLIN 250mg CAPS   (D)
QUANTITY:   21  D
            28  D
            20
            30
            40
            . . .
REFILLS [ 0 ]   DAW [ 11 ]
```
~4300

TAB BETWEEN SCREENS    CANCEL
GO BACK ONE FIELD    SCROLL UP AND DOWN    ENTER AND MOVE TO NEXT FIELD

FIG. 25C

NEW PRESCRIPTION – DIAL IN QUANTITY

- SCROLL UP OR DOWN TO CHANGE THE NUMBERS.
- SCROLL LEFT TO CHANGE A DIFFERENT DIGIT.
- PRESS ENTER WHEN FINISHED.

CHILDREN'S WEST     AUG. 12, 99
DR. S. KILEY                      12:00 PM
NEW \ DONE \ REJECTED \ UTILITIES

JONATHAN PATIENTOWRITZ
20 YO MALE 50 kg. (1 OF 1)
AMPICILLIN 250mg CAPS  (D)
QUANTITY: [ ][ ][2][8]

TAKE 1 CAPSULE PO QID
WITH MEALS UNTIL BOTTLE IS
EMPTY.

REFILLS [0]    DAW [11]

~4300

TAB BETWEEN SCREENS | GO BACK ONE FIELD | SCROLL UP AND DOWN | ENTER AND MOVE TO NEXT FIELD | CANCEL

NEW PRESCRIPTION – WRITE ANOTHER FOR THIS PATIENT?

- PRESS ENTER IF THIS IS THE LAST PRESCRIPTION FOR THIS PATIENT.
- SCROLL DOWN AND PRESS ENTER IF YOU WISH TO WRITE ANOTHER PRESCRIPTION FOR THIS PATIENT.

CHILDREN'S WEST     AUG. 12, 99
DR. S. KILEY                      12:00 PM
NEW \ DONE \ REJECTED \ UTILITIES

JONATHAN PATIENTOWRITZ
20 YO MALE 50 kg. (1 OF 1)
AMPICILLIN 250mg CAPS  (D)
QUANTITY: 28

SAVE AND WRITE ANOTHER FOR THIS PATIENT

SAVE AND FINISH

CANCEL

~4300

TAB BETWEEN SCREENS | GO BACK ONE FIELD | SCROLL UP AND DOWN | ENTER AND MOVE TO NEXT FIELD | CANCEL

FIG. 25E

DAILY DOSE---

DIAL MG/K/DAY DOSE... BY USING THE UP/DOWN BUTTON TO ADJUST THE DEFAULT DOSAGE. AS THE PER DAY DOSE IS ADJUSTED, EXACT DOSES, WHICH APPEAR IN THE 1ST COLUMN AFTER THE DRUG FORM/STRENGTH ARE AUTOMATICALLY CALCULATED. (PLEASE NOTE: THE VALUES ALWAYS ROUND UP--SO WHEN SELECTING A DAILY DOSE, SELECT AN EXACT MATCH OR A VALUE THAT IS SLIGHTLY LESS THAN THE DOSE YOU WANT.) PRESS ENTER.

```
INSTYMEDS        CREATE RX
XYZ CLINIC       MAR 21, 2002
GOODING, BILL MD    8:43 AM
         PEDIATRIC DOSAGE
AMOXICILLIN       (WT.=25LBS.)
44m/k/DAY      UNITS PER DAY

+ CAPSULE 250mg          1.99
  CAPSULE 500mg          0.99
  CHEW TAB 125mg         3.99
  CHEW TAB 250mg         1.99
```

FIG. 29A

ENTER WEIGHT---

DIAL.. IN THE PATIENT'S WEIGHT USING THE BACK, UP/DOWN, AND ENTER BUTTONS. EACH DIGIT IS DIALED IN SEPARATELY. PRESS ENTER TWICE WHEN FINISHED.

```
INSTYMEDS        CREATE RX
XYZ CLINIC       MAR 21, 2002
GOODING, BILL MD    8:42 AM
         ENTER WEIGHT
            25 LBS           →

AMPLICILLIN
ANALPRAM-HC
ANALPRAM-HC
```

FIG. 28F

FORM/STRENGTH---

SELECT FORM/STRENGTH... BY USING THE UP/DOWN BUTTON TO SELECT THE FORM/STRENGTH. PRESS ENTER.

EXCEEDING MAXIMUM DOSE... IF YOU SELECT A DOSE THAT EXCEEDS THE MAXIMUM RECOMMENDED DOSE/M/K/DAY YOU WILL BE PROMPTED TO ANSWER A QUESTION CONFIRMING YOUR INTEREST IN SELECTING THAT DOSE.

```
INSTYMEDS          CREATE RX
XYZ CLINIC         MAR 21, 2002
GOODING, BILL MD   8:44 AM
     PEDIATRIC DOSAGE
AMOXICILLIN    (WT.=25LBS.)
44m/k/DAY    UNITS PER DAY
+ CAPSULE 250mg            1.99
  CAPSULE 500mg            0.99
  CHEW TAB 125mg           3.99
  CHEW TAB 250mg           1.99
```

FIG. 29B

SELECT SIG... BY USING THE UP/DOWN BUTTON TO SELECT THE PRESCRIPTION INSTRUCTIONS. THE DOSE WILL HAVE BEEN CALCULATED BY DIVIDING THE DAILY DOSE BY THE FREQUENCY AND ROUNDING UP. PRESS ENTER

```
INSTYMEDS          CREATE RX
XYZ CLINIC         MAR 21, 2002
GOODING, BILL MD   8:44 AM
         SELECT SIG
JONES, JANE (WT.=25LBS.)
11M F(1OF1)
AMOXICILLIN CAPSULE 500mg

TAKE 0.5 cap PO BIDx10d
TAKE 0.5 cap PO TIDx10d
TAKE 0.5 cap PO TIDx7d
```

FIG. 29C

AUTOMATIC PRESCRIPTION DRUG DISPENSER

PRIORITY OF INVENTION

This application is a continuation application of U.S. application Ser. No. 11/821,004, filed Jun. 21, 2007 now U.S. Pat. No. 7,444,203, which is a divisional application of U.S. application Ser. No. 10/852,010, filed May 24, 2004 now U.S. Pat. No. 7,471,993, which is a divisional application of U.S. application Ser. No. 10/229,923, filed Aug. 27, 2002 now U.S. Pat. No. 6,892,941, which claims priority of invention under 35 U.S.C. §120 from U.S. application Ser. No. 09/714,802, filed Nov. 16, 2000, which is a nonprovisional application filed under 35 U.S.C. §119(e) of U.S. Provisional Application No. 60/210,303 filed Jun. 8, 2000, all of which are incorporated herein by reference in their entirety.

TECHNICAL FIELD

The present invention concerns dispensing systems, such as vending machines, particularly dispensing systems for prescription drugs.

BACKGROUND

U.S. application Ser. No. 09/714,802 describes a prescription medication dispensing machine capable of, among other things, automatically labelling a medication for dispensing to a specific patient in response to electronic prescription data supplied to the machine. This application presents various applications and improvements to the embodiments illustrated in U.S. Ser. No. 09/714,802. In particular, but not limited thereto, the present application describes applications and alternate embodiments of the apparatus particularly useful in pharmacy settings in drug stores or other establishments like "big box" retailers.

SUMMARY

The present discussion includes a number of different method and apparatus embodiments useful in, among other things, the dispensing of prescription medications at a pharmacy that may or may not be staffed with live pharmacy personnel during some or all of its operating hours.

BRIEF DESCRIPTION OF DRAWINGS

FIG. 16 is a front view of a y-axis system of the gantry transport system according to one embodiment of the present invention.

FIG. 17 is a cross sectional view of a y-axis system according to one embodiment of the present invention.

DETAILED DESCRIPTION OF PREFERRED EMBODIMENTS

The following detailed description, which references and incorporates the Figures, describes and illustrates one or more specific embodiments of the invention. These embodiments, offered not to limit but only to exemplify and teach the invention, are shown and described in sufficient detail to enable those skilled in the art to practice the invention. Thus, where appropriate to avoid obscuring the invention, the description may omit certain information known to those of skill in the art.

The automatic prescription dispensing system provides safe, convenient and immediate prescription drug service to patients in primary, urgent, acute, and emergency care settings. Further examples provide prescription drug service to patients in pharmacies, either with or without the intervention of a pharmacist. The system can be used in virtually any location, such as doctor's office, a kiosk in a mall, or a bus station, for example. The system can deliver prescribed medication, over-the-counter (OTC) medication, and medical supplies, such as syringes. Some embodiments can deliver virtually any dispensable or vendible product.

The system provides several advantages including, but not limited to, entry of a prescription into a handheld computer using a unique software application, downloading of prescription and patient data from a central server database, acceptance of credit, debit, smart and ATM cards, cash, or check. The system includes automatic verification by barcode of each drug package for correct drug and expiration date before dispensing, optional prescription print-out instead of dispensing the prescription drugs, dispensing of appropriate drug education information and payment receipts, transfer of information to and from a central server database regarding available product information, restocking, product returns, prescription-filled and prescription-printed flags, patient requests for automatic refills and refill reminders, failure information, the ability to alert the central server if security of the dispensing system is compromised, and other miscellaneous two-way information transfers between a patient and a central control via a touch screen or other interface.

System Architecture

Figure 1:
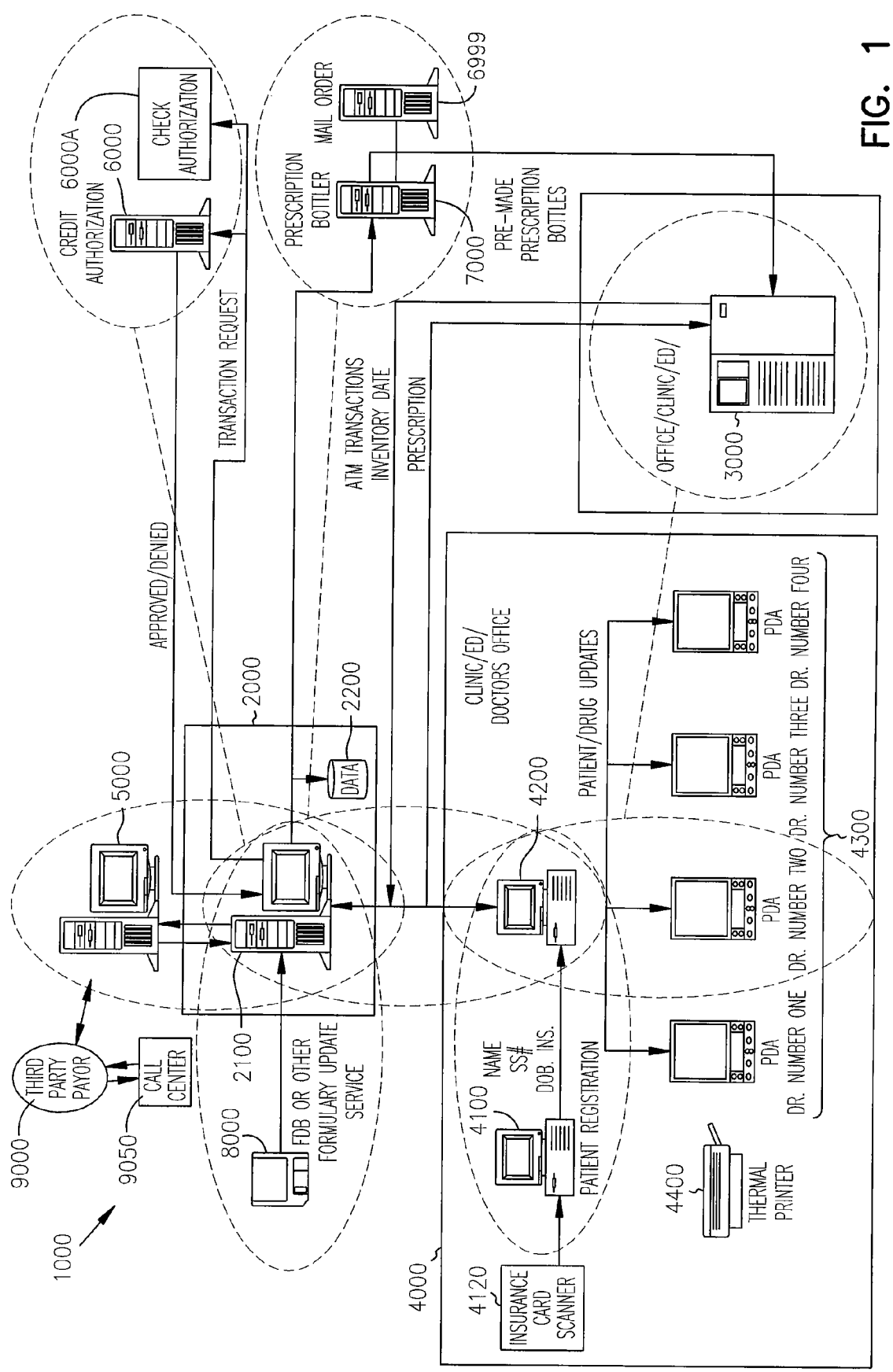
FIG. 1 is a schematic diagram of a high-level computer system architecture according to one embodiment.

FIG. 1 is a schematic diagram of a high-level computer system architecture embodiment of the invention. The system 1000 is a distributed network comprising a central server 2000, a remote dispenser 3000, and one or more prescription and patient data entry systems such as HCF system 4000. A patient who visits a physician or other provider at a healthcare facility (HCF), such as a clinic, where an HCF system 4000 (or other prescription entry system) is located receives a prescription that is filled at the remote dispenser 3000 if the prescription is so authorized, or adjudicated (if there is no insurance, the prescription need not be adjudicated), by central server 2000. To decide whether to authorize the prescription, central server 2000 is in distributed network communications with the adjudication system 5000, a payment authorization system 6000, such as a credit card authorization system, a check verification system 6000A, or other payment scheme, a mail order system 6999, a prescription bottler system 7000, and a drug formulary update service 8000. Here, adjudication system 5000 routes any insurance claims to third-party payors 9000 (TPP). If a claim is denied by the TPP, the rejected claim is routed to a call center 9050. The call center 9050 analyzes the rejection and views scanned insurance card images. After any corrections are made, the claim is resubmitted or the prescription is printed for the patient. The call center 9050 can also be in communication with the clinic and with a user via a phone or other communications means at remote dispenser 3000.

Central Server

Central server 2000 captures all data that is created by the various other components of the system 1000. It also prepares, sends, and receives all adjudicated claims; prepares, sends, and receives all credit card, cash, or check payments; and retains inventory data for all remote dispensers.

An example of the hardware and software that are suitable for the central server 2000 is a Compaq Prolient 1800 computer system 2100 that is expandable to dual processors, one gigabyte of SDRAM central memory, and 250 gigabytes of SCSI hard drive storage 2200; Microsoft Windows NT Server 4.0 operating system; and Microsoft SQL Server 7.0 database. Other generally equivalently performing hardware and software could be substituted in a known manner without limiting the scope of the invention. In accordance with known principles, the design of the system should be such that the system functions are not dependent upon the particular hardware or software selected for implementation, thus permitting the system to migrate to other hardware or software platforms without any change in the scope of the invention.

A software application running on the central server 2000 is responsible for setting up authorized HCF systems 4000 and prescribers of prescriptions. This application is preferably written in Java for display in an Internet browser application running on a client of the central server 2000 or a HCF system 4000 (assuming appropriate authorization criteria are met).

Another software application running on the central server 2000 is responsible for generating reports to document the operation and performance of system 1000 in accordance with well-known principles. Reports are preferably created on central server 2000 and sent to a printer anyplace on the network for generation of hard copy. A commercially available report generation system, preferably but not necessarily Crystal Reports, may be used to format the report data in accordance with well-known principles.

Another software application running on the central server 2000 is responsible for processing transactions associated with the adjudication of valid prescriptions (if necessary). A commercially available adjudication application, preferably but not necessarily Claims Engine 2000, may be used in accordance with well-known principles to exchange data between central server 2000 and adjudication system 5000.

Another software application running on the central server 2000 is responsible for packaging, sending and receiving credit card, cash, check, or other type payment and reversal transactions generated by patients who must pay for the prescriptions they receive. A commercially available but proprietary authorization application, provided by the credit card vendor(s), may be used in accordance with well-known principles to exchange data between central server 2000 and credit card authorization server 6000. In the same manner, check authorization can be performed using a system such as Telecheck, using a service such as electronic check acceptance (ECA).

Another software application running on the central server 2000 is responsible for monitoring the inventory levels of the various products dispensed from each of the remote dispensers 3000. In accordance with known principles, monitored inventory levels are used to determine reorder points (times and quantities) for the products. This application also determines which National Drug Code (NDC) is used to adjudicate the prescription when a particular product is prescribed. The application is preferably written in Java for display in an Internet browser application. The application will run both on the central server 2000 and on the HCF workstation 4200. Optionally, inventory levels are monitored by the remote dispenser 3000. The central server 2000 provides vendor and product information and the remote dispenser 3000 would interact with the vendors and perform the inventory control functions. Summary reports are uploaded to the central server 3000.

Another software application running on the central server 2000 is responsible for importing and maintaining the drug information. The preferred method is to import and maintain drug data files 8000 provided by First Databank (FDB), using an application written in Java and using the FDB toolkit provided by the vendor.

Another software application running on the central server 2000 is responsible for setting the price of products dispensed from remote dispenser 3000. The preferred embodiment is a program written in Java.

Remote Dispenser

Figure 2:
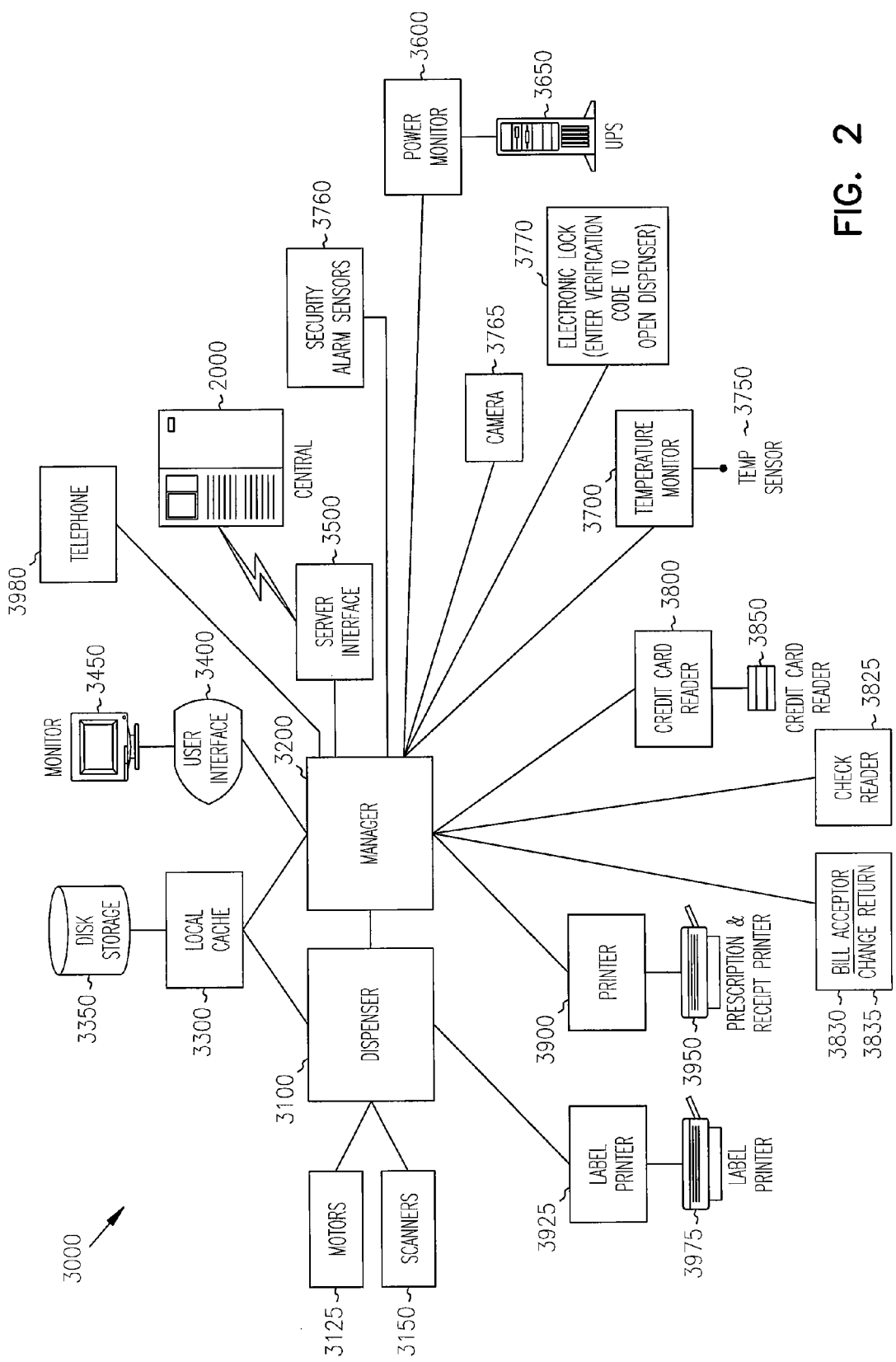
FIG. 2 is a schematic diagram of a software architecture embodiment of the remote dispenser according to one embodiment of the present invention.

FIG. 2 is a schematic diagram of the software architecture of the remote dispenser 3000. From a software standpoint, remote dispenser 3000 comprises two major subcomponents, dispenser module 3100 and manager module 3200, which communicate with each other in any well-known manner. Dispenser module 3100 controls the actual dispensing of the product from the remote dispenser 3000. Given properly verified data, dispenser module 3100 will dispense properly labeled product. To do so, it issues appropriate commands to motor 3125, scanner 3150 and label printer driver 3925 based on communications with manager module 3200 and local cache 3300.

Manager module 3200 is the main controller of remote dispenser 3000. It coordinates and controls the interaction between all of the other hardware and software components of the remote dispenser 3000. It communicates with dispenser module 3100, local cache 3300, user interface 3400, server interface 3500, power monitor 3600, temperature monitor 3700, cash handler or debit, ATM, smart, or credit card reader driver 3800, or a check reader 3825, or a cash acceptor 3830 and change return 3835, and prescription/receipt printer driver 3900.

Local cache 3300 is responsible for storing and retrieving data in local storage 3350. The local cache 3300 manages data related to product inventory, system configuration, and advertising. It communicates with dispenser module 3100 and manager module 3200 as required. Local storage 3350 is any appropriate data storage device performing typical data storage and handling in a well-known manner.

User interface 3400 is responsible for interacting with patients and maintenance personnel. It controls the screen display shown on visual monitor 3450, and also manages timeouts that can be encountered at each step of the process of using remote dispenser 3000.

Server interface 3500 is responsible for communications with the central server 2000. It will send and receive data between the remote dispenser 3000 and the central server 2000. It is also responsible for translating data to and from formats required by the remote dispenser 3000 and central server 2000.

Power monitor 3600 monitors the normal line voltage power supply to remote dispenser 3000 and activates uninterruptible power supply (UPS) 3650 as required.

Temperature monitor 3700 monitors the ambient temperature inside remote dispenser 3000 with a temperature sensor 3750.

Card reader driver 3800 allows manager module 3200 to operate a commercially available cash handler, ATM, smart debit or credit card reader 3850 in a well-known manner.

Check reader 3825 can be a check reader such as a check reader distributed by Magtek Inc. As discussed above, the check reader can be operatively coupled to central server 2000 to allow for check authorization to be performed using a system 6000A, such as Telecheck, using a service such as electronic check acceptance (ECA).

Prescription/receipt printer driver 3900 allows manager module 3200 to operate a prescription/receipt printer 3950 in a well-known manner.

Label printer driver 3925 allows dispenser module 3100 to operate a label printer 3975 in a well-known manner.

Some options include a security alarm sensors 3760, a camera 3765 to take a patient's picture or picture of an I.D., and an electronic lock system 3770. Camera 3765 can also be located within the remote dispenser to provide and internal view of the various mechanisms of the dispenser. Thus it can be used as a diagnostic tool to help maintain the dispenser.

One option includes a telephone 3980 on the dispenser to allow the user to speak with the central control and call center to discuss any insurance problems, for example. The telephone can also allow a remote pharmacist or other health care provider to ask or answer any questions by the user.

Manager

The manager module 3200 comprises various other software modules to support the following activities at the remote dispenser 3000.

Dispensing of Products

In one example, a patient who has a valid prescription voucher from a physician initiates the dispensing activity at visual monitor 3450. The patient inputs the voucher number, patient birth date (or other validation method), their selection of products (if any beyond those included in the prescription), and, if necessary, a check into check reader 3825, cash into cash acceptor 3830, or a credit, debit, ATM, or smart card number through use of card reader 3850. One option incorporates a "Bluetooth" or infrared enabled system within the dispenser which is in communication with a payment server, thus allowing a user to pay using a cell phone, or other Bluetooth (or infrared) enabled device. Manager module 3200 communicates with central server 2000 to authorize the entire transaction. Once authorized, manager module 3200 communicates with dispenser module 3100 to generate the dispensed medications; and with prescription/receipt printer driver 3900 to print appropriate information and receipts on prescription/receipt printer 3950. The system can also print up advertising, coupons, patient information, or other marketing information. The patient receives drug specific education advertising via a screen or printer while product is being received. The information can be tailored to be drug specific and/or patient specific. The patient can be asked if they would like additional information about their medication sent to them, such as reminders about refilling their prescriptions, or if they would like to be in a drug compliance program, for example. In addition, a toll free pharmacist helpline is offered via the interface or over telephone 3980. The interface can also provide marketing or educational information or questionnaires.

In other examples, which will be further discussed below, the patient (or patient's agent, such as a friend or family member) can insert a regular written prescription into the dispenser. The dispenser can image the prescription and transfer the image to a pharmacy services provider who can control the dispenser to deliver the medication or supplies.

Restocking of Products

An HCF staff person, for example, initiates the restocking activity. This person would typically be a local person at the HCF at which remote dispenser 3000 is located who has the proper security authorization. Restocking involves removing magazines that are empty or that have been selected for removal (e.g., expired or superceded products). Manager module 3200 tracks restocking activity and communicates appropriate data over server interface 3500 to central server 2000 so that proper inventory control is maintained. After each restocking, or after each time the door is opened, the system goes through each position within the dispenser to verify and update the location of each item in the dispenser. This means that the restocking person does not have to worry that they are putting the right product in the correct slots. Wherever they put it, the system will rescan each slot and update the position each product. Moreover, since the medication comes pre-filled and pre-checked in the magazines (from prescription bottler 7000, for example), the system provides a fool-proof, safe medication delivery paradigm.

Diagnostics

A maintenance person initiates the diagnostic activity. This person would typically be a dedicated maintenance person who travels from one remote dispenser 3000 to the next. Diagnostics include testing the availability and functionality of the hardware components of remote dispenser 3000. In addition to testing individual components, the entire dispensing activity can be tested by dispensing a placebo or other product.

The maintenance and diagnostic routines are preferably implemented by putting an invisible button on the voucher number entry screen portion of visual monitor 3450. For example, after entering a special password code for voucher number, and pressing the hidden button twice, the maintenance mode is entered if the special password code is otherwise valid. A selection of available options, depending on authorization level, is displayed: restocking of products, rescanning of product magazines to verify inventory; display of current inventory (including an option to print the result on prescription/receipt printer 3950); diagnostic routines; communication status (e.g., "pinging" other devices to ensure that communications links are active); dispensing a placebo product to display the status of the dispensing operation by exercising all devices including motors, scanners, and printers (the placebo product will be labeled to test label printer 3975); manual operation of available hardware (e.g., activating various motors, displaying scanned input from a test of input devices, and the like); confirmation of configuration for devices that are configurable (e.g., communications port parameters, logical addresses of each device); and, status of communications to central server 2000 (typically a multi-step routine in which first visual monitor 3450 displays the status of the connection to central server 2000, followed by an active pinging of central server 2000, followed by pinging of any router that may be between server interface 3500 and central server 2000, etc.).

Advertising and/or Educational Information

Visual monitor 3450 may display information such as educational information or advertisements during idle times and during certain stages of the dispensing activity. The educational information or advertisements may be in the form of images, animation, audiovisual works, etc. without limiting the scope of the invention.

Error Recovery

Manager module 3200 will attempt to recover from errors that are encountered during dispensing. Such errors include communication problems with the central server 2000, and hardware problems on the remote dispenser 3000. The central server 2000 will be appropriately notified of the errors.

Monitoring

Manager module 3200 notifies central server 2000 when appropriate boundary conditions are approached or exceeded. Such conditions include temperature, interruption to normal line voltage power supply, paper supply for each printer 3950 and 3975, physical access to remote dispenser 3000, and failed dispensing caused by mechanical or electrical failure, for example.

HCF System

Referring again to FIG. 1, each HCF system 4000 comprises a patient registration client 4100, a HCF workstation 4200, one or more computers 4300 (as an example only, FIG. 1 shows four such handheld computers 4300, computers 4300 can also be desktop or laptop computers), and one or more laser or thermal printers 4400. Registration client 4100 may be any suitably configured network capable personal computer or dedicated terminal in communication with HCF workstation 4200. HCF workstation 4200 may be any suitably configured network capable personal computer; the preferred configuration is a small form factor personal computer from Compaq, running Microsoft Windows NT Workstation 4.0. Computer(s) 4300 may be any suitably configured desktop or portable computer such as a laptop, palmtop, personal digital assistant, etc. The preferred model is a Palm Vx from Palm Computing, running Palm OS. Another example model is a PC having a web-based application. Printer 4400 is connected to the HCF system 4000 in a well-known manner and may be any suitably configured model of laser or thermal printer.

A software application for client registration runs on the HCF workstation 4200, and is written in a language pertinent to that platform, preferably Java for display in an Internet browser application running on the patient registration client 4100. One option includes an insurance card scanner 4120 to allow the HCF personnel to input an image of the insurance card into the system.

A software application for prescription writing runs on both the handheld computers 4300 and the HCF workstation 4200, and is written in languages pertinent to each platform. The software application processes the creation of prescriptions and vouchers that may be used to obtain prescriptions from the remote dispenser 3000; printing of prescriptions, vouchers, and adjudication results; and modifications to prescriptions and vouchers. The portion of the software that runs on the handheld computers 4300 is preferably an application for the Palm OS developed with the CodeWarrior development platform, but this is not a limitation on the scope of the invention. The portion of the software that runs on the HCF workstation 4200 is preferably a Java application for display in an Internet browser application running on the workstation 4200, but this also is not a limitation on the scope of the invention.

Each HCF system 4000 is connected to the central server 2000 through well-known networking techniques, such as a frame relay cloud or a virtual private network (VPN) or both. Other networking techniques include dial-up, ISDN, satellite uplink, etc.

Adjudication System

The adjudication system 5000 can communicate with third party payers 9000 through a "switch" company such as Envoy or NDC. A commercially available application, provided by the third party payor, may be used in accordance with well-known principles to exchange data between central server 2000 and adjudication system 5000.

Cash, Check, Credit, Debit, ATM, or Smart Card Authorization System

The card authorization system 6000 is under the control of a third-party credit card transaction clearing house. As noted above, custom written software is used to exchange data between central server 2000 and credit card authorization system 6000. Check authorization can be accomplished as discussed above.

Mail Order and Prescription Bottler Systems

The mail order system 6999 and the prescription bottler system 7000 can be under the control of a third-party distributor of products to be provided to remote dispenser 3000. A commercially available application, provided by the distributor, may be used in accordance with well-known principles to exchange data between central server 2000 and systems 6999 and/or 7000. Systems 6999 and 7000 can be FDA-approved repackaging systems to repackage unit doses from manufacturers into prescription size packages.

Drug Formulary System

As described above, the preferred method for importing and maintaining drug formulary files on the central server 2000 is to import and maintain drug formulary data files 8000 provided in any convenient format. Such files can be transferred and managed using any well-known data storage medium, or they may be transferred and managed using a direct network connection between central server 2000 and the publisher of the drug formulary data files.

Patient Visit and Prescription Process—Overview

Figure 3:
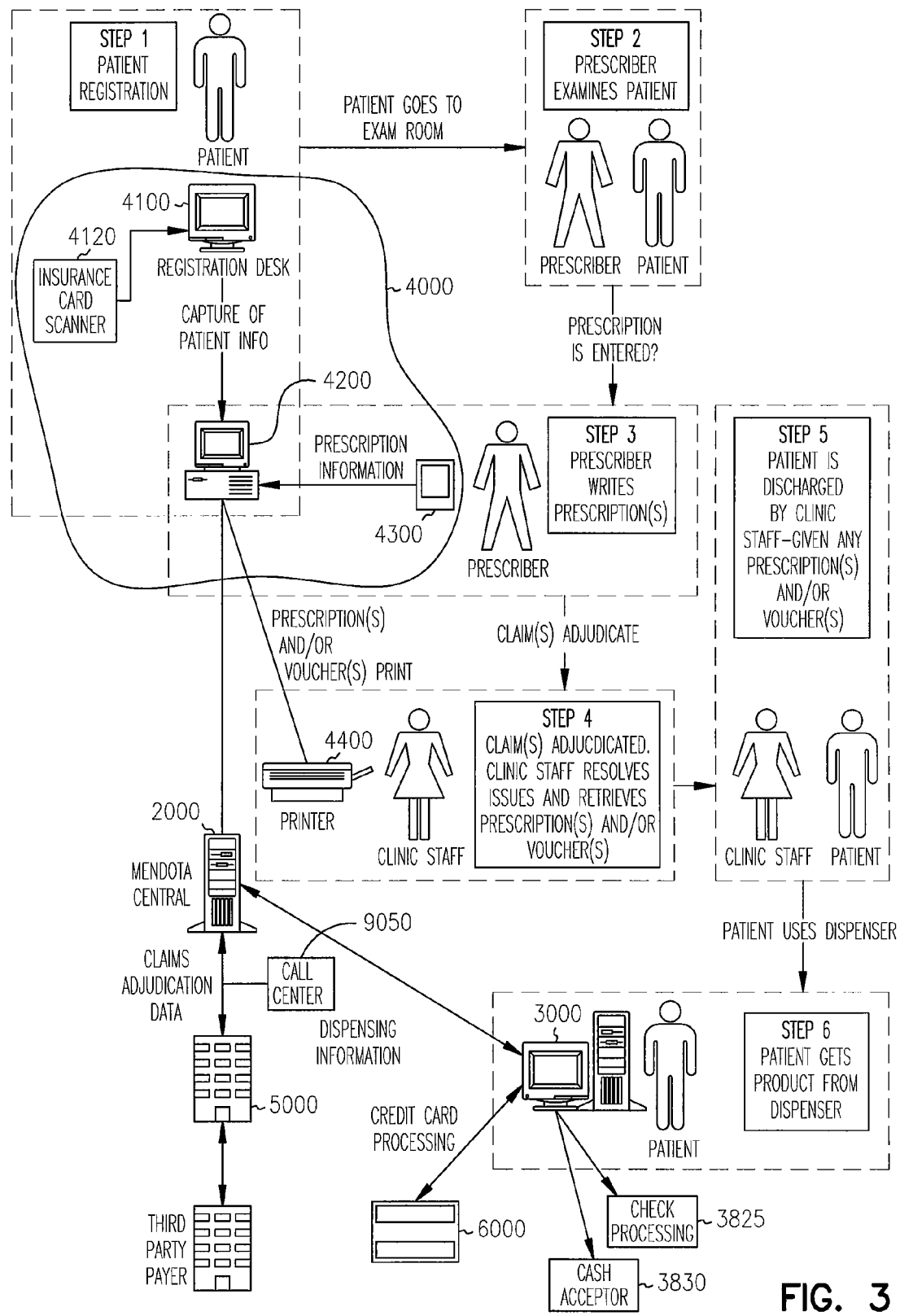
FIG. 3 is a schematic diagram of a process by which a patient is seen by a prescriber, receives a prescription, and has the prescription filled by the remote dispenser according to one embodiment of the present invention.

FIG. 3 illustrates the basic process by which a patient is seen by a prescriber, receives a prescription, and has that prescription filled by remote dispenser 3000. In the patient registration process, the patient presents himself or herself at a registration desk where patient registration client 4100 is located. Patient information is captured by patient registration client 4100 and transferred to HCF workstation 4200, or if the system omits workstation 4200, the information can be transferred directly to central server 2000 (See FIG. 1). If the patient has insurance, the insurance card can be scanned with scanner 4120. In the examination process, a prescriber (typically a physician) examines the patient and, depending on the outcome of the examination, may desire to prescribe a product for the patient. In the prescription writing process, the prescriber uses the computer 4300 to write a prescription by entering the prescription data into the handheld computer 4300 and transferring the data to the HCF workstation 4200. In one embodiment, the prescriber can bypass the handheld computer and directly enter the information into workstation 4200. Some embodiments of the present system omit computer 4300 and allow the prescriber to simply write out the prescription on a typical prescription pad, as will be discussed below. In another example, the prescriber can call the prescription in to the call center 9050. In another example the prescriber may have their own prescription entry system and they can enter it into that system and then upload the data to the central server.

In the adjudication process (if the patient has insurance), data representing the prescription and associated insurance information of the patient is sent by the HCF workstation 4200 to the central server 2000 for processing and subsequent transmission to the adjudication system 5000 under the control of a "switch" company that routes the prescription information to the proper third party payer. The adjudication system 5000 transmits data regarding the outcome of the adjudication to the central server 2000, which processes it accordingly and notifies the HCF system 4000 of the outcome. If necessary, the HCF staff can resolve any outstanding issues and retrieves the adjudicated prescription and/or voucher from printer 4400 of HCF system 4000. In one embodiment, rejections can be routed to call center 9050. The call center 9050 analyzes the rejection and views scanned insurance card images. After any corrections are made, the claim is resubmitted or the prescription is printed for the patient.

In the discharge process, the HCF staff transfers the prescription or voucher to the patient as part of terminating the examination process. In the prescription retrieval step, the patient uses a check, cash, a voucher or their card at the remote dispenser 3000 to have their prescription filled. This process involves the remote dispenser 3000 communicating with the central server 2000 for verification, inventory control, and other purposes. The remote dispenser 3000 can also be connected to call center 9050 to allow for any questions or problems to be resolved.

Patient Registration Process

Figure 4:
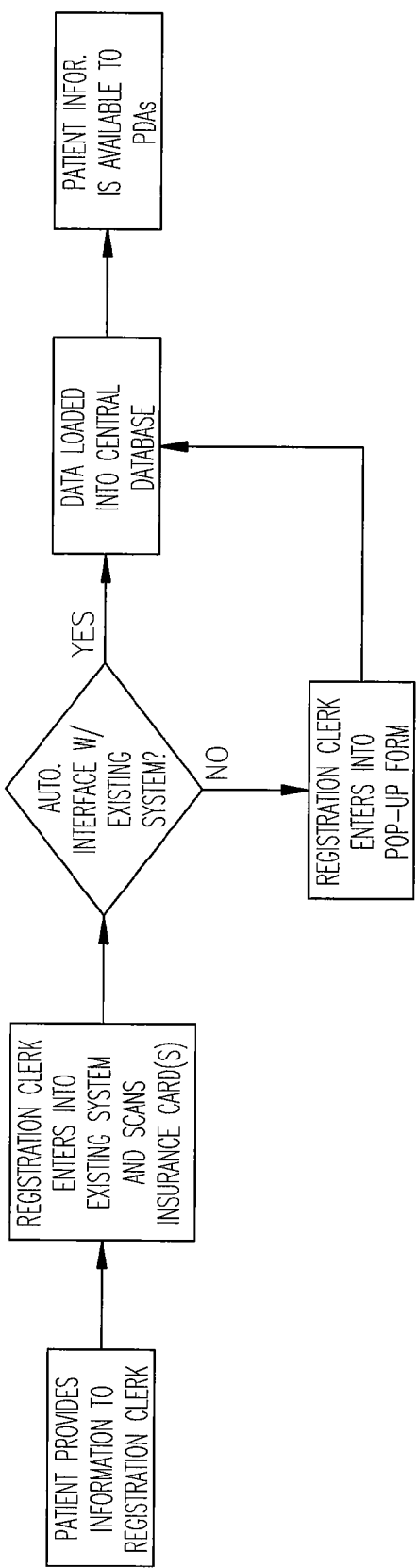
FIG. 4 is a schematic diagram of a patient registration process according to one embodiment of the present invention.

FIG. 4 illustrates the patient registration process in more detail. The patient provides basic information to the registration clerk or the information is retrieved from a patient database. Such data would typically include mandatory information (name, gender, date of birth, mailing address, and telephone number) and optional information (social security number; weight; known allergies; prescriber name; prescription benefit insurance company name, policy number, group number, member number, and relationship code). Either the patient registration client 4100 contains an automatic interface to an existing registration system, or an application that captures the necessary information for the first time, or the information is manually entered into the system or the information is faxed or scanned to a remote location for manual entry, or some combination of the above. In either case, the captured data is immediately transferred to HCF workstation 4200, central server 2000, and subsequently to the specific computer 4300 (handheld or desktop) in use by the specific prescriber assigned to the patient. Also, at this time, the patient's insurance card can be scanned into the system.

Prescription Writing Process

Figure 5A:
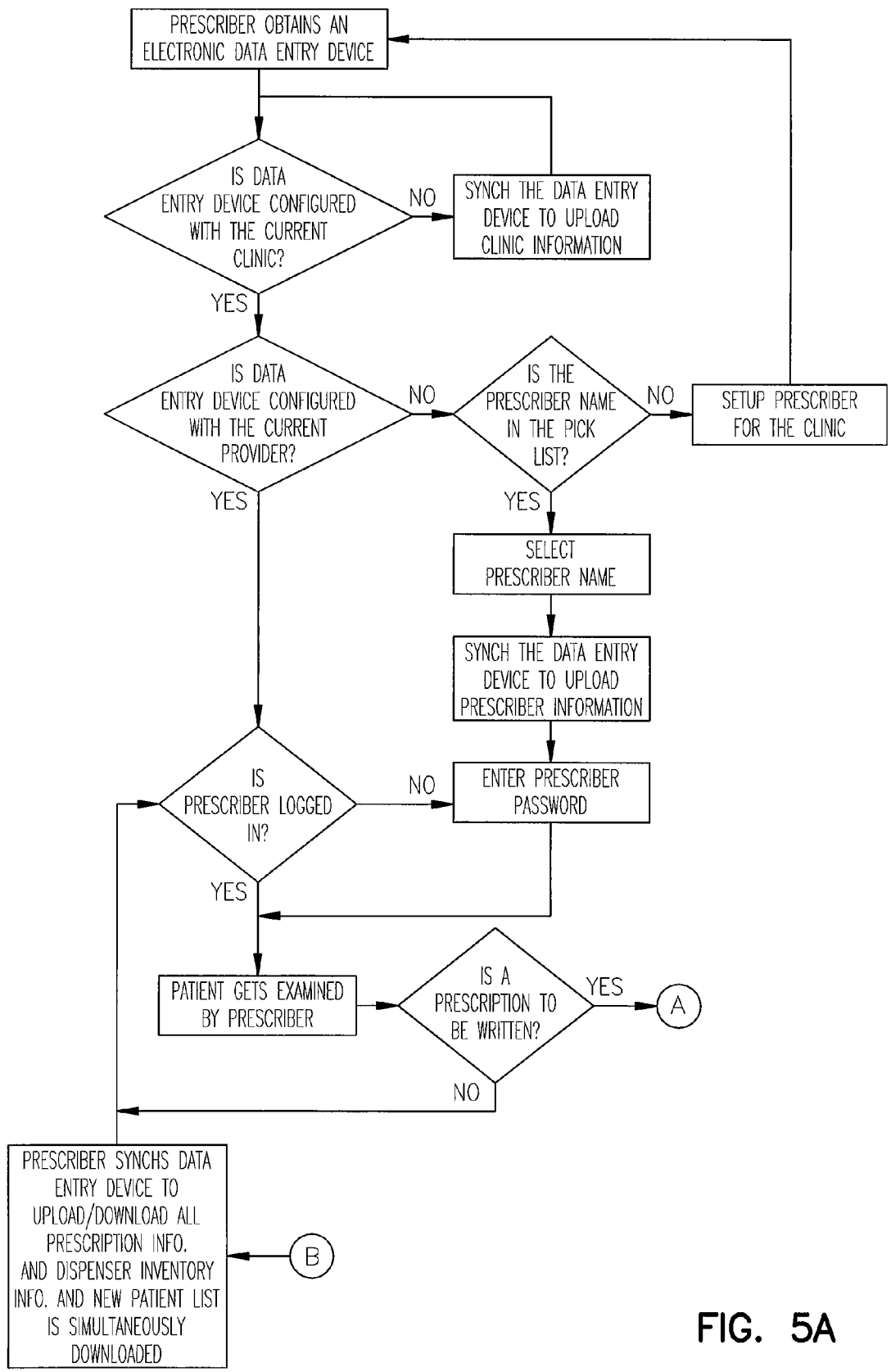
FIG. 5 is a schematic diagram of a prescription writing process according to one embodiment of the present invention.
Figure 5B:
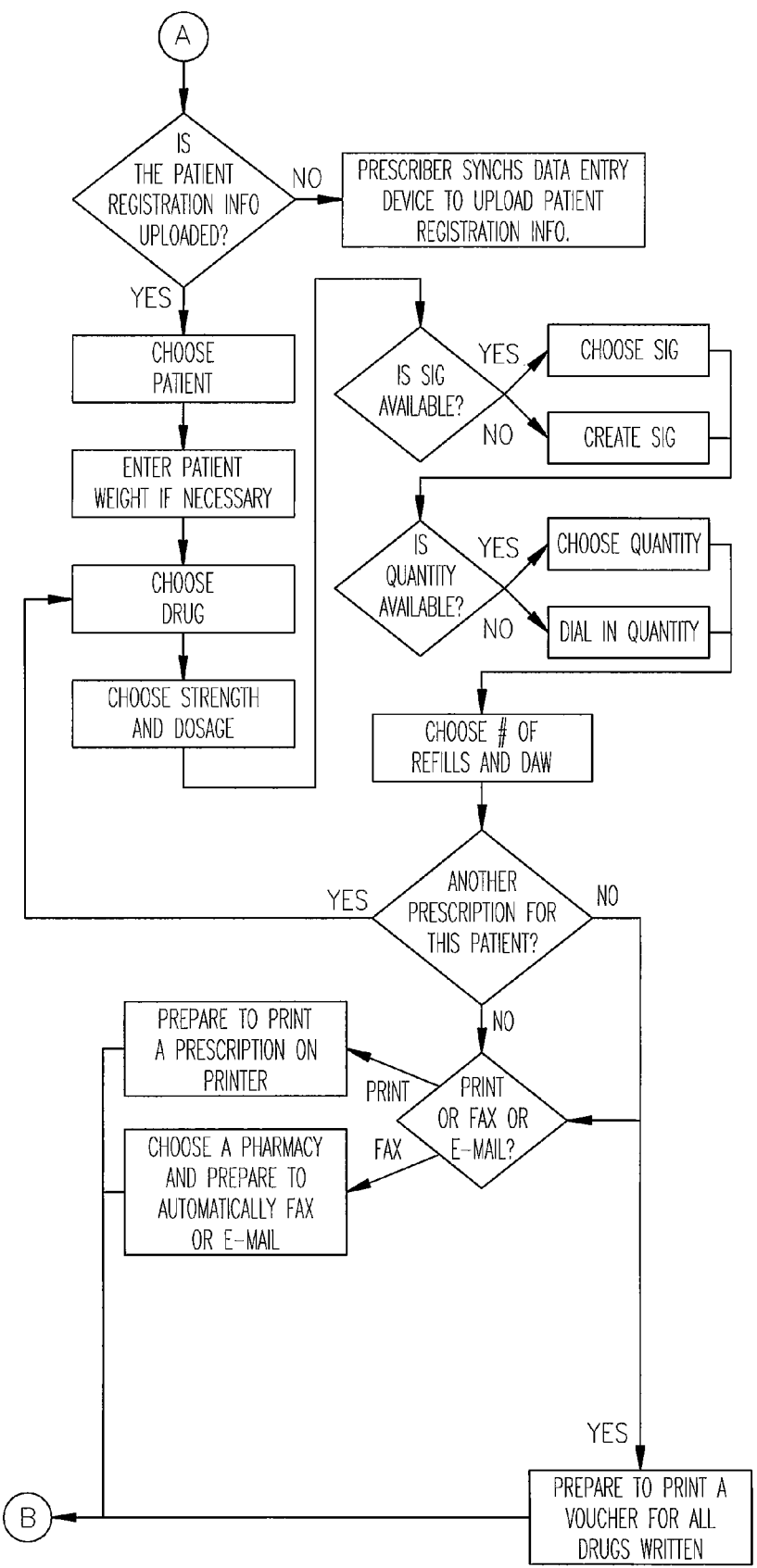

FIGS. 5A and 5B illustrate the prescription writing process in more detail. The prelude to the specific process of writing a specific prescription is for a prescriber to obtain a handheld computer 4300 (or other computer or any suitable electronic data entry device) suitably configured for the patient that is about to be examined by the prescriber. The prescriber confirms whether the computer 4300 is properly configured with information pertinent to the HCF in which it is located, a process that could occur once each day when the prescriber first arrives at the HCF. If not, a well-known synchronization (or, more commonly, a "sync") of the computer 4300 to the HCF workstation 4200 or directly to the central database server will configure the computer 4300. A similar process is required for confirmation whether the computer 4300 is configured with information pertinent to the current prescriber, a process that could occur if prescriber uses a computer 4300 that is resident at that particular HCF and shared between multiple prescribers. Once the HCF and prescriber are both properly configured in the computer 4300, the prescriber performs a password-based login process. The sync may occur via infrared frequency or may occur automatically via a number of wireless technologies.

The prescriber examines the patient and decides whether to prescribe a product. If so, the prescription writing module is activated. First it must be confirmed whether the computer 4300 is configured with information pertinent to the current patient. If not, a sync process is performed to retrieve the pertinent data from the HCF workstation 4200 or central database server. The prescriber can then choose from a "my patient" list of patients or an "all patients" list of patients. Once the computer 4300 is ready to receive a prescription for the current patient, the patient's weight is entered (if in pediatric dosage mode). The user can then choose between a list of "my medications" and "all medications." The drug lists show or flag for the prescriber which of the drugs are presently in the automatic drug dispenser. A drug is chosen, and strength and dosage of the drug are chosen. One example determines if the patient has any allergies to the medication.

Since the patient's insurance plan can be uploaded to the computer along with other patient information, each drug viewed will usually indicate whether the drug is on the patient's insurer's formulary along with its approval status and whether the drug is in the remote dispenser. If the drug is not on the patient's insurer's formulary, the prescriber may be prompted to a drug of the same therapeutic class that is covered on the patient's insurer's formulary.

A default entire prescription for the chosen drug will then appear on the computer 4300. The prescriber can accept the defaults or choose others from a list, or write in their own. The prescriber may select a well-known SIG code for the product if one is available, otherwise one may be written by the prescriber. Similarly, if a standard quantity is available, it may be chosen, otherwise the prescriber may choose a quantity. The number of refills permitted without the patient requiring a new prescription is chosen, and the prescriber indicates whether the prescription is to be "dispensed as written," i.e., an equivalent generic drug can not be substituted in place of the specific brand of drug for which the prescriber has written. The prescription may undergo a drug utilization review (DUR). This includes drug-drug interaction, dosage range checking, patient allergy checking, pregnancy and lactation alerts and other safety checks. This entire process is repeated for the each product prescribed.

As noted above, the prescription writing system includes a "pediatric" dosage calculation mode when writing a prescription for a child, for example, or at any time dosage is critical. In that case, the user has the option, before selecting the drug name, to toggle the system into pediatric dosage mode. The prescriber will then be prompted to enter the patient's weight. After that, the daily dose is selected. As the prescriber adjusts the daily dosage, the system automatically calculates the exact dosage (in units per day). The prescriber then chooses the form and strength of the drug (if the prescriber selects a dose that exceeds the maximum recommended dose/m/k/day, they will be prompted to answer a question confirming their interest in selecting that dose. The prescriber then chooses the prescription instructions. Further details of this process are shown in FIGS. 28F-29C.

It is not necessary to limit the availability of products to only the remote dispenser 3000 located at that particular HCF. The computer 4300 is able to indicate current inventory status of all remote dispensers 3000 because the sync process has given it extremely timely inventory information from the central server 2000 by way of the HCF workstation 4200. The prescriber may then determine from the patient whether the patient desires any of the products available from any of the remote dispenser(s) 3000 convenient to the patient's current location, or home, or other eventual destination. If so, the prescriber notes this on the computer 4300 so that a voucher may be generated. If not, the patient is given the option of receiving a printed traditional prescription that may be taken to a pharmacy of the patient's choice, or if the patient identifies a particular pharmacy to receive it, the prescription may be transmitted directly to that pharmacy by facsimile, e-mail, or other communications channels. In another example use of the present system, the prescriber gives a voucher to the patient and the patient takes the voucher to the dispenser. The patient can then make the decision at the dispenser whether to receive the product from the dispenser or to get a printed copy of the prescription.

Regardless of the choice, a final synchronization of the computer 4300 to the HCF workstation 4200 or central database server transfers the data to the HCF workstation 4200, the central system 2000, and the remote dispenser 3000 as appropriate. It is preferred but not required that this final synchronization also include updating the computer 4300 with not only the current inventory levels of the remote dispenser 3000 in the local HCF, but also the information pertinent to the next patients registered or scheduled to be seen by prescribers at the HCF.

Patient Discharge Process

Figure 6:
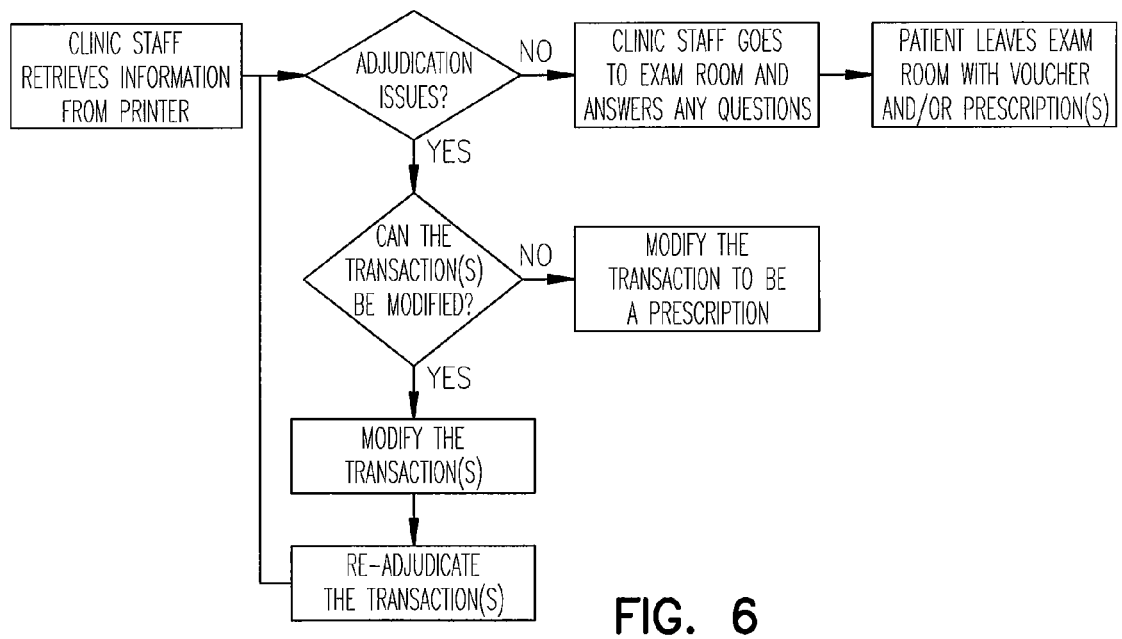
FIG. 6 is a schematic diagram of a patient discharge process according to one embodiment of the present invention.

FIG. 6 illustrates the patient discharge process in more detail. The HCF staff receives information on the prescription or voucher from the printer 4100. In one embodiment, the staff determines if there are any outstanding issues remaining from the adjudication process. If so, it may be possible to modify the transaction to permit re-adjudication, or if not the transaction is modified into a traditional prescription that cannot be filled by any of the remote dispensers or communicated to a pharmacy of the patient's choice via facsimile, e-mail or other forms of communication. Alternatively, as noted above, the call center 9050 (FIG. 1) will handle any adjudication issues. Either the traditional prescription or the adjudicated prescription (in the form of a voucher printed at printer 4100 and redeemable at the remote dispenser 3000) is taken to the examination room and presented to the patient after any outstanding questions from the patient are answered. Or, if the HCF prefers, the patient may receive either document upon leaving the HCF. Alternatively, as noted above, the patient may receive the prescription from the printer on the dispenser.

Prescription Modification Process

Figure 7:
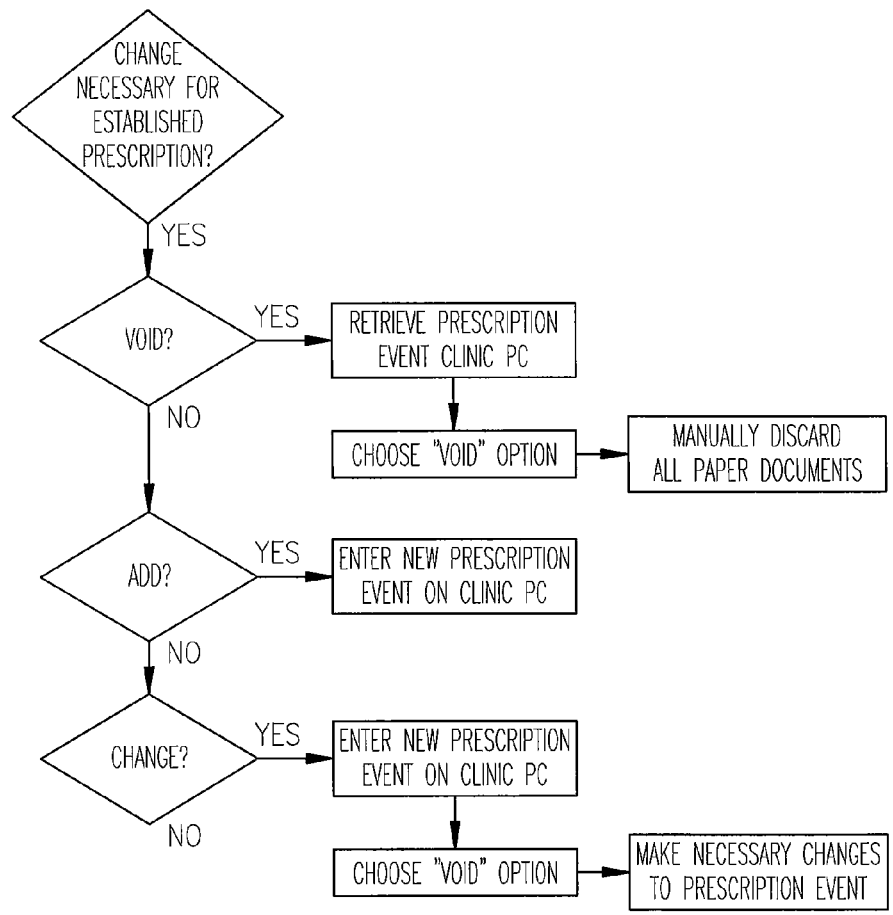
FIG. 7 is a schematic diagram of a process of modifying an established prescription according to one embodiment of the present invention.

FIG. 7 illustrates the process of modifying an established prescription. To void an established prescription entirely, the entry is retrieved from the HCF system, a "void" option is recorded, and all paper documentation of the prescription is manually discarded. Additions or changes to an existing prescription are also entered on the HCF system.

Stock Ordering Process

Figure 8:
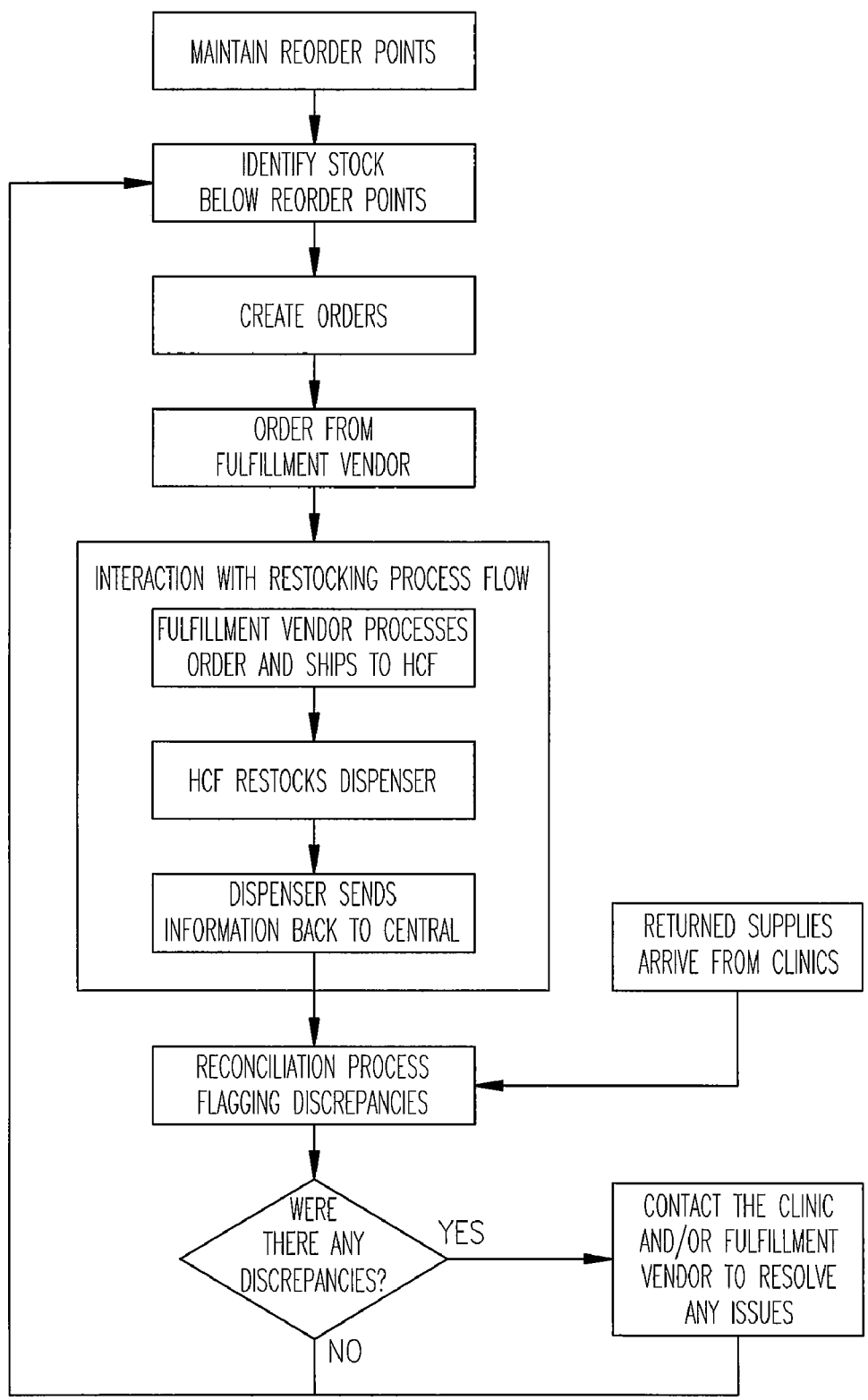
FIG. 8 is a schematic diagram of a process of ordering stock for each remote dispenser according to one embodiment of the present invention.

FIG. 8 illustrates the process of ordering stock (either product such as prescription drugs, or over-the-counter drugs, or supplies such as labels and printer paper) for each remote dispenser 3000. Because all inventory data is maintained on the central server 2000, this process is executed there. In accordance with well-known inventory control principles, reorder points (quantities and/or dates to trigger reordering) are maintained for every stock item. When the actual inventory levels identify those stock items that are at or below their reorder points, orders for such items are generated and transmitted to appropriate fulfillment vendors. The central server provides orders for each HCF in addition to an aggregate order to the fulfillment vendor (which for example, may be the HCF's own pharmacy, a repackager, a bottler, a mail-order system, etc.). The fulfillment vendor processes the order and ships the new stock to each individual HCF, even if the orders of each HCF have been aggregated together into a common order sent by the central server 2000. Personnel at each HCF or central personnel are responsible for restocking each remote dispenser 3000, and for returning any replaced or overstocked items, both as described in more detail below. Each remote dispenser 3000 automatically transmits updated inventory data to the central system 2000 where a reconciliation process identifies whether there are any discrepancies between anticipated and actual amounts and locations of each item. If there are discrepancies, they are identified and the HCF or vendor or both are notified so that all discrepancies may be resolved.

Restocking Process

Figure 9:
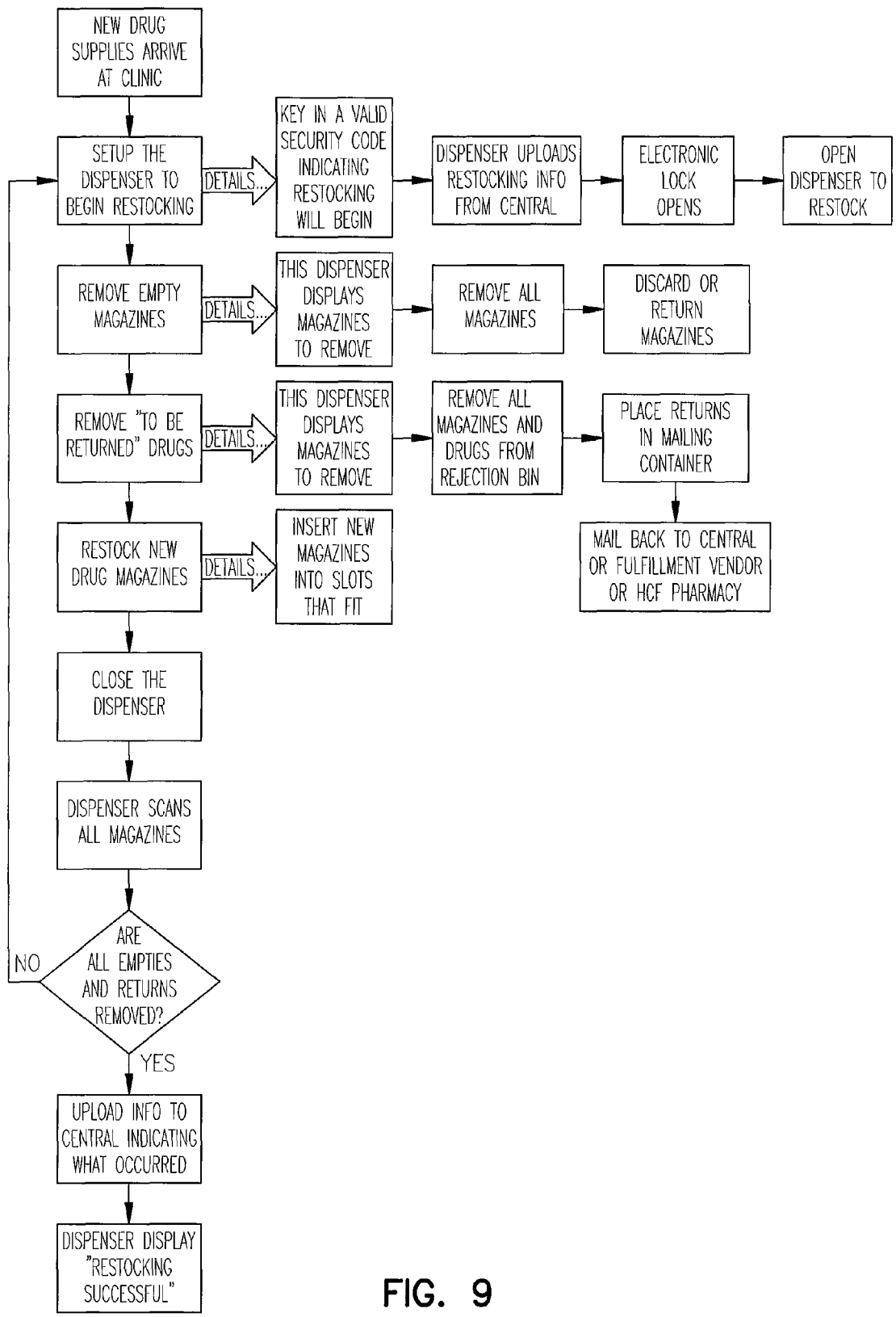
FIG. 9 is a detailed schematic diagram of the process of ordering stock for each remote dispenser according to one embodiment of the present invention.

FIG. 9 illustrates in more detail the process of restocking each remote dispenser 3000. When new items arrive at the HCF, the remote dispenser 3000 is put into restocking mode, which is preferably accomplished by entering a specific security code, which if valid, activates the manager module to contact the central system for the most recent data relevant to the restocking process. Once the security code is validated and the data is received, the portion of the remote dispenser 3000 dedicated to product inventory is unlocked and available for access. The first main task is to remove magazines that have been identified by the manager as empty of product, discarding the empty magazines themselves. Next, magazines that have been identified by the remote dispenser 3000 as containing products to be returned are removed. The individual products are removed from the magazines and returned, while the emptied magazines are discarded or returned. Then, magazines containing new supplies are installed as required.

Once the portion of the remote dispenser 3000 containing the products is closed and locked, the manager module 3200 scans all magazines to confirm whether all empty magazines and all magazines containing products to be returned have been removed, and it checks that all new magazines have been properly inserted. If not, the restocking process is not complete and must be re-performed. If so, data representing the current inventory levels and the inventory transactions that have just occurred is transmitted to the central server. Once this is complete, the visual display 3450 confirms completion of a successful restocking process. As noted above, the system rescans each slot after the product has been loaded and performs an update of the position of each product. This provides a fool-proof, safe system since a given product can be placed anywhere within the dispenser and the rescanning process will automatically update the product's position, thus not relying on any human interaction. Moreover, the FDA-approved bottler or repackager provides a trusted product.

Prescription Dispensing Process—Overview

Figure 10:
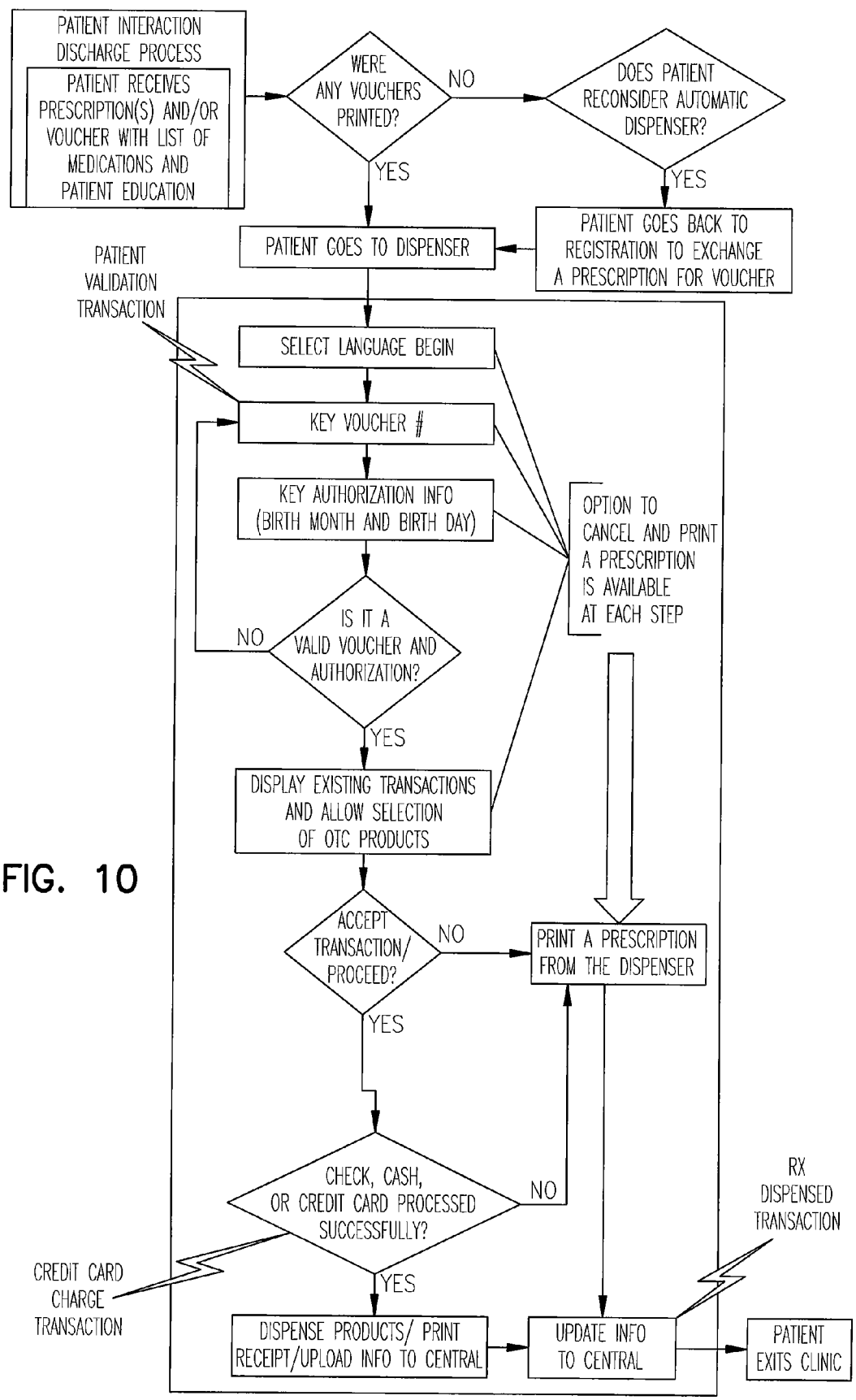
FIG. 10 is a schematic diagram of a process by which a patient has a prescription filled by the remote dispenser according to one embodiment of the present invention.

FIG. 10 illustrates the basic process by which a patient has a prescription filled by remote dispenser 3000. In the patient discharge process, the patient either received a voucher for a product located in the remote dispenser 3000, or they may exchange a traditional prescription for such a voucher (or vice versa). Once in possession of a voucher, the patient begins by selecting a language in which the remainder of the exchange with the remote dispenser 3000 will take place. Then the patient enters the unique voucher number printed on the voucher along with patient authorization data (such as birth day and birth month, but this is only an example). In one option, the voucher includes a bar code having all the necessary information and that can be scanned by the dispenser. The manager module 3200 determines whether the voucher number is valid and if so whether it properly correlates with the authorization data that the patient has entered. If not, the entry process is repeated in case erroneous data has been entered through simple human error. At this or at any other point in the process prior to acceptance of the entire voucher-based transaction, there is an option to cancel the voucher-based transaction and print a traditional prescription on printer 3950 for the patient. A further option, as discussed above, is to provide a camera to take a picture of the patient or a picture of an I.D, or other security measure such as a retinal scan.

Once a valid voucher and set of authorization data have been entered, the visual display 3450 shows a summary of existing prescriptions to be filled and a selection of possible over-the-counter (OTC) products that may be dispensed from remote dispenser 3000 without a prescription. The patient selects which if any products they wish to receive from remote dispenser 3000. The patient purchases their selections by passing a credit card through credit card reader 3850, or depositing cash, or using the check reader, or using a cell phone IR feed, or any other cash, check, debit, or electronic payment method. Manager module 3200 receives data from the credit card (or check, etc.) through credit card reader driver 3800 and transmits it to central server 2000 so that the transaction may be conducted with credit card server 6000 (or check server, etc.) in a well-known manner. As is common in the art, this may involve a repeated entry of credit card data by the patient for a variety of well-known reasons. Once the payment transaction is authorized, manager module 3200 directs dispenser module 3100 to dispense the proper products. Manager module 3200 then prints a receipt and patient information, drug education information, ads, coupons, or marketing information on printer 3950 for the patient to take with them along with their products. Manager module 3200 then sends updated inventory and transaction data to central system 2000. As noted above, during the process, the phone on the dispenser can be used to talk to someone at the central control or to a pharmacist. Moreover, after the prescription has been filled and if there are refills on the prescription, a menu on the screen can be provided to allow the patient to have the refills transferred to a pharmacy of their choice.

Remote Dispenser

Figure 11:
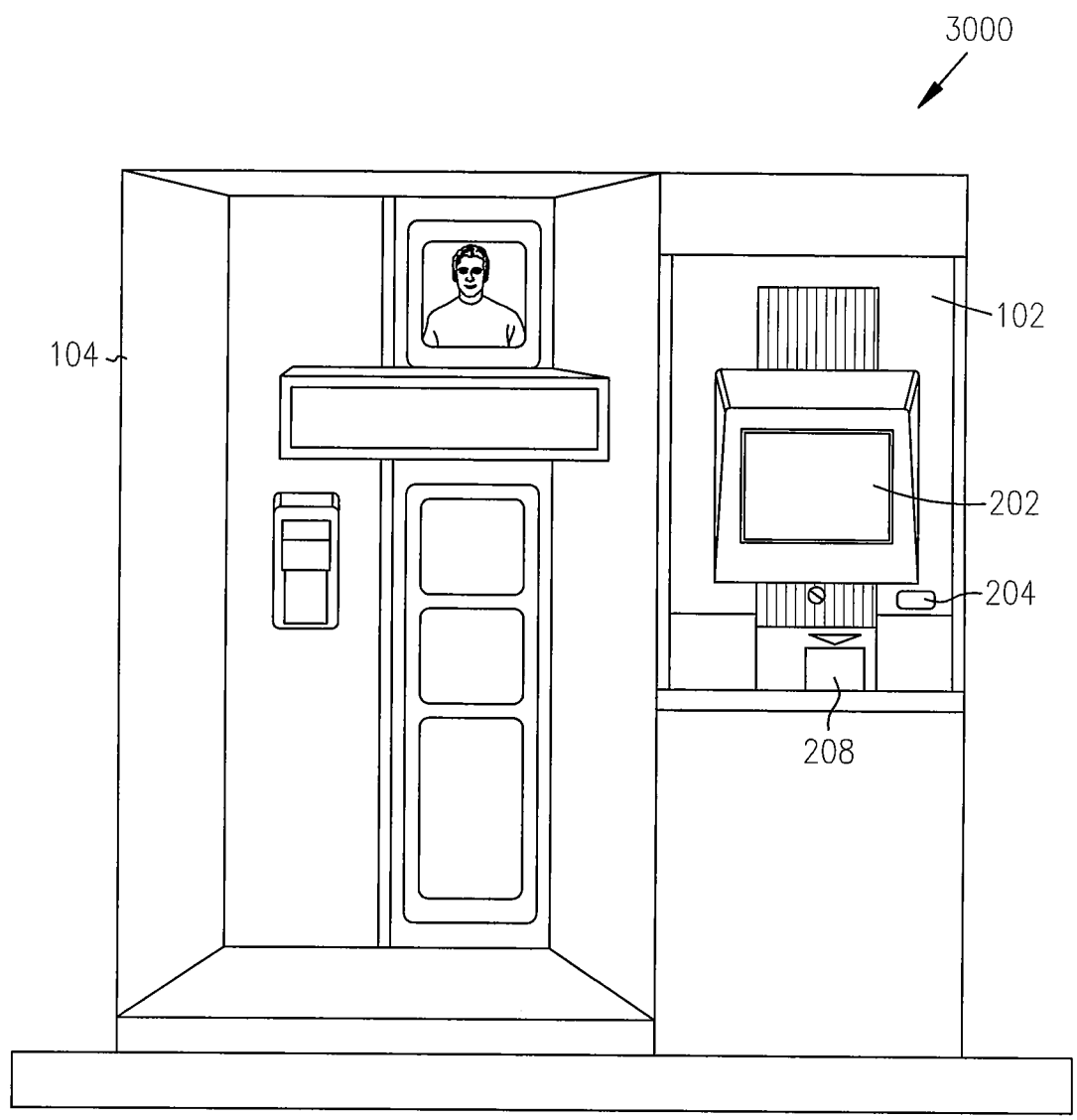
FIG. 11 is a front view of a remote dispenser according to one embodiment of the present invention.
Figure 12:
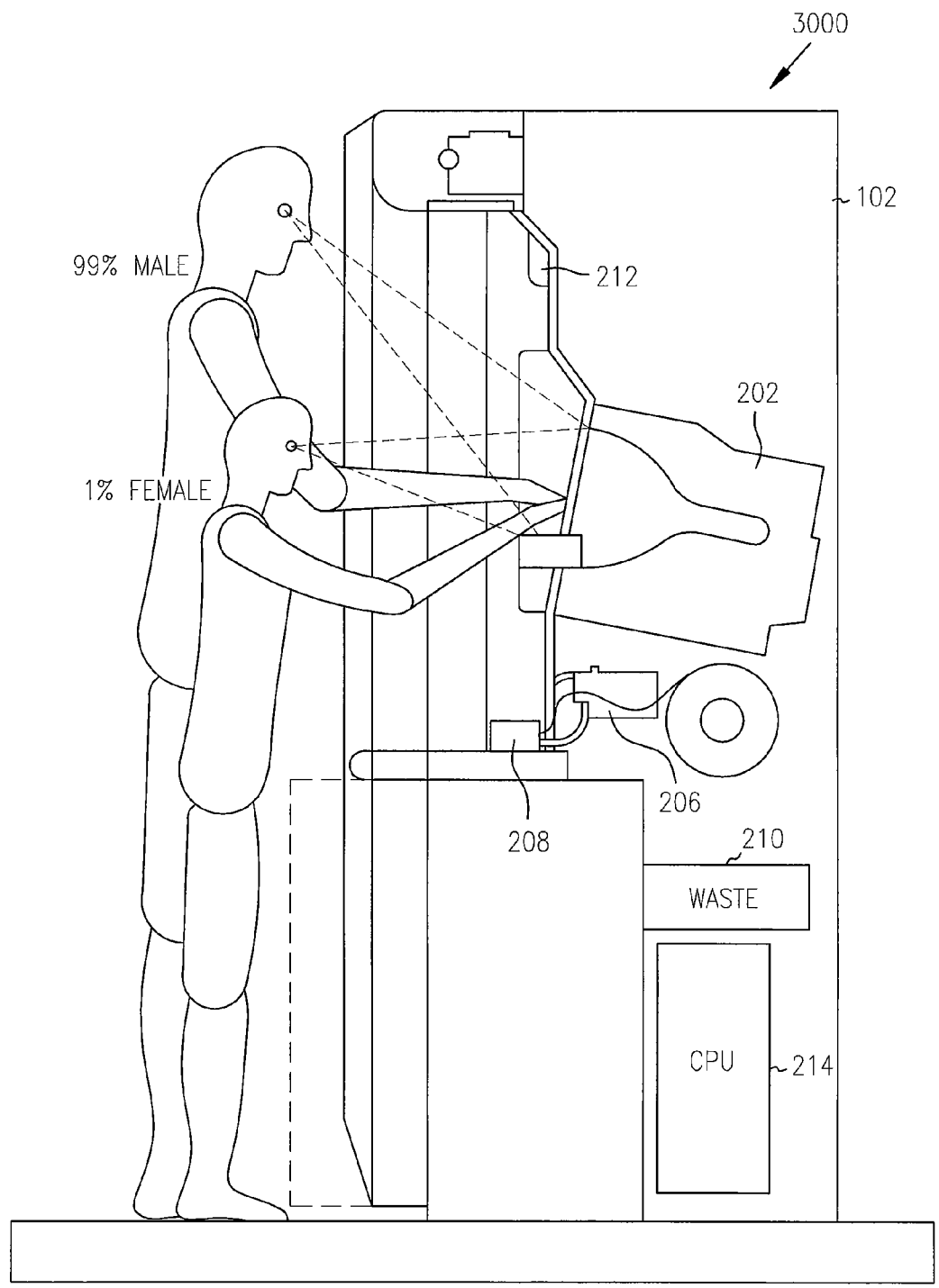
FIG. 12 is a side cross sectional view of a remote dispenser according to one embodiment of the present invention.

As shown in FIG. 11 and FIG. 12, the remote dispenser 3000 consists of a control module 102 and a cabinet module 104. Optionally, the control module and cabinet module may be housed in a single cabinet. The basic configuration includes one control module and one cabinet module. Alternatively, an additional cabinet module may be added for increased drug storage capacity.

The control module 102 houses subsystems that provide the interface between the remote dispenser 3000 and the medical patient. These components include a 17 inch Monitor with touch screen 202, a credit card reader 204, a prescriptions/instructions/receipts printer 206, a prescription/instructions/receipt output slot 208, an internal waste slot/waste basket 210, speakers 212, and a controller PC 214.

An example of hardware and software that are suitable for the controller PC 214, which is located in the control module, is a Dell OptiPlex GX110 Mini-Tower having the following specifications: GX110 Pentium III processor, 500 MHz, 512 half speed cache & Integrated NIC; Memory: 128 MB Non-ECC SDRAM (1D IMM); Keyboard: Quietkey (Space saver); Video Solution: Integrated Intel 3D graphics with Direct AGP and 4 MB Display Cache; Hard Drive: 10 GB EIDE (7200 RPM); Floppy Drive: 1.44 MB 3.5"; 4 (Min) PCI/ISA Slots; 2 (Min) serial ports; Dimension: Tower with Max size: 18∝ H×17" L×8" W; Extra Parallel Port Card; Sound Card: Sound Blaster Audio PCI (64 Voice), use with CD, DVD or CD-RW; CDROM; Network Card: Integrated 3Com EtherliNk 10/100 with ACPI and Remote Wake-up Only; and Operating System: Windows NT 4.0 Workstation SP5 with CD using NTFS. Other generally equivalently performing hardware and software could be substituted in a known manner without limiting the scope of the invention. In accordance with known principles, the design of the system should be such that the system functions are not dependent upon the particular hardware or software selected for implementation, thus permitting the system to migrate to other hardware or software platforms without any change in the scope of the invention.

The credit card reader/acceptor 204 is preferably from IDTech Company. Other generally equivalently performing hardware and software could be substituted in a known manner without limiting the scope of the invention.

The prescription/instruction/receipt printer is preferably a Datamax Ovation 2!, Direct Thermal Printer, and is located in the control module. The printer uses the same paper to print prescriptions, instructions and receipts on 4"×5" sheets. The patient information sheets are automatically trimmed to the proper length. The printer also prints product return packing slips and miscellaneous inventory transaction reports.

The remote dispenser 3000 is equipped with a temperature sensing subsystem (not shown) having both over temperature and under temperature set points. The central server is alerted if the temperature exceeds the set points.

Figure 12B:
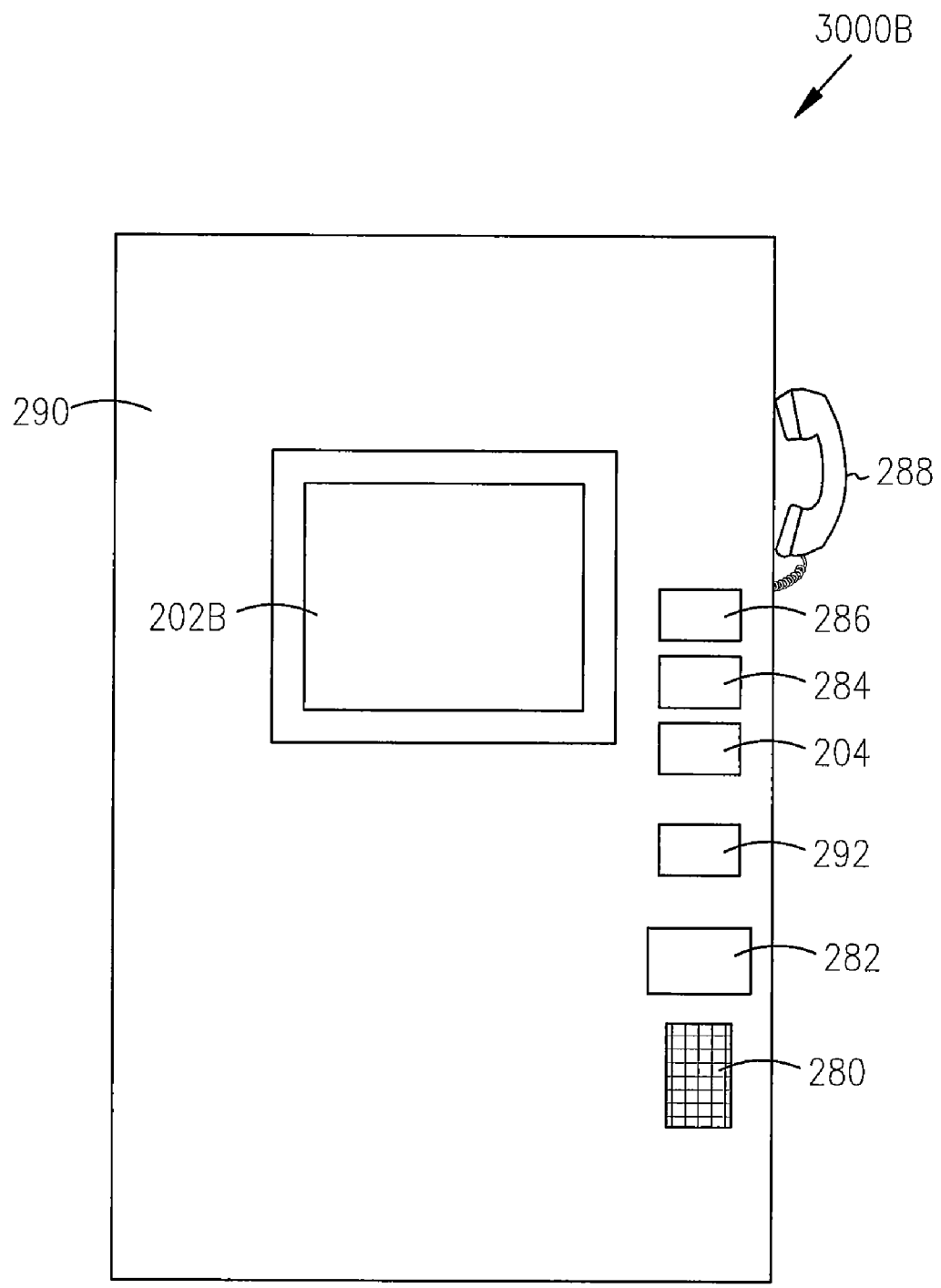
FIG. 12B is a front view of a remote dispenser according to one embodiment of the present invention.

FIG. 12B shows an automatic dispenser 3000B according to one embodiment. Dispenser 3000B includes many of the features discussed above for dispenser 3000 and certain details will be omitted for sake of clarity. Dispenser 3000B includes a flat screen monitor 202B located on the front door 290 of the dispenser 3000B. In this example, front door 290 swings open to expose the product cabinet module located behind the door. Dispenser 3000B also includes a telephone 288, an electronic lock 280, a prescription receptacle 282, a credit/debit card reader 204, a check reader 284, a cash deposit 286, and a change return 292.

Figure 13:
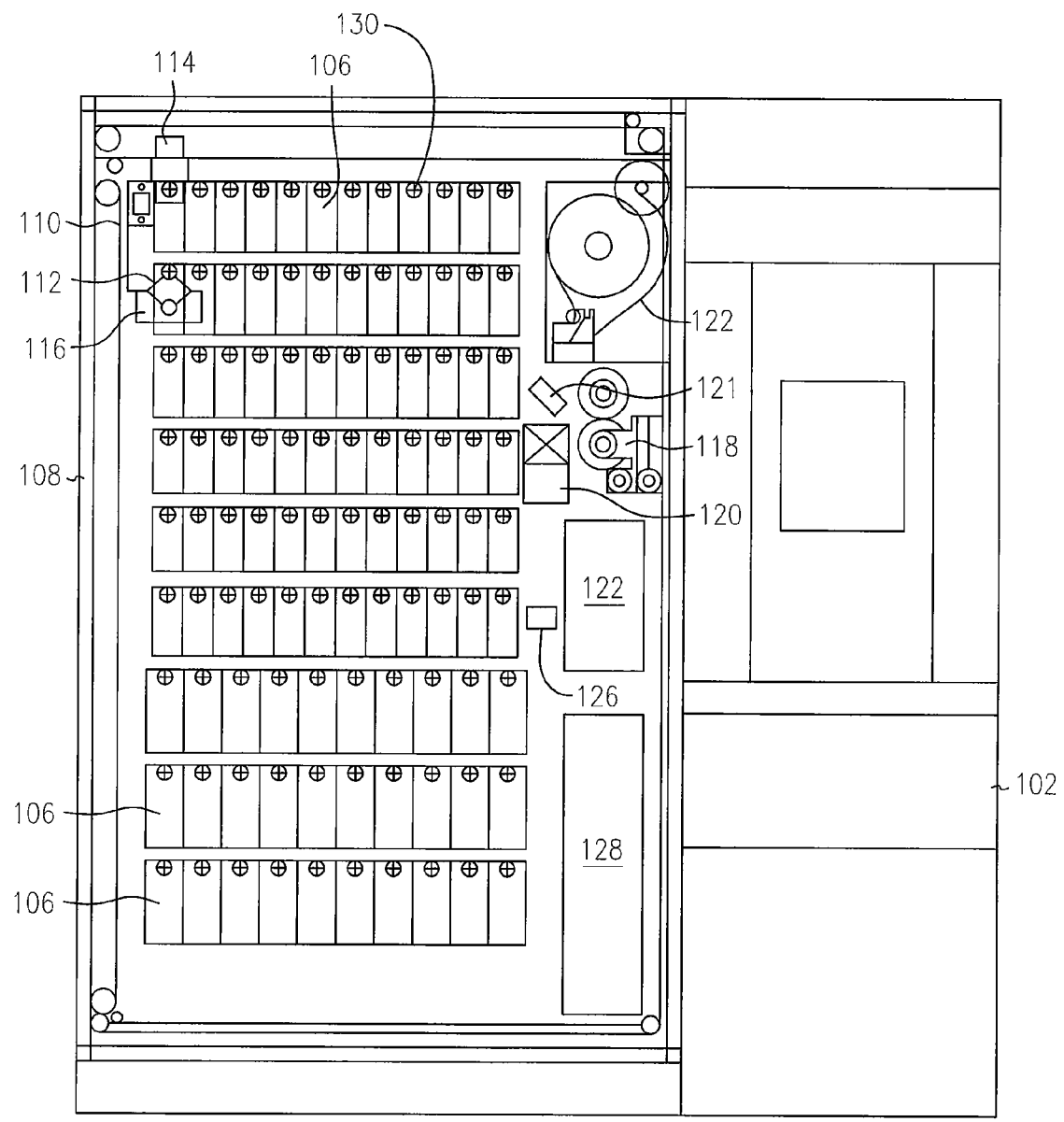
FIG. 13 is a front cross sectional view of a remote dispenser according to one embodiment of the present invention.

As shown in FIG. 13, prescription drug products are stored in the cabinet module 104 in pre-filled magazines 106 that rest on shelves and surround cantilevered lead screws 130. The products are delivered to remote dispenser 3000 in the pre-filled magazines 106 and dispensed from the magazines. A cabinet 108 encloses the cabinet module 102. The cabinet module stores product prior to dispensing and has a hinged door. The cabinet module also encloses the gantry transport system 110, product rotator 118, label printing system 122, and an uninterruptible power supply (UPS) (not shown). The UPS allows the remote dispenser to continue to function, in the event of power loss, long enough to complete any vending operation currently in progress and to achieve proper shutdown of the computer system.

The cabinet encloses a gantry system 110 that is used to position an end effector 112 and a magazine scanner 114, preferably a single directional scanner from PSC Company, model # LM520 single line laser scanner. Optionally, the remote dispenser may utilize a handheld scanner. The hand held scanner is stored inside the remote dispenser and may be used during restocking product.

The end effector 112 includes a product catcher 116 that transports the product from the magazines to a product rotator 118. The product rotator rotates the product for bar code reading by the bar code readers 120, 121 and application of the label by the label printer 122.

Bar code reader 120 is preferably an Omni directional scanner from PSC Company, model # VS800 Omni-directional laser scanner. The Omni-directional scanner 120 is located in the cabinet module and scans barcodes on the sides or bottom of product. Bar code reader 121 is preferably a single directional scanner from PSC Company, model # LM520, single line laser scanner. Bar code reader 121 is used to scan the side of product while in the product spinner.

The label printer 122 is preferably a Datamax Ovation 2! having a thermal transfer ribbon attachment. Optionally, the printer may use a direct thermal technique. The label printer prints 2"×4" prescription container labels with bar codes and is compatible with the label applicator.

After the product is labeled, the product is dispensed through the product chute 124 by activating the chute door motor 126 or if the product is rejected it is sent to the reject bin 128. The product chute allows the labelled drug to be delivered to the patient at the remote dispenser, while preventing any individual from reaching into the chute to the point of being injured. Additionally, the control module is in a location proximate to the product chute where the product is dispensed to the patient.

The reject bin is a receptacle which stores products that do not pass the bar scan checks. The packages are later removed and returned to the vendor.

Figure 14:
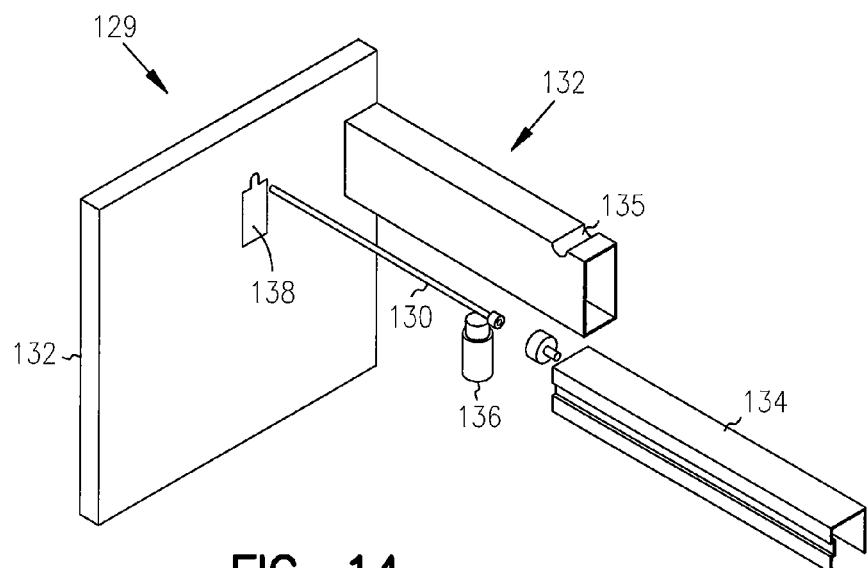
FIG. 14 is an exploded perspective view a magazine and lead screw system according to one embodiment of the present invention.

FIG. 14 shows an exploded perspective view of the magazine and lead screw system 129. The cantilevered lead screws 130 are mounted to the inside back panel 132 of the cabinet module 104. In one example, the magazine 106 is mounted on the lead screw 130. Alternatively, a shelf is provided for the magazine to rest on. The magazine cartridge consists of a cardboard outer shell 132 and a vacuum molded inner portion 134. The product 136 is stored within the magazine 106. A pusher 138 for moving the product is threaded on the lead screw. The lead screw and pusher are mechanical elements designed to support the magazine within the cabinet module and to dispense product from the magazine. The lead screw is a threaded rod which, when rotated, causes the pusher to advance. The pusher is used to advance the product within the magazine assembly during the dispensing process. The magazine itself contains the product for a given magazine position (one specific product for a given position).

The magazine is a container that serves the dual purpose of a shipping carton and product-dispensing magazine. The magazine can include three principle components: a corrugated (cardboard) paper outer shell 132, a vacuum-molded plastic inner liner portion 134, and a bar code label 135 placed on the outboard end of the magazine. The outer shell is a tube designed to support the inner portion during shipping and handling and during application inside the remote dispenser. The inner liner portion is designed to prevent the product from changing orientation during shipping and handling, as well as to align the magazine to the lead screw and to guide the products during the dispensing process. The bar code label is used to identify the contents of the specific magazine so that the appropriate preprogrammed dispensing procedure is affected. If the magazine rests on a shelf, the liner 134 can be omitted. The exterior surface of the magazine may also contain a legible label stating the drug product content of that magazine. However, the barcode label 135 on the outside of the magazine may have the drug product name printed in English (or other language) in addition to the barcode or the product package is readable within the magazine.

Figure 15:
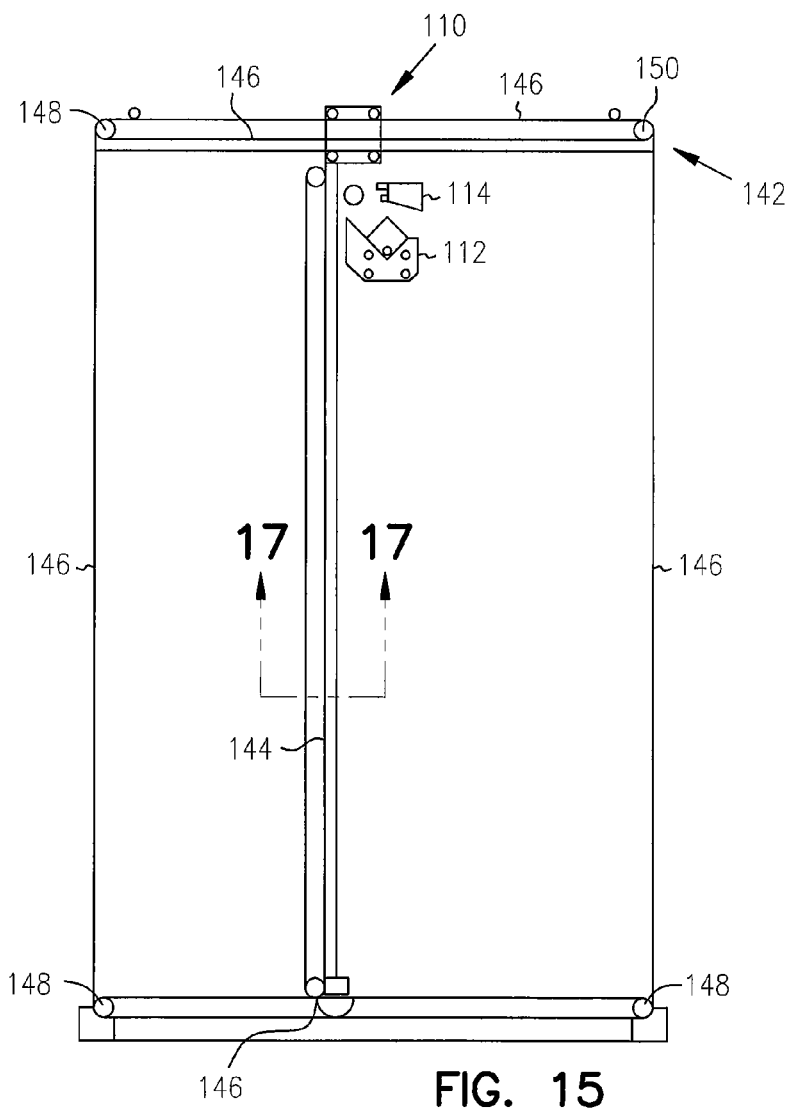
FIG. 15 is a front view of a gantry transport system according to one embodiment of the present invention.

FIG. 15 is a front view of the gantry transport system 110. The gantry transport system 110 is a two-dimension robotic assembly used to position the end effector 112 at a given magazine position. Additionally, the gantry system transports the product from the magazine to the product rotator and label printer and also positions the magazine scanner 114.

The gantry transport system 110 includes an x-axis system 142 and an y-axis system 144. The x-axis system moves the y-axis system and the end effector 112 from side to side, while the y-axis system moves the end effector 112 up and down. The x-axis system includes an x-axis belt/cable 146, x-axis pulleys 148, and an x-axis motor system 150. The x-axis system consists of a belt 146 looped around pulleys 148 and a cable 146 looped around idler pulleys 148. The motor system 150 consists of a motor, gearbox power supply and controller. As the controller signals the stepper motor, the motor repositions the belts and cables and moves the y-axis system from side to side.

As shown in FIG. 16, the y-axis system consists of an y-axis belt/cable 152, y-axis pulleys 154, and an y-axis motor system 156.

FIG. 17 is a cross sectional view of the y-axis transport system. The y-axis system is supported on a frame structure 158. The frame structure consists of a Lexan rail 160 affixed to an aluminum tube 162. Guide wheels 164 aligned the y-axis system along rail 160.

Figure 18:
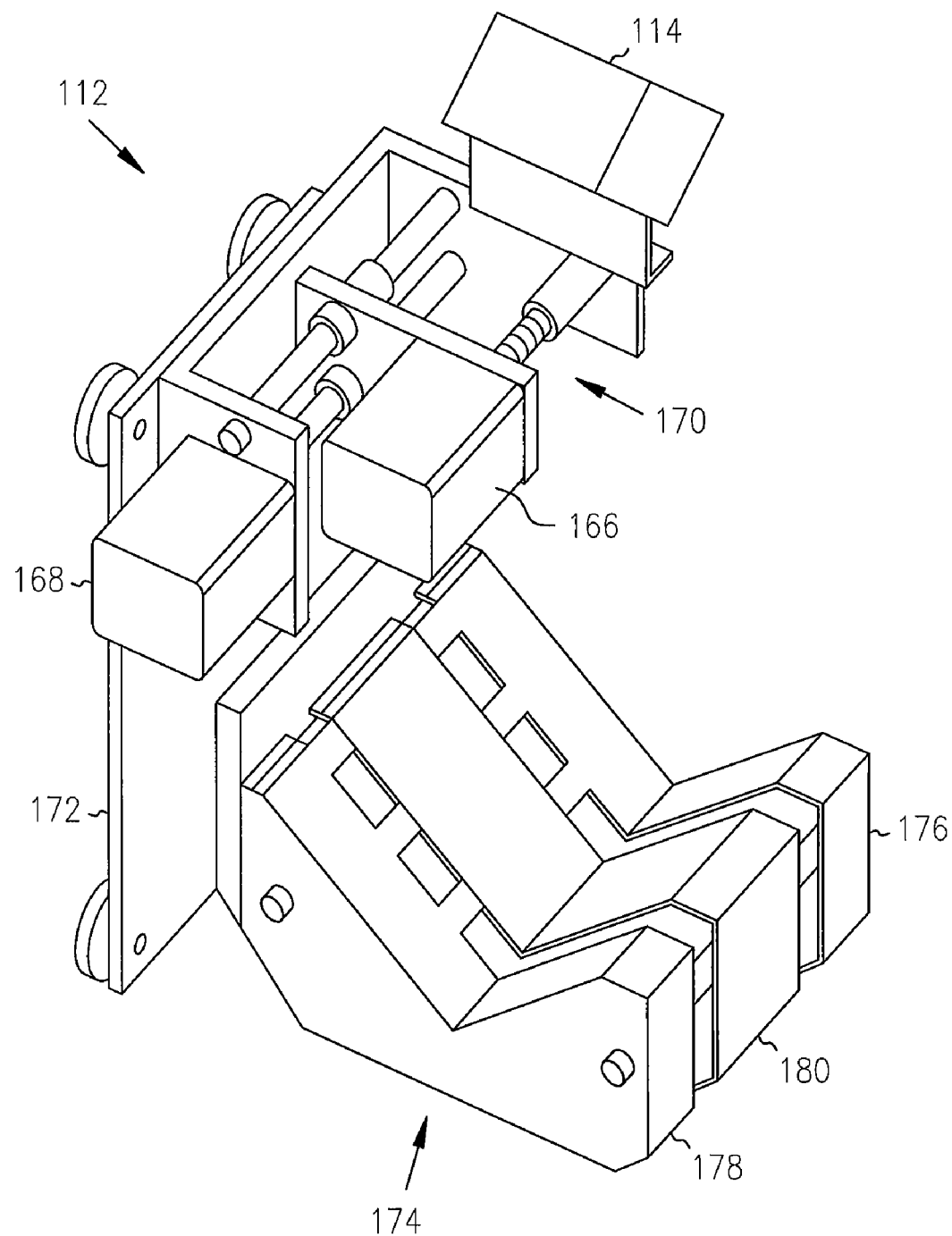
FIG. 18 is a perspective view of an end effector according to one embodiment of the present invention.

FIG. 18 is a perspective view of end effector 112. The end effector is a mechanical device mounted on the gantry transport system and is used to retrieve and transport the product during the dispensing process. The end effector 112 includes the magazine bar-code scanner 114, a drive screw motor 166, a lead screw coupler motor 168, an optical sensor 170, a mounting plate 172, and a product catcher 174. The lead screw coupler motor 168 advances a drive adapter (not shown) to couple to the lead screw. Optical sensor 170, upon detecting the "fall" of a product into the product catcher, signals the lead screw drive motor to stop advancing the product out of the magazine tube. The product catcher captures the product as it is advanced out of the magazine. The product catcher includes a stationary mitt 180, and outside moveable mitts 176, 178. In some examples, the drive screw is omitted and each of the lead screws 130 is driven by a separate motor associated with each lead screw and controlled by the dispenser's controller.

Figure 19:
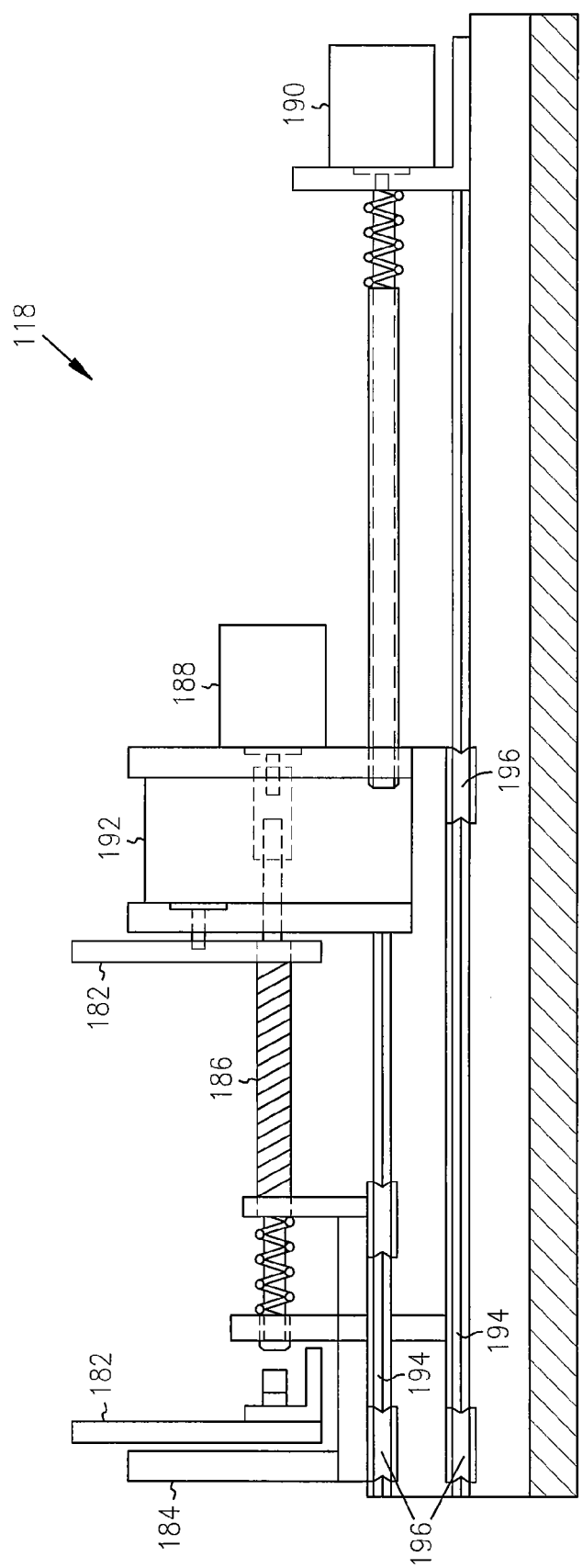
FIG. 19 is a side view of a product rotator according to one embodiment of the present invention.

FIG. 19 shows a side view of product rotator 118. The product rotator serves the function of spinning the product in the barcode scanner beam, so that the product can be identified, and rotating the product as the product label is applied. The product rotator 118 consists of two rotating disks 182, one of which is mounted to a traveling arm 184 that is actuated by a screw 186 that is driven by motor 188. When the package is transferred to the product rotator, the traveling arm 184 is moved inward, the disks are brought together, and the package is captured between the disks. A second motor 190 then acts via a second screw to position the entire rotator mechanism under the label printer. A third motor 192 spins the disks and rotates the package to effect label application. The traveling arm 184 moves along rails 194 on guide wheels 196.

Figure 20:
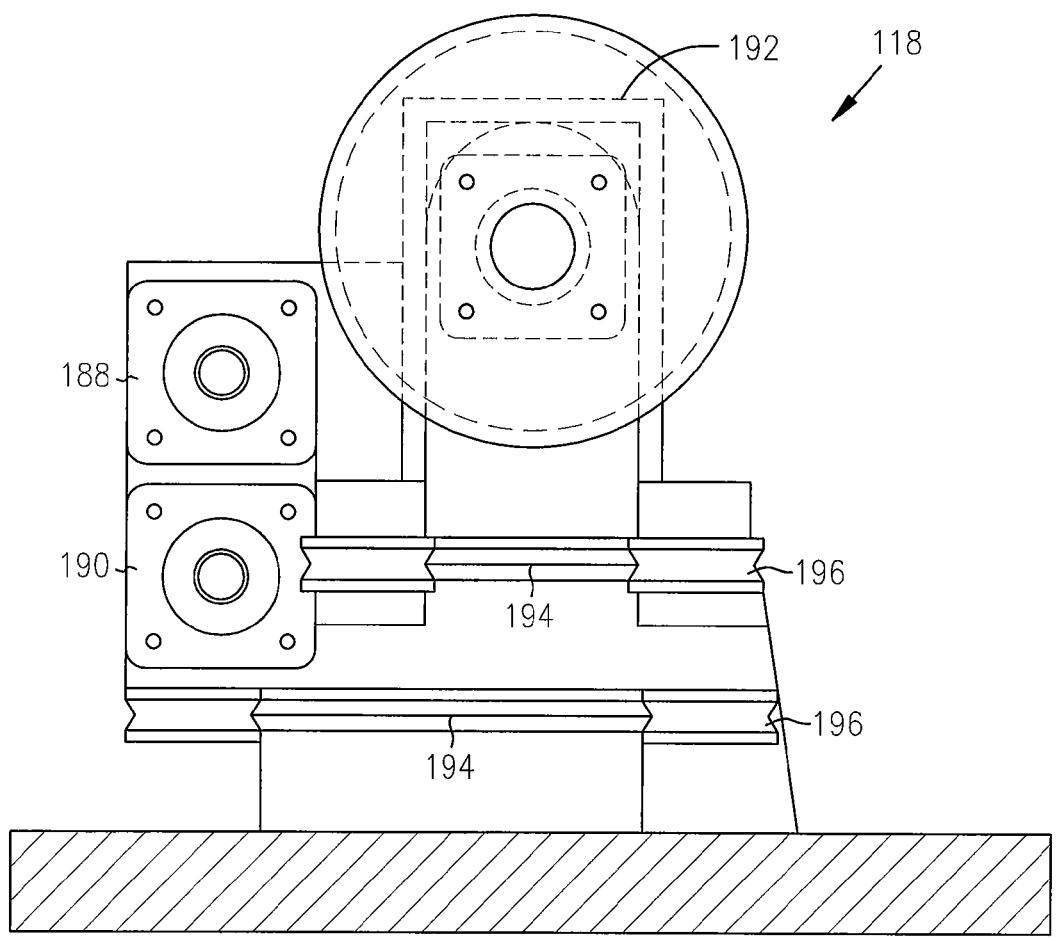
FIG. 20 is an end view of the product rotator according to one embodiment of the present invention.

FIG. 20, shows an end view of the product rotator 118 showing the positioning of motors 188, 190, and 192 and the positioning of rails 194 and guide wheels 196.

Figure 21:
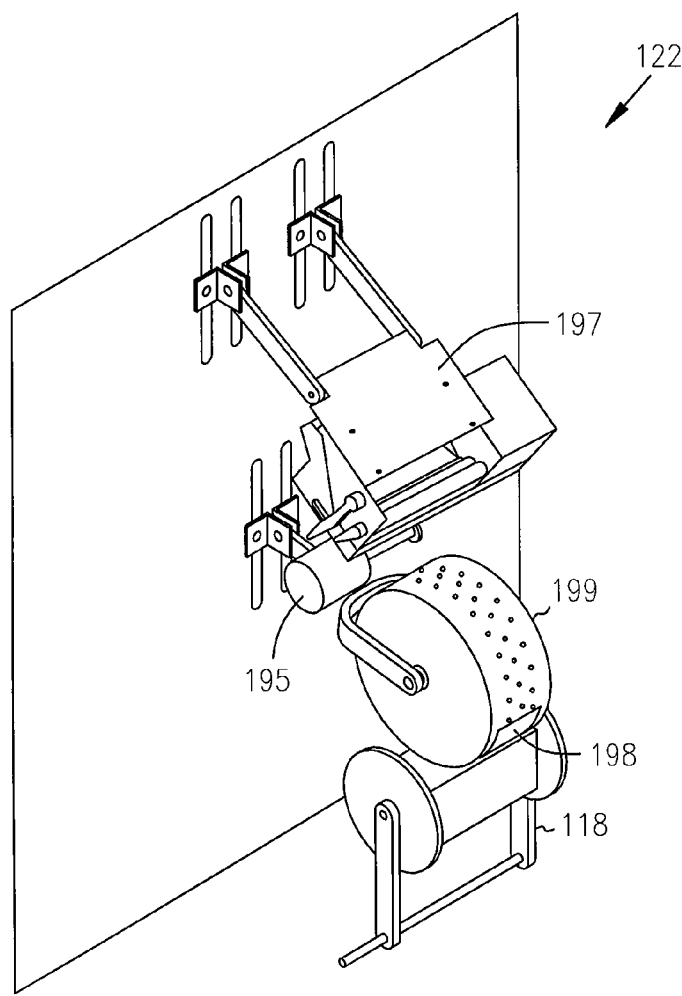
FIG. 21 is a perspective view of a label printer assembly according to one embodiment of the present invention.

FIG. 21 shows a perspective view of label printer 122. The printer mechanism 197 generates an adhesive-backed package label 198 and advances the label toward a transfer wheel 199. The label 198 is held on the surface of the transfer wheel 199 by vacuum (adhesive side of label is outward) while the drive motor (not shown) advances the transfer wheel. A solenoid 195 retracts and allows the transfer wheel to swing to the product rotator 118 for label application. The label makes contact with the product package while the product rotator spins the package at which point the label adheres to and is transferred to the package. As the product spins, wheel 199 is supported by the product itself. As such, the wheel can accommodate almost any shape of box, bottle, or other item that needs labeling. In various embodiment, other types of labelers can be used including, adhesive labelers, etc.

Figure 22:
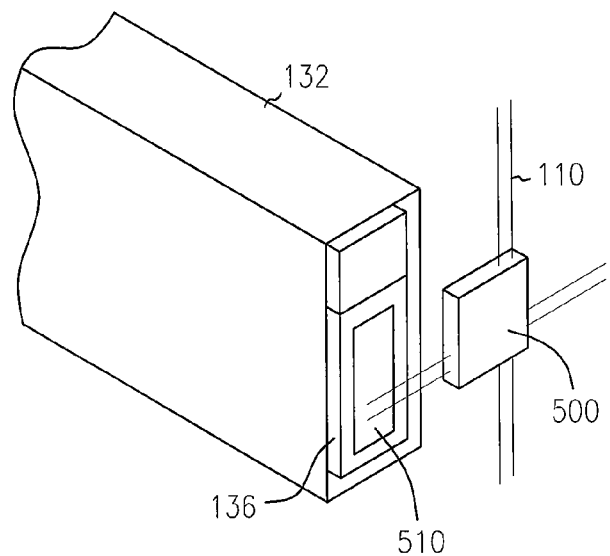
FIG. 22 is a perspective view of a moveable printer according to one embodiment of the present invention.

As shown in FIG. 13, one of bar-code scanners 120, 121 is used to scan the pre-labeled product to verify that it is the right product. If not, the product is sent to reject bin 128 (FIGS. 13 and 22C). Also, after the product has been labeled by the labeling system 199, one of scanners 120, 121 scans the label. Again, if it is mislabeled, the product is sent to the reject bin.

Accordingly, to dispense a prescription product from the present system, the system requires the product to go through three scans. First, the magazine is scanned to identify the magazine holding the product, then the product itself is scanned, finally the labeled product is scanned. This triple check process is rigorous enough to satisfy some current state laws for dispensing prescriptions. Moreover, it is anticipated that most states will allow use of the system once a state review board has reviewed the process. Accordingly, the present system provides a safe system for the dispensing of prescriptions without the intervention of a pharmacist, or any human intervention at all.

Figure 22B:
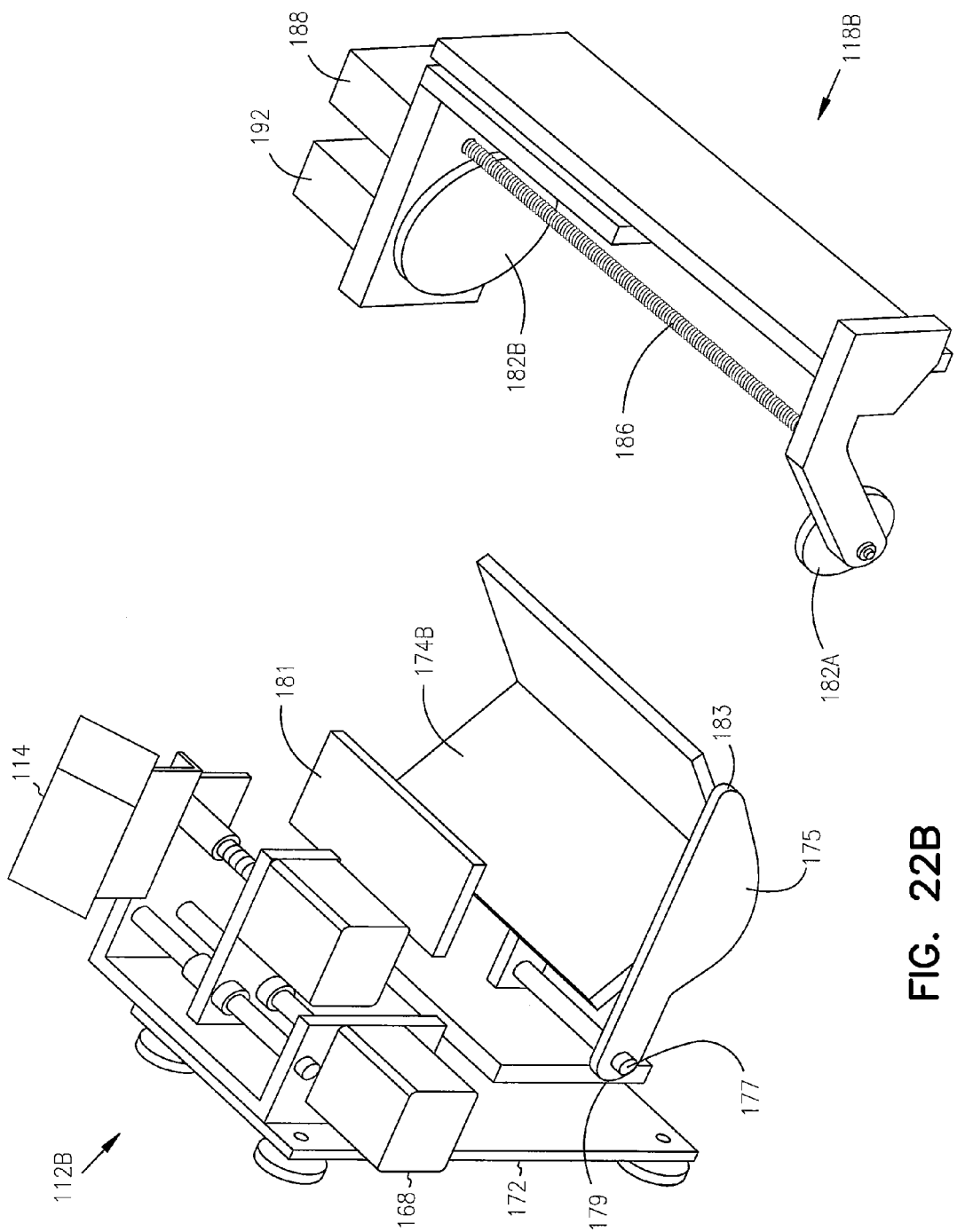
FIG. 22B shows a perspective view of portions of a dispenser according to one embodiment.
Figure 22C:
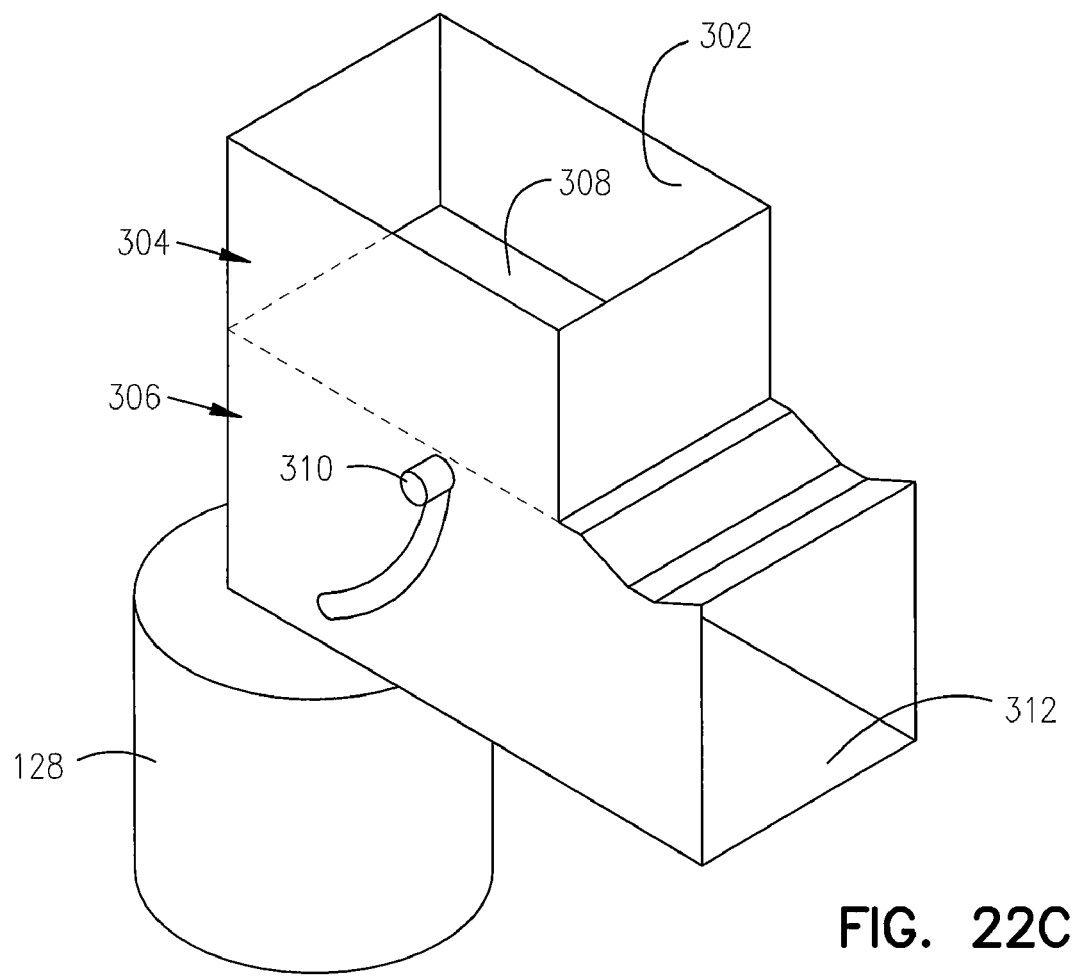
FIG. 22C shows a perspective view of a product delivery chute according to one embodiment.

FIGS. 22B-22C show a product transporting system according to one embodiment. This embodiment includes some of the same features as discussed above for FIGS. 13-22 and some details are omitted for sake of clarity.

FIG. 22B shows an end effector 112B and a product rotator 118B. In this example, end effector 112B includes a product catcher 174B that includes a V-shaped cross-section. A product that falls into catcher 174B is prevented from falling off of the catcher by a gate 175. Gate 175 includes a first side 179 which is rotatably coupled to the end effector 112B using a pivot bar 177. The main body portion of gate 175 covers the outer, open end of catcher 174B. A second end 183 of gate 175 is positioned to abut wheel 182A of product rotator 1118B when the end effector is brought into position proximate the product rotator 118B. For example, as the end effector 112B is translated towards product rotator 118B, wheel 182A lifts gate 175 until the end effector is located such that wheels 182A and 182B are approximately aligned on either end of the product which is lying on the bottom of V-shaped catcher tray 174B. Then as described above, motor 188 drives screw 186 to bring wheel 182A towards wheel 182B until the product is held between the two wheels. In this embodiment, wheel 182A is smaller than in the previous example. This allows the wheel to clear the catcher as it travels over the catcher to grasp the product.

FIG. 22C shows a product delivery chute 302 according to one embodiment. Product delivery chute includes a product holding portion 304 and a product delivery portion 306. These two portions 304 and 306 are separated by a movable member 308. Movable member 308 acts as the floor of holding portion 304. As products are labeled by the system, they are dropped into holding portion 304. After all the products for a patient have been prepared, an actuating member 181 (See FIG. 22B) on end effector 112B contacts and activates a mechanism 310 that opens movable member 308, thus allowing the products to fall into product delivery portion 306. Product delivery portion 306 is in open communication with the reach-in slot 312, allowing the patient to pick up their products. This two-step delivery process keeps all the products in one place until they are presented to the patient. Thus, a patient won't grab the first one out and forget to take the rest.

Product Dispensing Process

The dispensing process will not initiate until the patient (or HCF staff, or other authorized user) has entered all required information and the cash, check, credit card, and/or insurance payment (if necessary) has been verified for inputs required to allow drugs to be dispensed.

In one embodiment, referring generally to FIGS. 13-22, the sequence of events in dispensing a product is as follows:

1. The x- and y-axis gantry motors position the end effector in the correct magazine location. The lead screw positioner motor extends the coupler on the end effector toward the mating coupler on the lead screw, until the two couplers are intermeshed but not in contact, which prevents excessive loads from being transmitted to the cantilever lead screw assembly. A load sensor (e.g. a spring and a proximity sensor) is used to apply a known tip load on the cantilever lead screw assembly. The x- and y-axis gantry motors are then powered down to eliminate additional forces being exerted. The drive screw motor 166 then engages the coupler until the sensor detects the necessary load, after which the y-motor is powered up and lifts the end effector a pre-calculated number of steps to unload the lead screw bearing. In an alternative embodiment, each lead screw has a motor attached thereto and the system turns on each motor as necessary to advance the pusher and dispel the product.

2. The drive screw motor 166 rotates the spring-loaded conical coupler/lead screw, advancing the pusher to dispense the product into the catcher of the end effector.

3. An optical sensor, positioned to detect the product as it falls into the catcher, signals the drive screw motor to stop advancing the product.

4. The product is transported via the end effector to the product rotator, where telescoping catcher is compressed by the product rotator. At the same time the product is then grasped and held between two rubber-faced disks, one idler and one driver disk.

5. The clamp pressure is controlled by preset position/calibration of a proximity sensor and compression spring displacement.

6. The product rotator rotates the package until scanned to verify that the correct drug is being dispensed. If the scan is successful, the remote dispenser completes steps 7 through 10 below. If the scan is not successful, the product is dropped into the reject bin and the process returns to step 1. If the scan reveals that the correct drug is not being dispensed, the magazine location is recorded, the HCF is alerted, and the process returns to step 1 at another magazine location for the same drug.

7. The label printer generates an adhesive-backed package label and advances the label toward the transfer wheel. On example provides a labeling system which attaches in part via static electricity.

8. The label is held on the surface of the transfer wheel by vacuum (adhesive side of label is outward) while the drive motor advances the transfer wheel. A solenoid retracts and allows the transfer wheel to swing to the product rotator for label application.

9. The product rotator spins the package and the label on the roller is lowered onto the product package at which point the label adheres to and is transferred to the package.

10. The scanner checks the applied label to verify that the label was applied properly.

11. A flapper moves to divert the labeled package into the dispensing chute.

12. The rotator disks retract allowing the package to drop, and the product is directed to the package output portal of the remote dispenser.

In another embodiment, referring generally to FIGS. 13-22, and 22B-22C, the sequence of events in dispensing a product is as follows:

1. The x- and y-axis gantry motors position the end effector in the correct magazine location. The lead screw positioner motor extends the coupler on the end effector toward the mating coupler on the lead screw, until the two couplers are intermeshed but not in contact, which prevents excessive loads from being transmitted to the cantilever lead screw assembly. A load sensor (e.g. a spring and a proximity sensor) is used to apply a known tip load on the cantilever lead screw assembly. The x- and y-axis gantry motors are then powered down to eliminate additional forces being exerted. The drive screw motor 166 then engages the coupler until the sensor detects the necessary load, after which the y-motor is powered up and lifts the end effector a pre-calculated number of steps to unload the lead screw bearing.

2. The drive screw motor 166 rotates the spring-loaded conical coupler/lead screw, advancing the pusher to dispense the product into the catcher of the end effector.

3. An optical sensor (or other sensor), positioned to detect the product as it falls into the catcher, signals the drive screw motor to stop advancing the product.

4. The product is transported via the end effector to the product rotator, where one wheel of the product rotator lifts the gate on the catcher and then the product is grasped and held between two rubber-faced disks or wheels, one idler and one driver disk.

5. The clamp pressure is controlled by preset position/calibration of a proximity sensor and compression spring displacement.

6. The product rotator rotates the package until scanned to verify that the correct drug is being dispensed. If the scan is successful, the remote dispenser completes steps 7 through 10 below. If the scan is not successful, the product is dropped into the reject bin 128 and the process returns to step 1. If the scan reveals that the correct drug is not being dispensed, the magazine location is recorded, the HCF is alerted, and the process returns to step 1 at another magazine location for the same drug, if any. Otherwise a prescription is generated.

7. The label printer generates an adhesive-backed package label and advances the label toward the transfer wheel. (O.T.C. products and water for reconstitution do not need to be relabeled).

8. The label is held on the surface of the transfer wheel by vacuum (adhesive side of label is outward) while the drive motor advances the transfer wheel. A solenoid retracts and allows the transfer wheel to swing to the product rotator for label application.

9. The product rotator spins the package and the label on the roller is lowered onto the product package at which point the label adheres to and is transferred to the package.

10. The scanner checks the applied label to verify that the label was applied properly.

11. If the label is correct, the product rotator moves so that product is over the dispense chute.

12. The rotator disks retract allowing the package to drop and the product is directed to the product holding area.

13. When all products have been delivered to the product holding area, the gantry moves and causes the catcher to actuate the floor of the holding area to release products to the output portal or delivery portion of the dispenser.

Stocking/Restocking Process

Upon sending a new shipment of drugs to the remote dispenser, the product supplier also sends an electronic file, referred to as the product file that contains data on the contents of the shipment.

Preparing the remote dispenser for restocking consists of one or more of the following steps: a) Inserting a security code and having the code validated by the central server, b) Opening the cabinet door after using the electronic lock, c) Scanning the shipper bar code located on the outside of the shipping carton (or on the packing slip), d) Displaying the descriptions and locations of magazines to be removed and returned to the vendor including magazines that are empty or products to be returned for various reasons, e) Removing all empty magazines, f) Removing magazines listed on the display and scanning the magazine barcode, g) Indicating if the correct magazine was removed, h) Displaying the status of the magazines by color, i) Scanning the barcode of each package from the return bin that is to be returned to the vendor as well as any packages that have fallen from the magazine to the bottom of the remote dispenser, or alternatively just returning the packages unscanned, j) Keying barcodes for packages that will not scan properly, k) displaying all scanned and keyed return products, l) Placing return products in a return shipping carton, m) printing a packing slip of return items and placing the packing slip in the return shipping carton for shipping to the vendor or to the HCF pharmacy, and n) sending an electronic soft copy of the packing slip to the central server.

The process of refilling the remote dispenser consists of one or more of the following steps: a) Displaying the magazines in the new shipment, b) Scanning the barcode on each magazine from the new shipment, the barcode indicating the contents of the magazine, c) Displaying an indication that the magazine was received, d) returning unreadable or unlisted magazines to the vendor, e) loading the new magazines into any refill location, f) guiding the new magazine onto the lead screw at the refill location, g) pushing the new magazine fully onto the lead screw assembly, h) closing the cabinet door, and i) automatically scanning the barcodes at the front of each magazine to confirm placement and location.

FIG. 22 shows another embodiment of the present invention. A moveable printer 500 moves on the gantry transport system 110 as discussed above. The printer 500, such as an inkjet printer, directly prints on the package 136 or directly prints on a label 510 that is attached to the package 136. The packages 136 are stored in magazines 132 as discussed above. The package 136 is positioned at the end of the magazine to allow the printer to print on the label 510 on the product. Once the printing is complete the product is dispensed to the patient.

PDA Prescription Entry Program

The PDA Prescription Entry System allows new prescription entry using personal defaults, new prescription entries needing customization, new pediatric prescriptions, viewing, revising or deleting prescriptions already written, and revising a prescription when the insurance denies the prescription. The entry system is operated using the control buttons on the bottom edge of PDA 4300. As shown in FIGS. 23-30, PDA 4300 includes a back button 4310, a tab button 4320, a scroll button 4330, an enter button 4350, and a cancel button 4340. Tab button 4320 is used to tab between screens. Cancel button 4340 is used to cancel or go back one field. Scroll button 4330 is a bi-directional button and is used to scroll up and down. Enter button 4350 is used to enter and to move to the next field. A hotsync button on the PDA cradle is used to provide a hotsync between the PDA 4300 and another device.

FIGS. 23-30 show exemplary screens of one embodiment of the PDA Prescription Entry Program. Although shown on a PDA, in one or more embodiments, the following system can also be incorporated into a laptop or desktop computer.

Figure 23A:
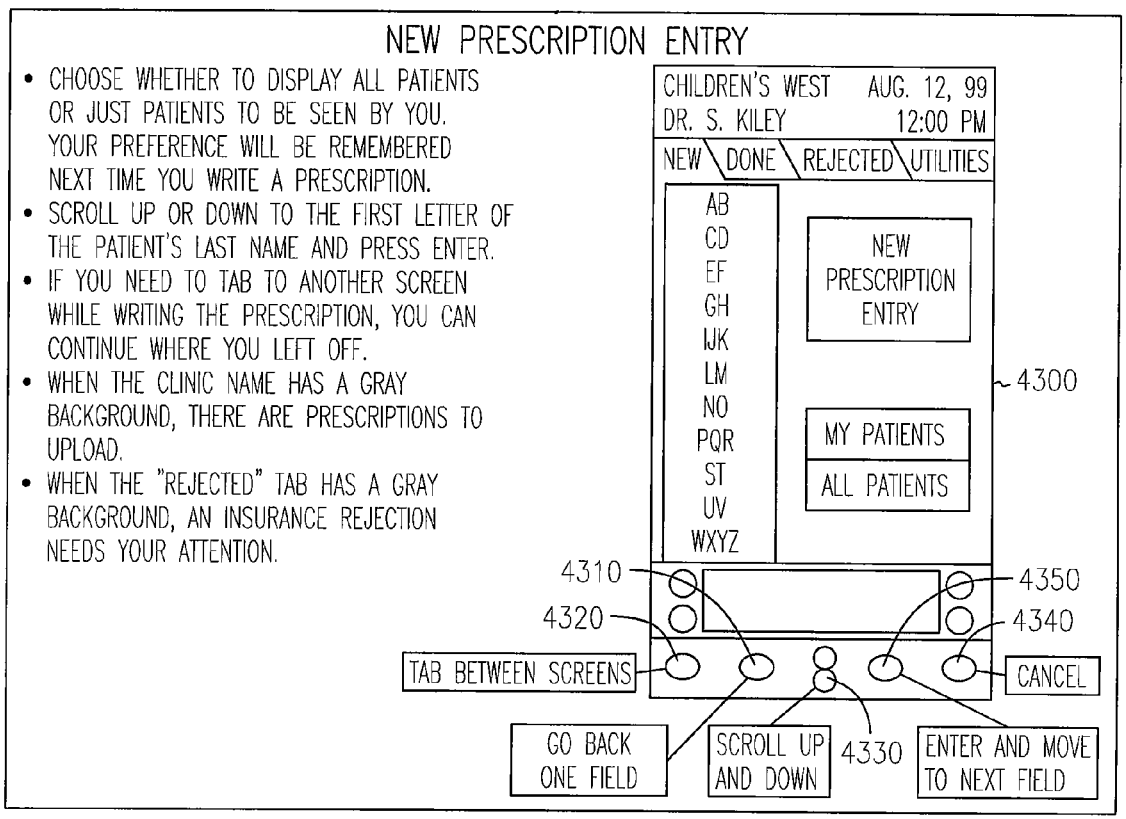
FIGS. 23-30 are screen views of one embodiment of a prescription entry system for a handheld computing device.

FIG. 23A shows an exemplary screen for new prescription entry. The user chooses whether to display all patients or just patients to be seen by the user. The preference is stored for the next time a prescription is written. The user scrolls down using scroll button 4330 to the first letter of the patient's last name and presses enter button 4350. The user optionally may tab to another screen while writing the prescription and return later to finish the prescription at the point where the user left off. When the HCF name 4360 has a gray background, there are prescriptions to upload. When the rejected tab 4370 has a gray background an insurance rejection has been received.

Figure 23B:
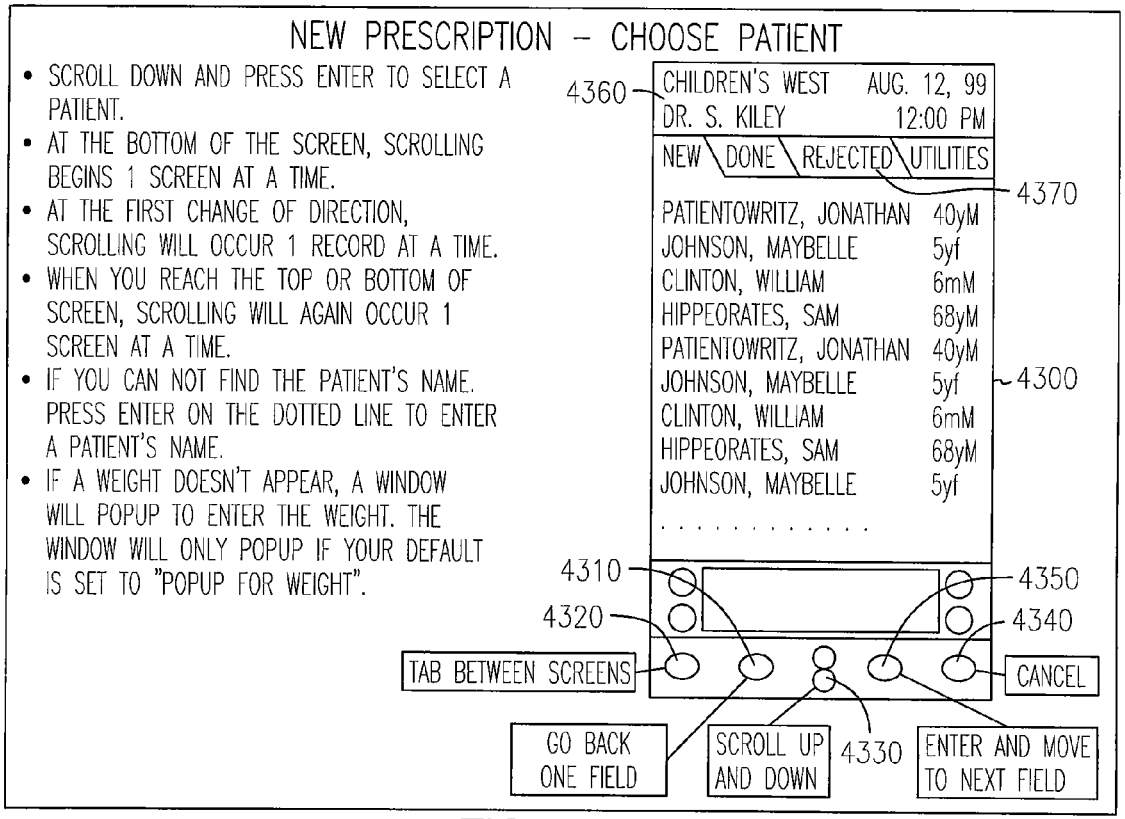
Figure 24D:
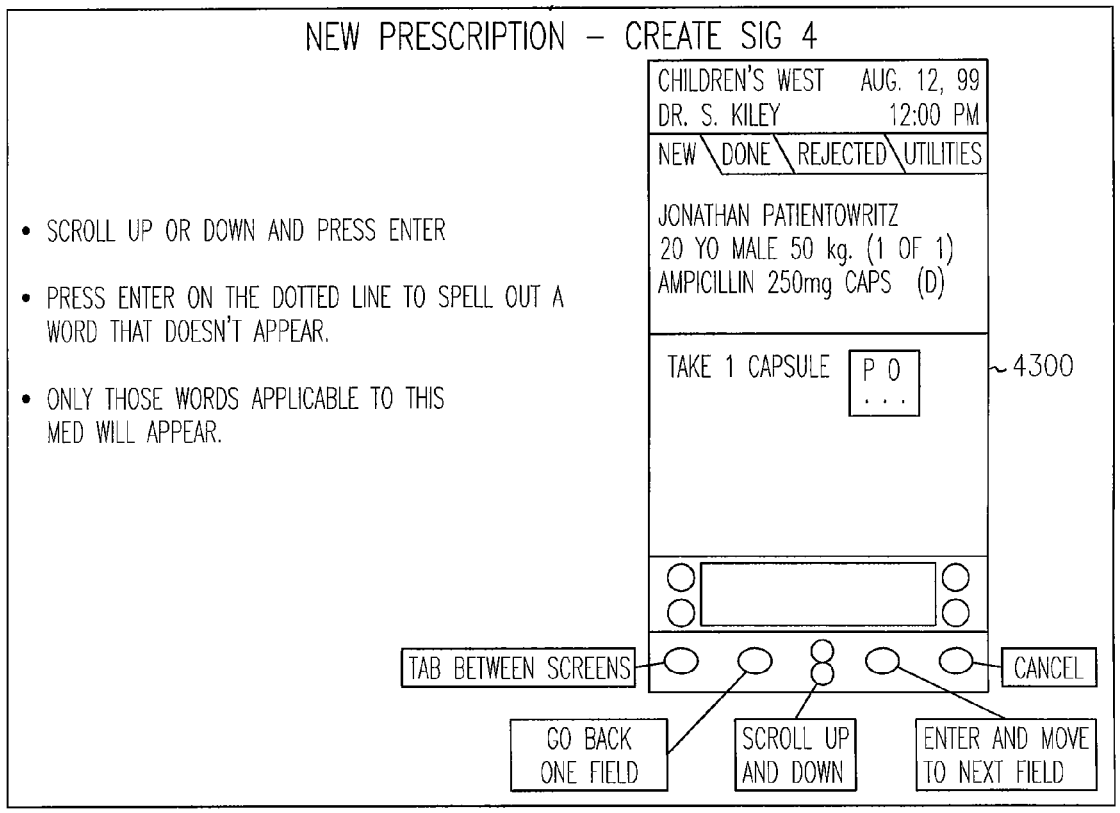
Figure 24E:
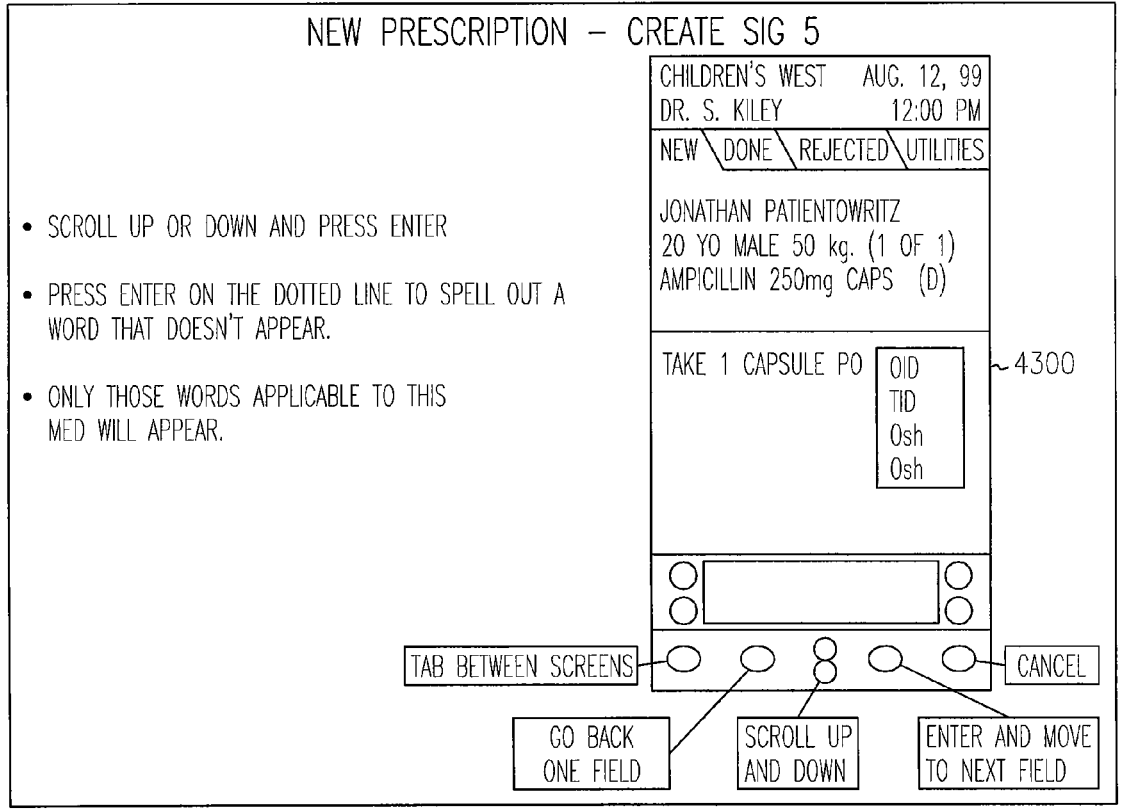

FIG. 23B shows an exemplary screen for choosing a patient for a new prescription. The user scrolls through a patient list using scroll button 4330 to select a patient name. At either the top or the bottom of the screen scrolling begins one screen at a time. At the first change of direction, scrolling begins one patient name at a time. A new patient's name may be entered by pressing enter button 4340 on the dotted line.

If pediatrics mode is toggled on, the program defaults to pop up a window to enter the weight if the weight is not shown. For example, at screen 23D, the user can be given a choice between pediatrics calculation mode or regular mode. If regular mode is chosen the program goes to screen 23E and a default prescription is shown. If pediatrics mode is chosen the program goes to screen 28E.

FIG. 25C shows an exemplary screen for picking a quantity for a new prescription. The user uses scroll button 4330 to scroll down to pick a quantity from the list of quantities. Optionally, the quantities are listed in the order of those most commonly written. The list includes a designation, such as a "D" after those quantities available in the remote dispenser. In one example, a "+" sign denotes that the product is in the dispenser and a "−" denotes that the product is usually in the dispenser, but is out of stock. Blank means the product was not ever in the dispenser. The cursor automatically highlights the closest larger quantity available based on the dosage and length of time to take the medication entered by the user. Optionally, the user may highlight a different quantity or enter a new quantity by pressing the enter key when the dotted line is highlighted.

Figure 25F:
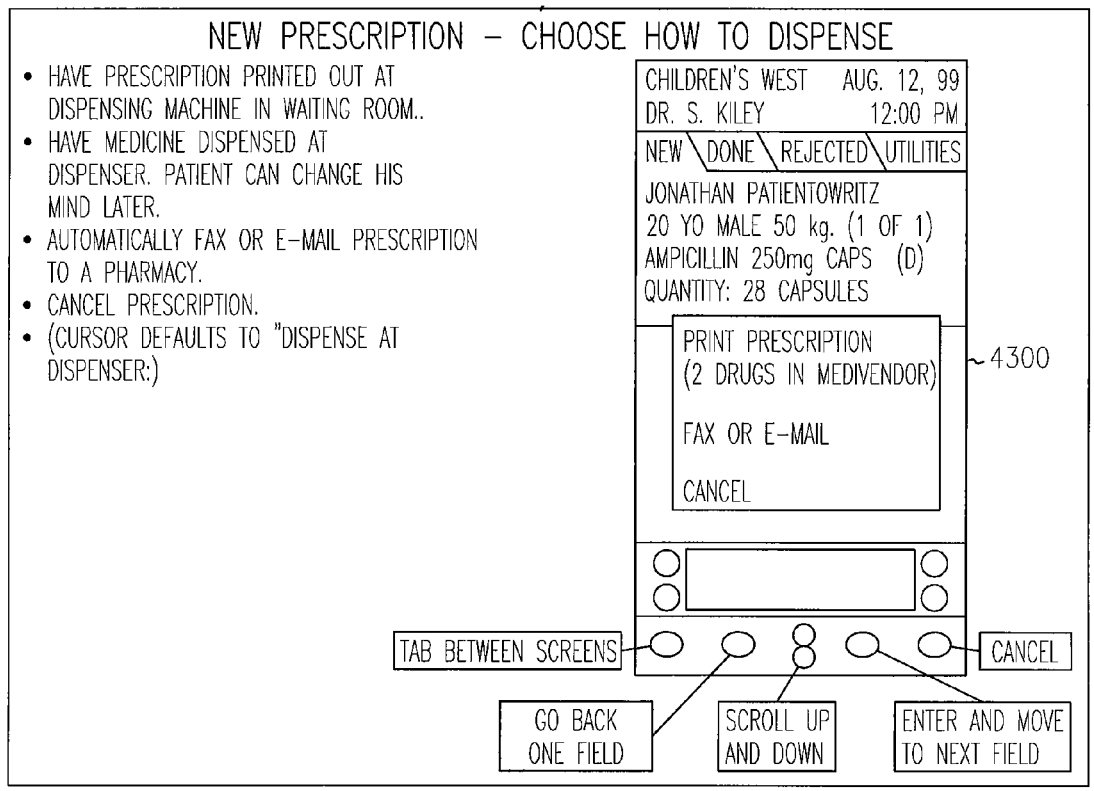
Figure 26A:
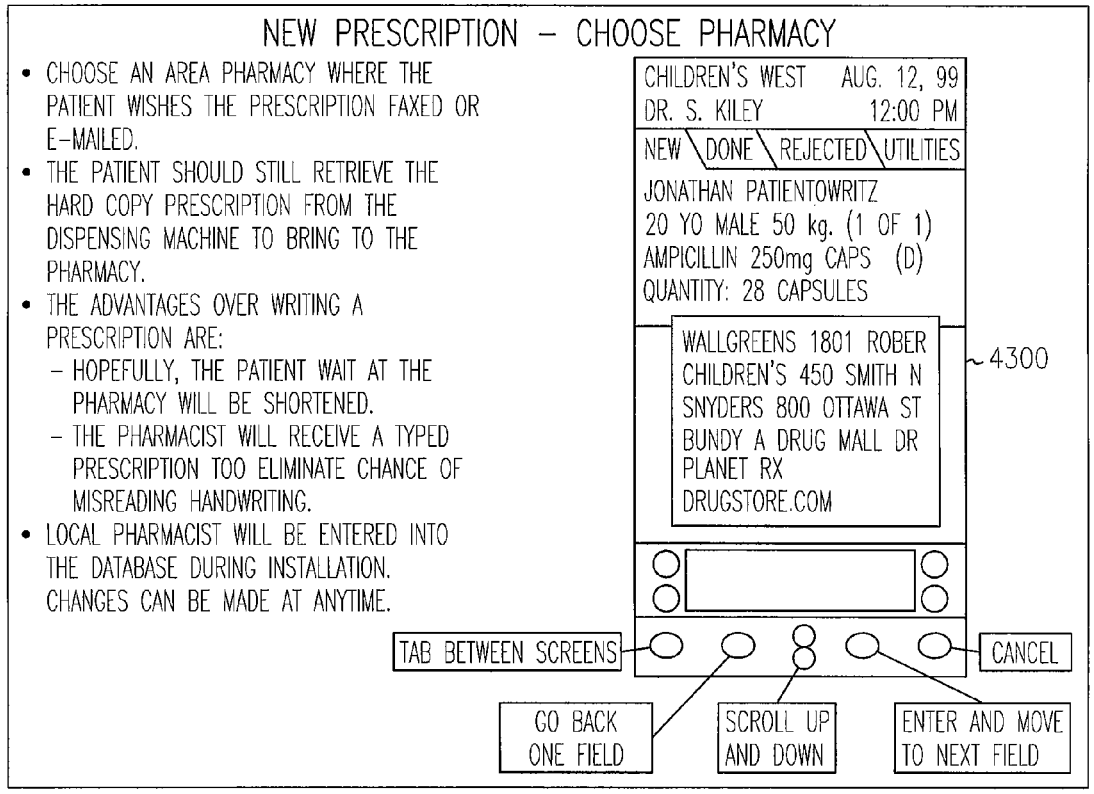
Figure 26B:
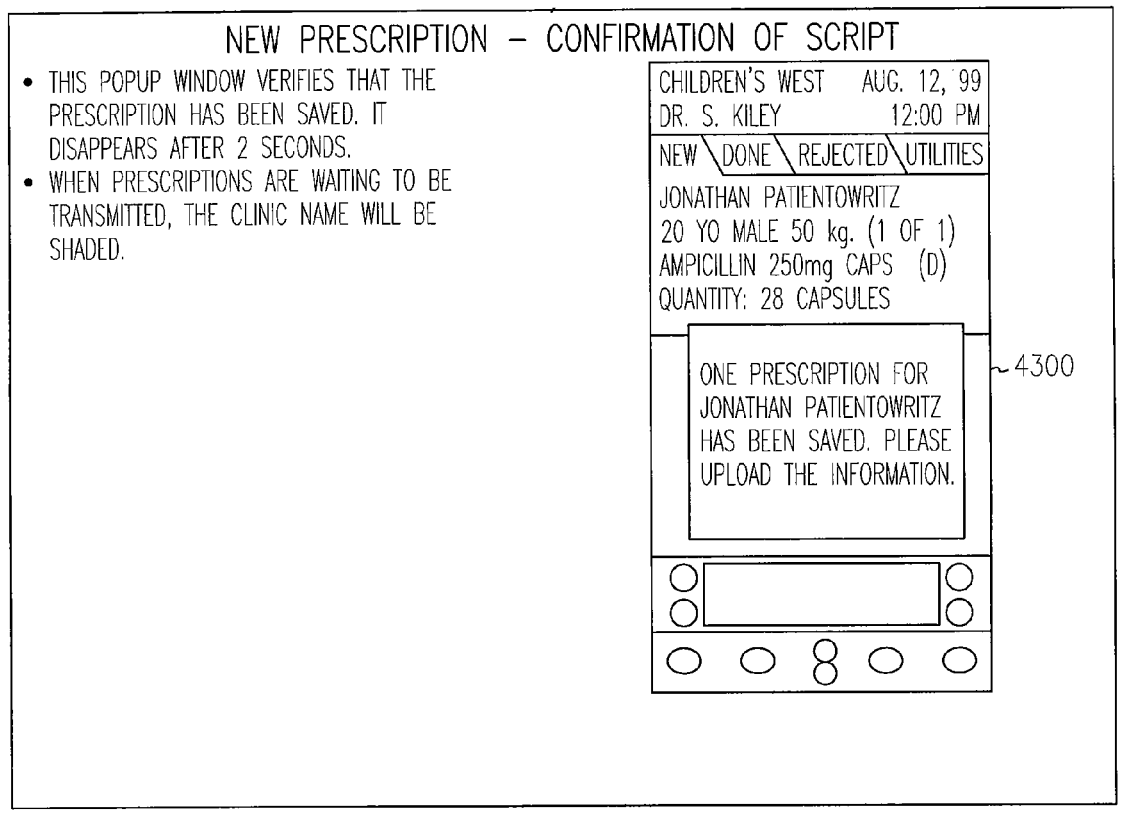
Figure 26C:
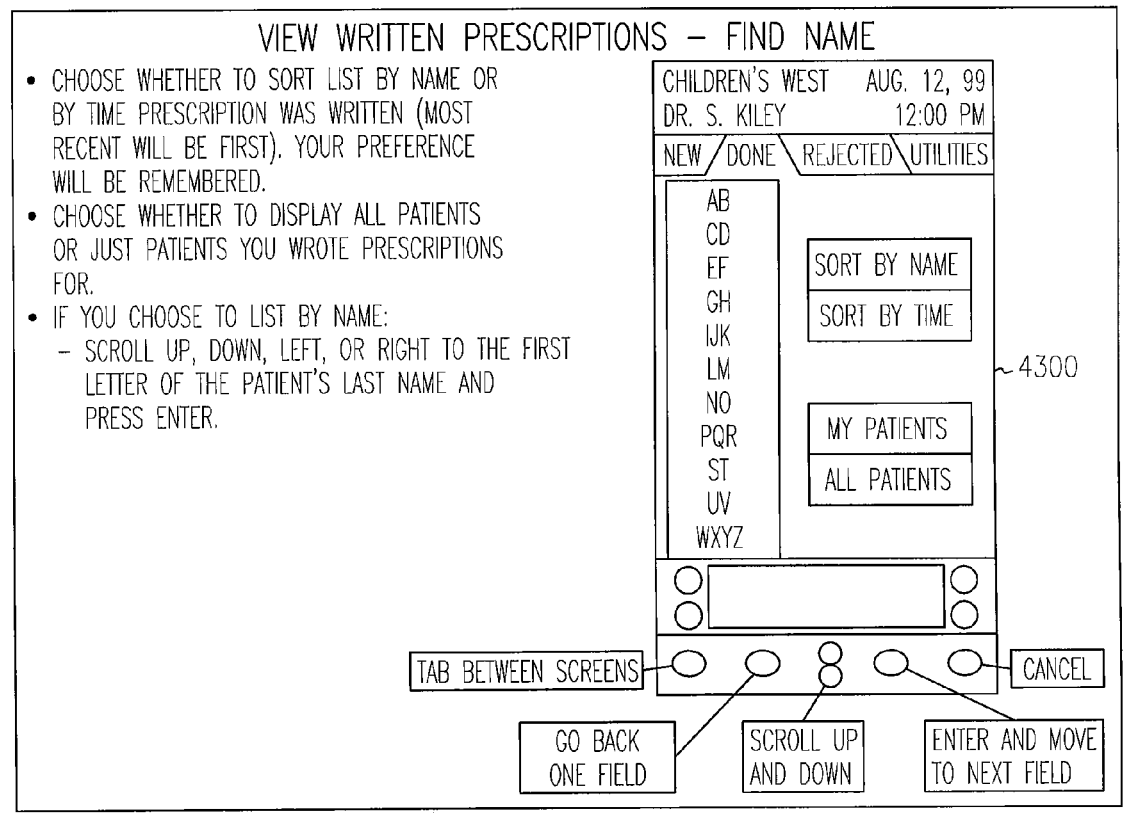
Figure 26D:
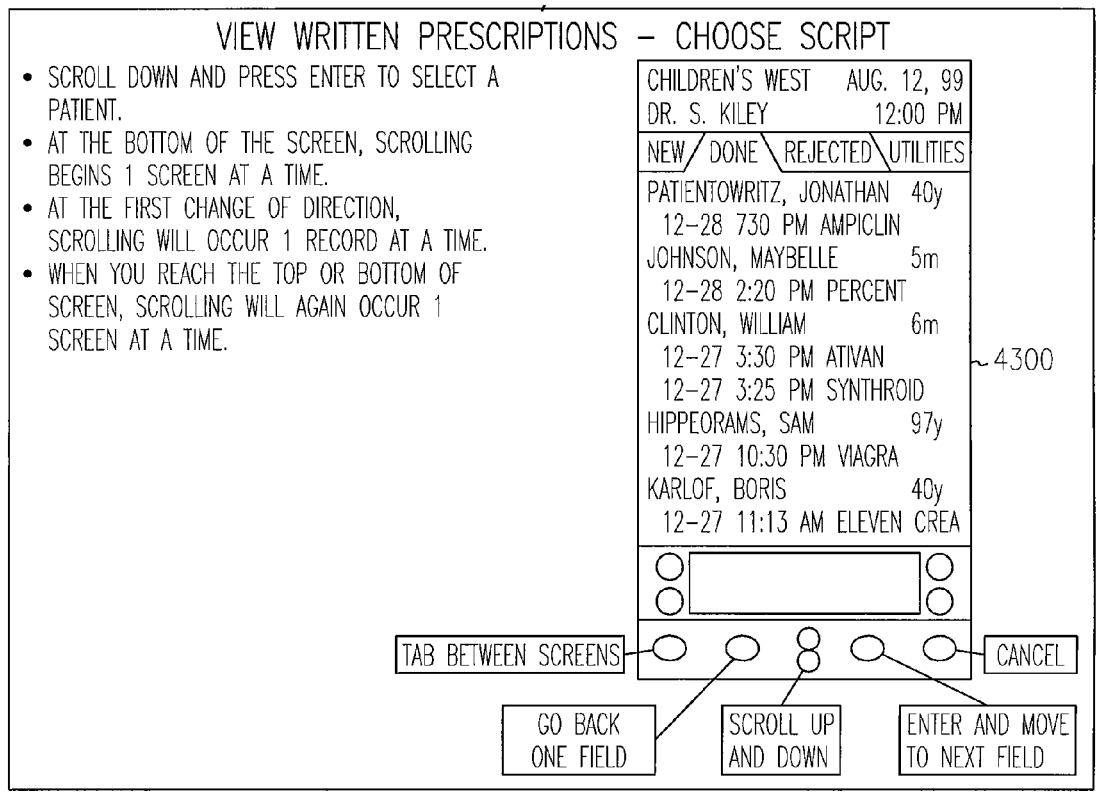
Figure 26E:
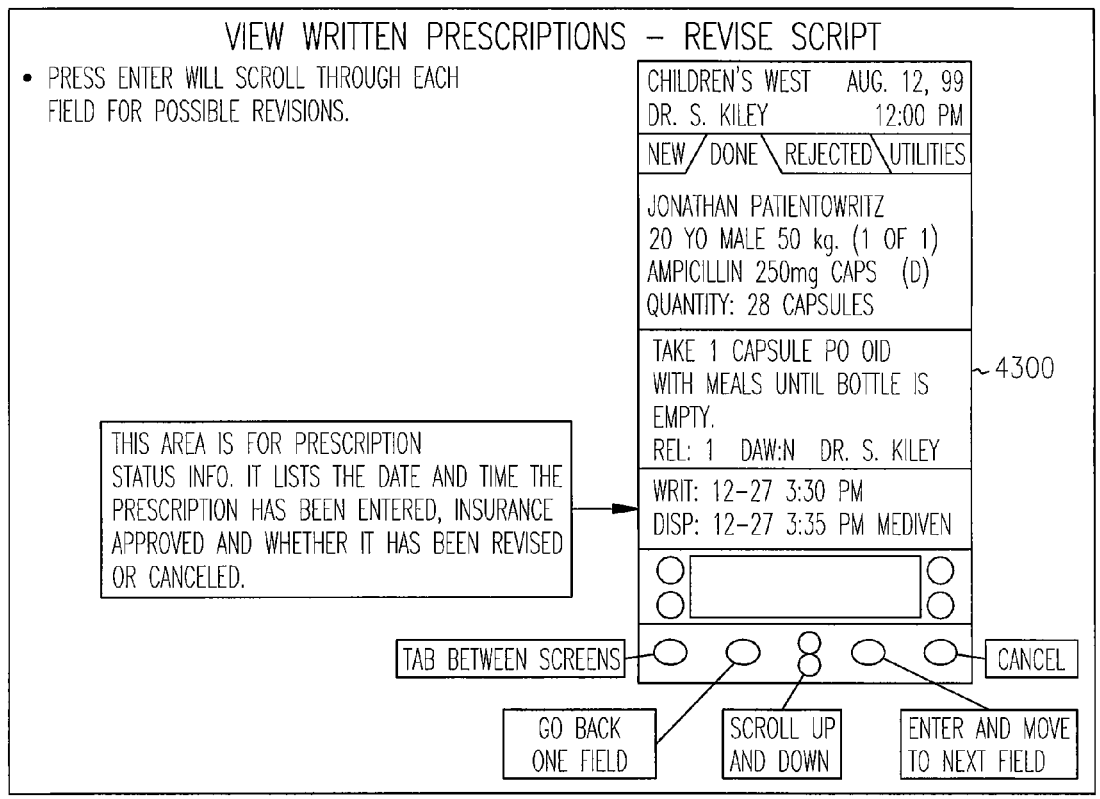
Figure 26F:
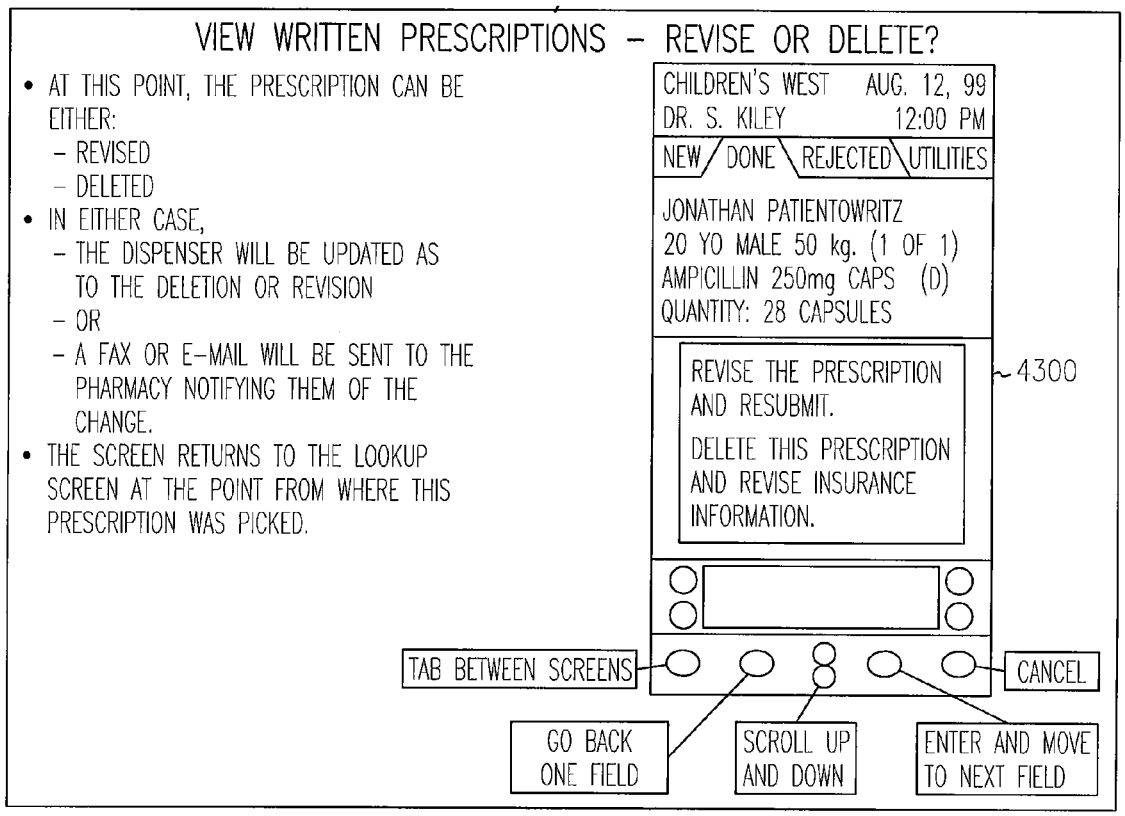
Figure 27A:
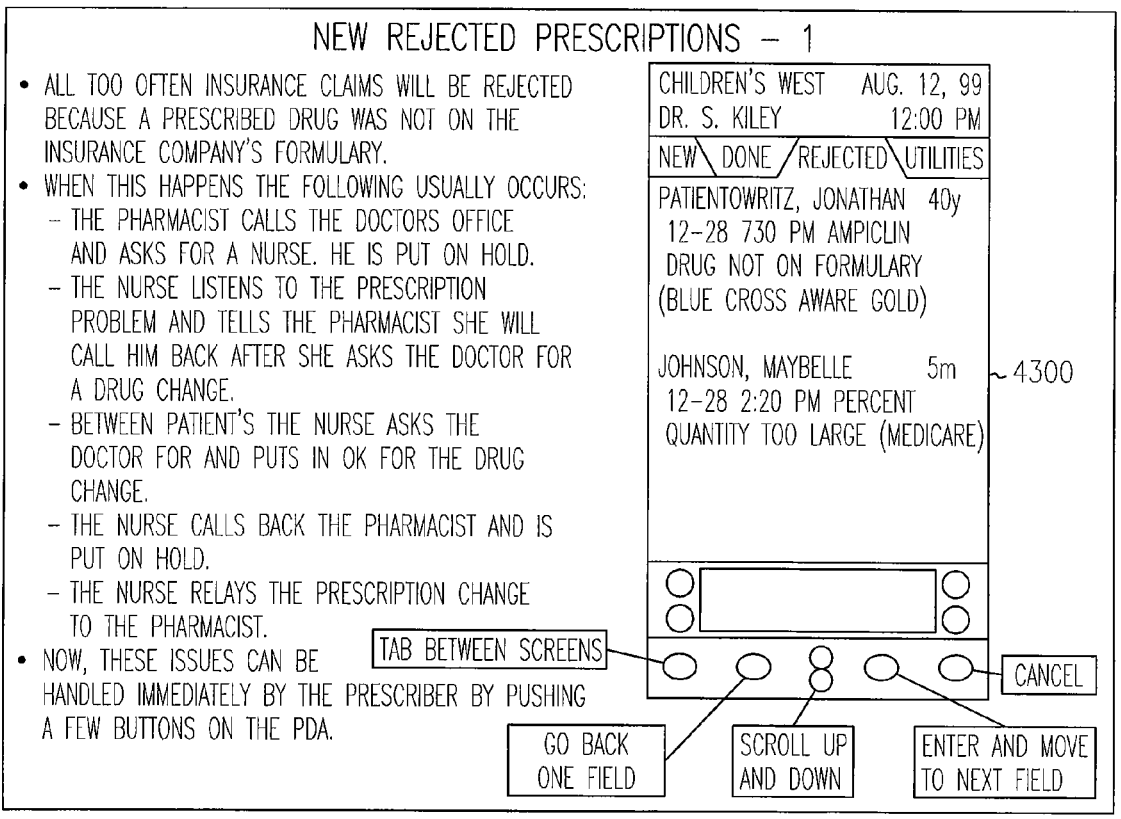
Figure 27B:
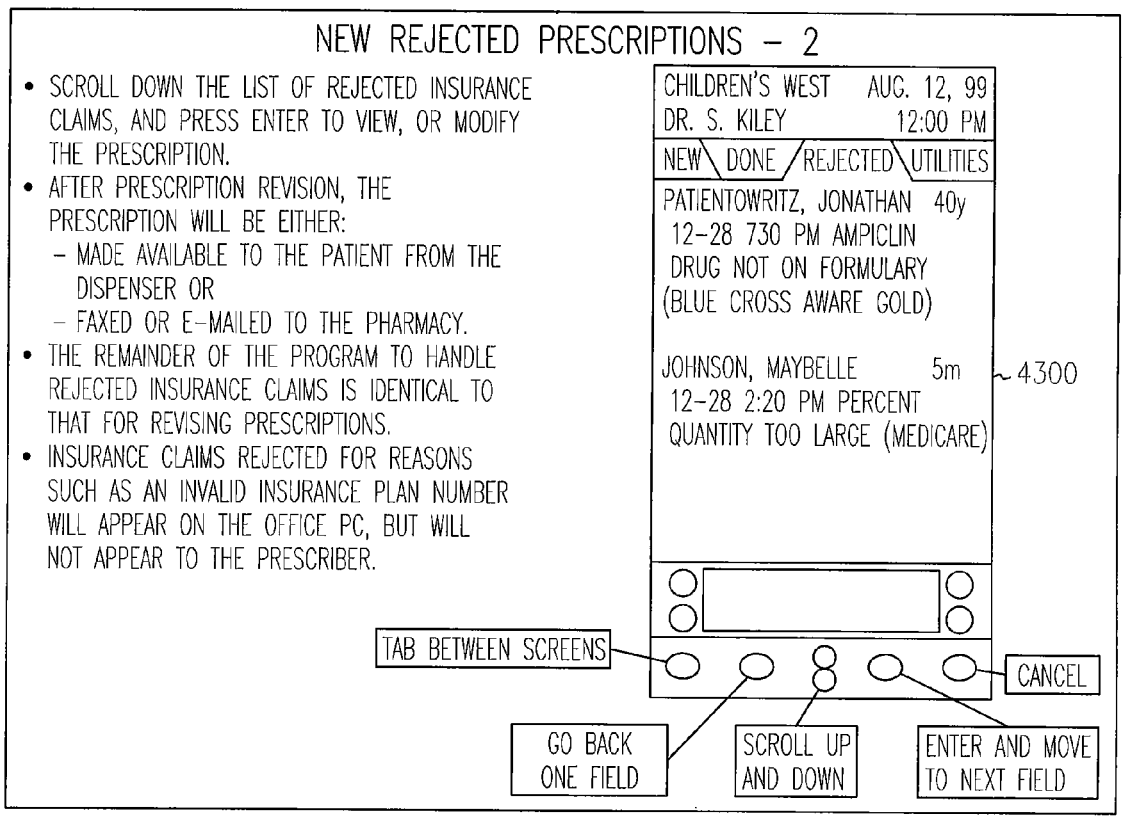
Figure 27C:
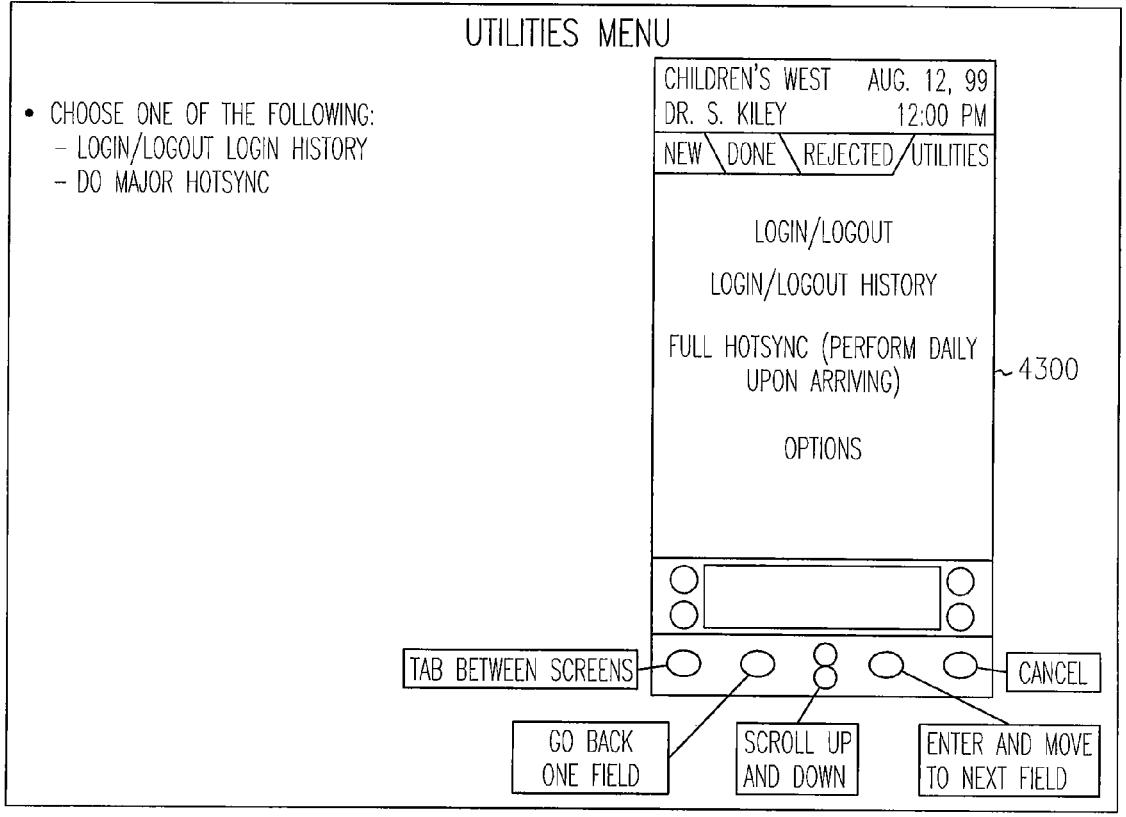
Figure 27D:
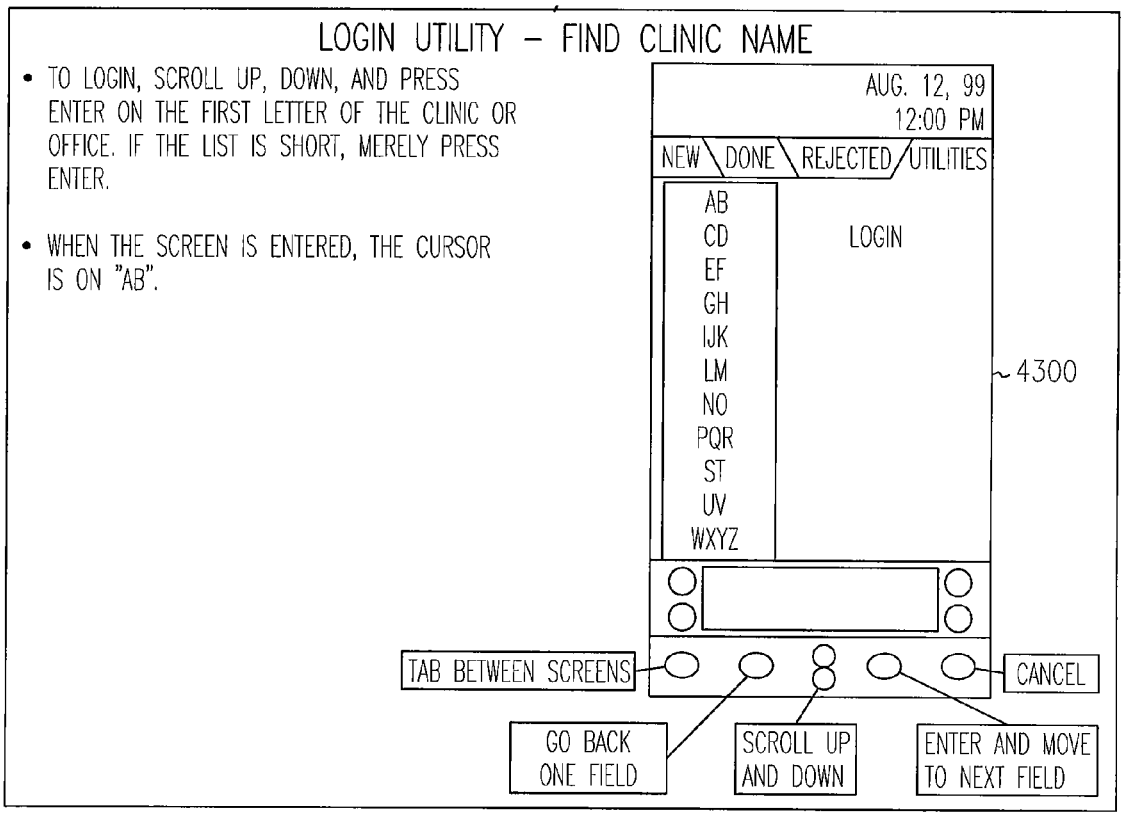
Figure 27E:
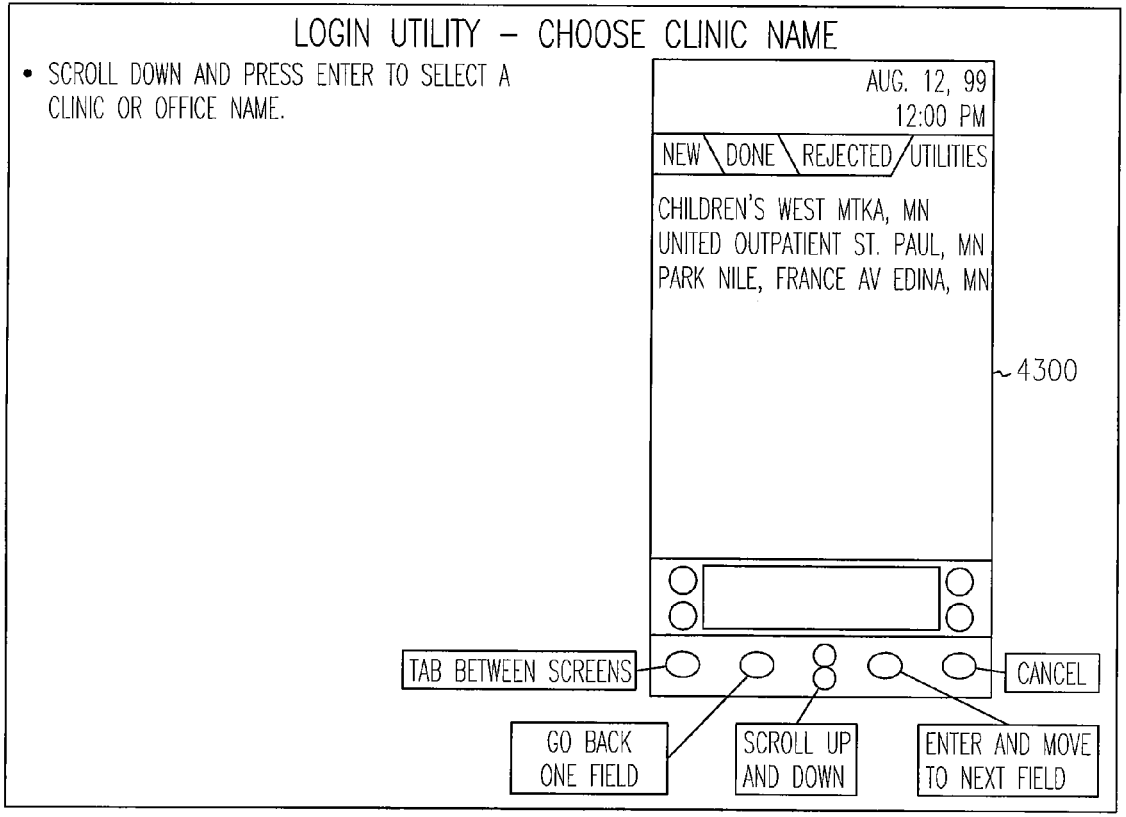
Figure 27F:
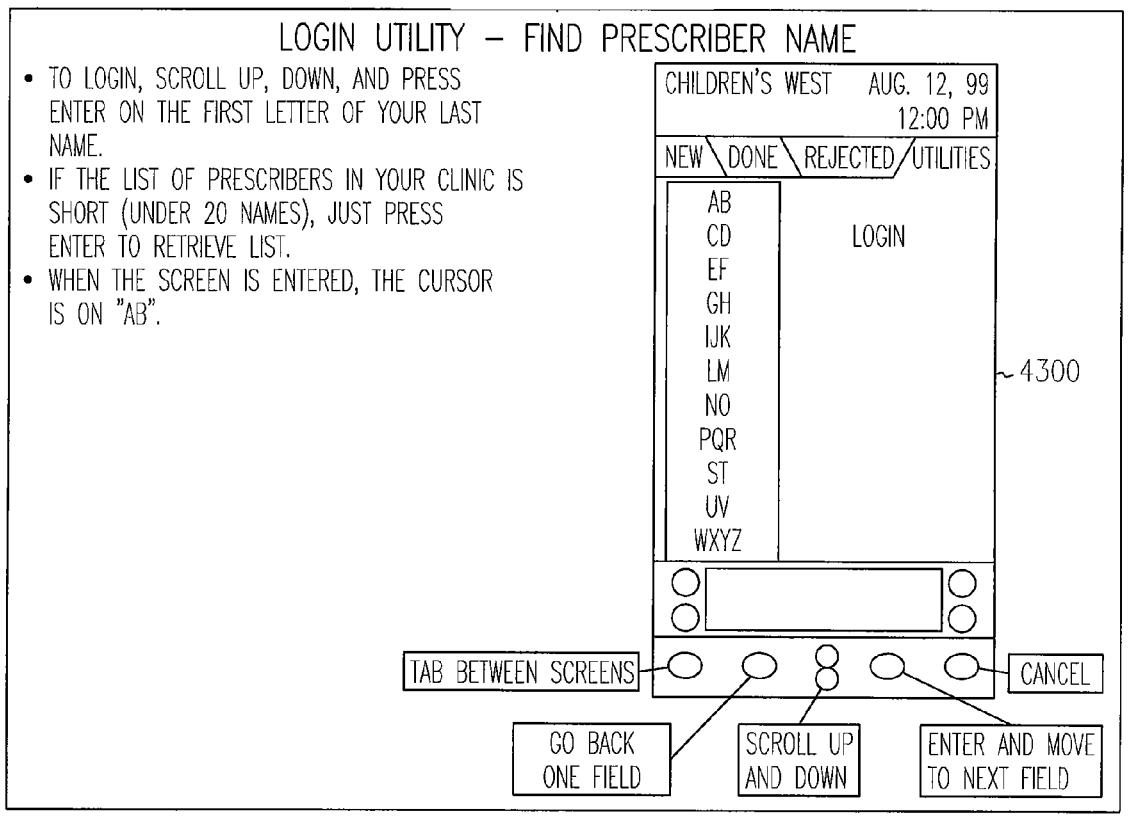

FIG. 25F shows a screen for choosing how to dispense the prescription. The user may choose between having a written prescription printed out at the dispenser in the waiting room, a dispenser at a remote location, or have the prescription drugs dispensed at the remote dispenser, automatically fax or e-mail the prescription to the patient's pharmacy, or completely cancel the prescription.

Figure 28A:
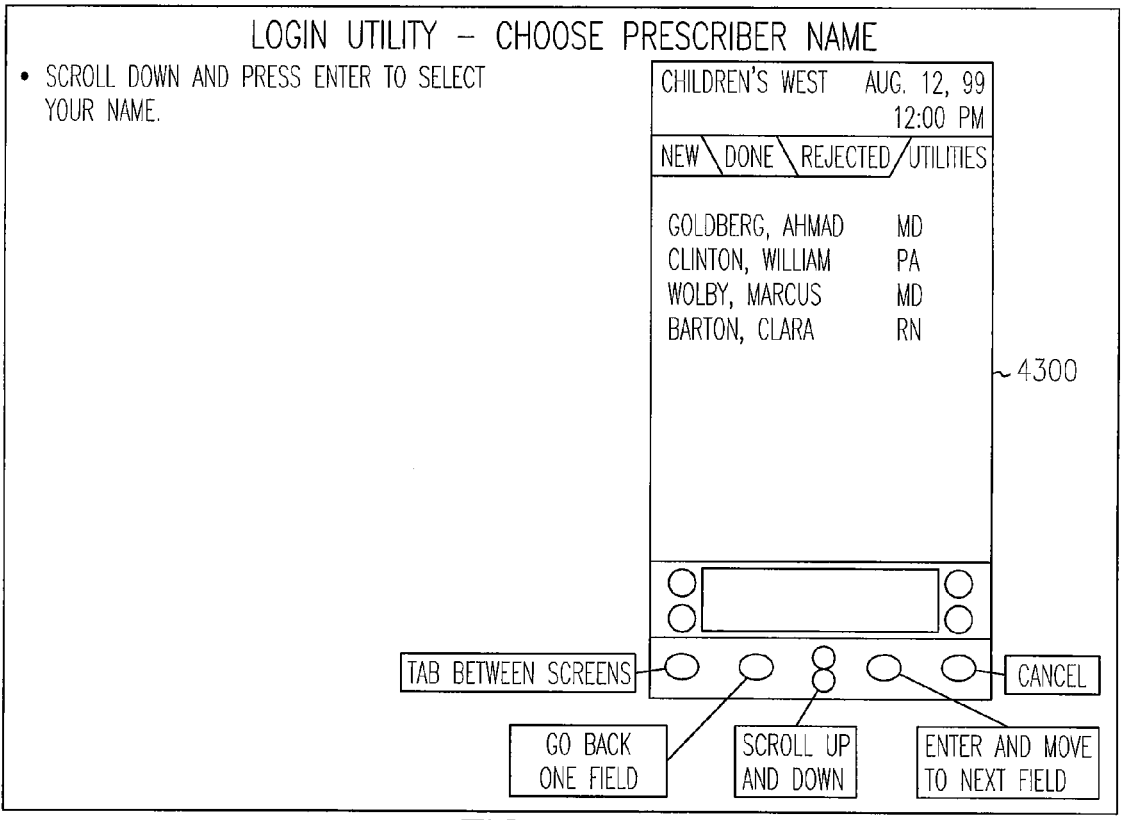
Figure 28B:
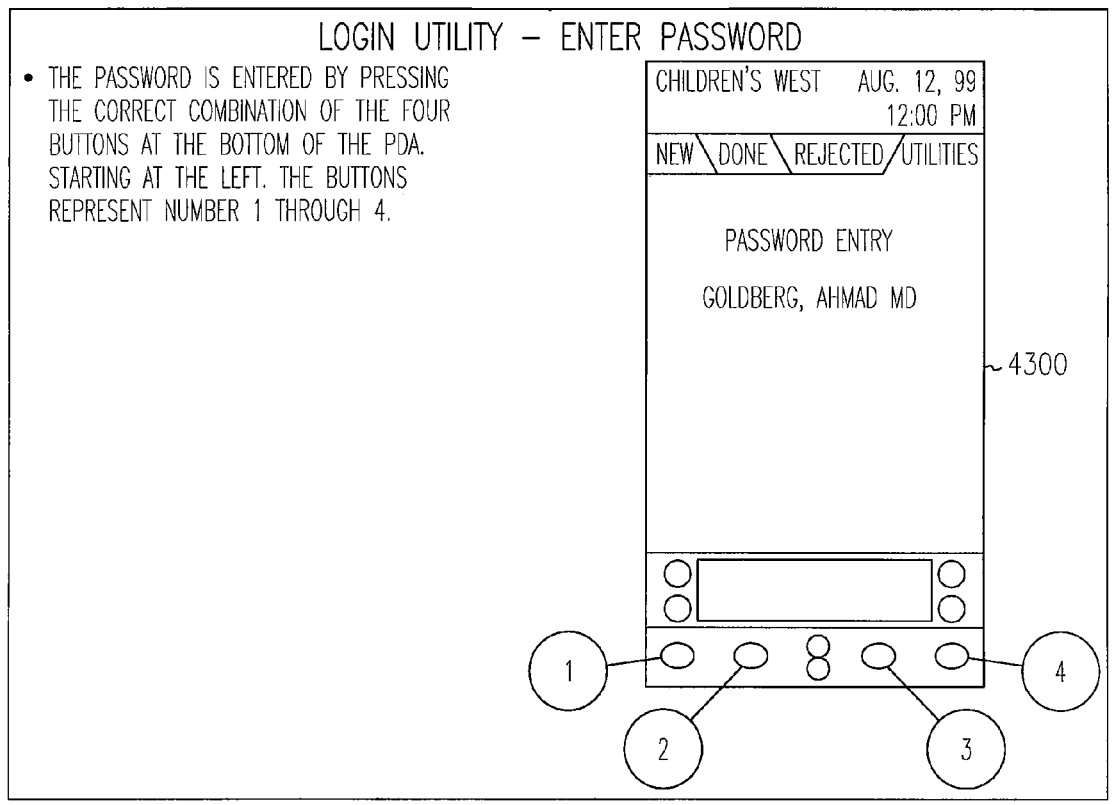
Figure 28C:
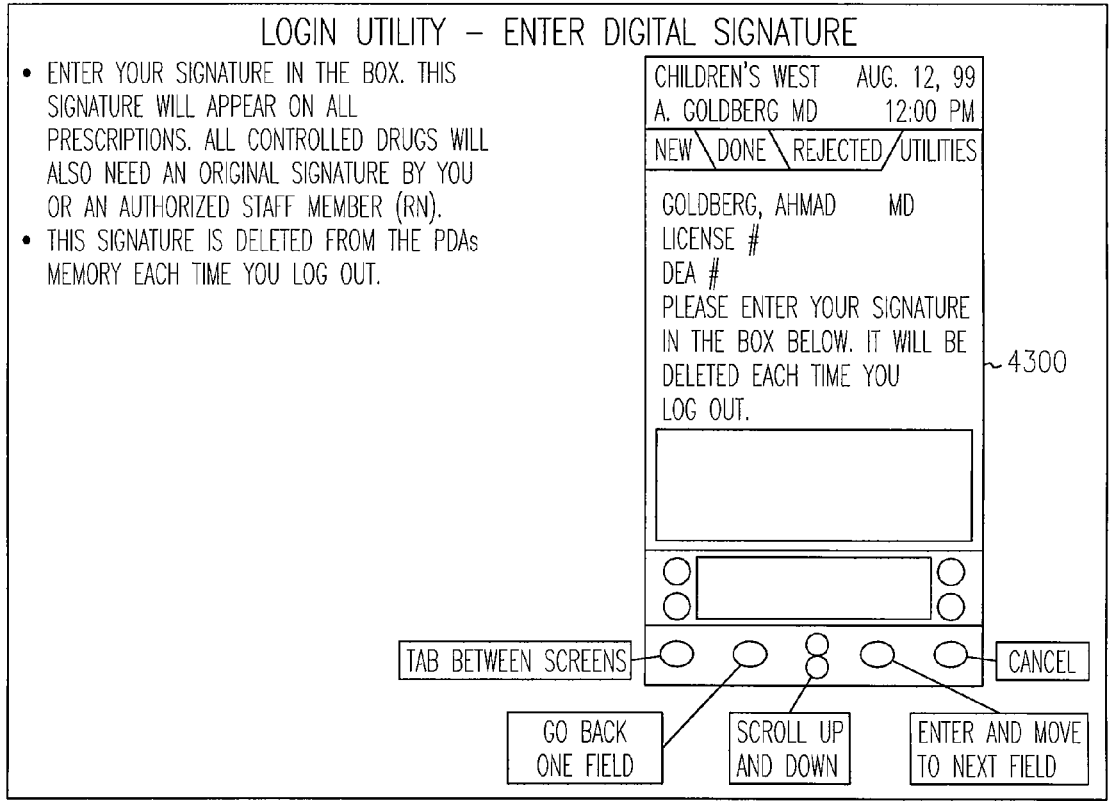
Figure 28D:
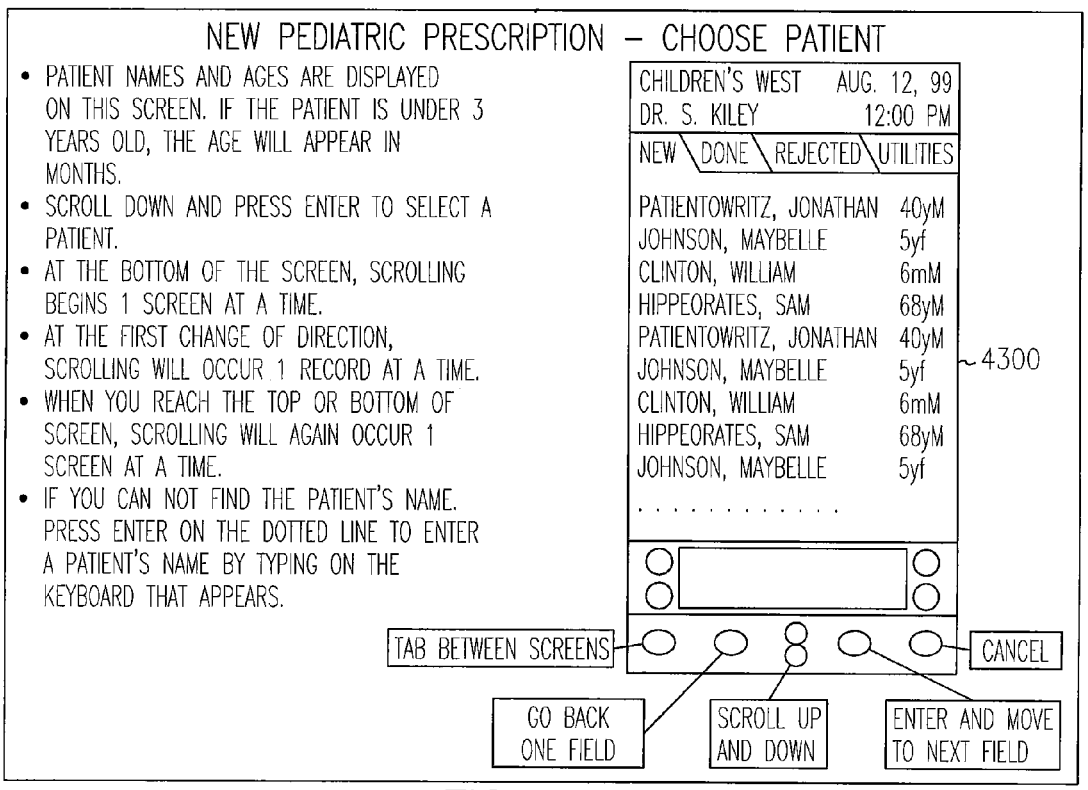
Figure 28E:
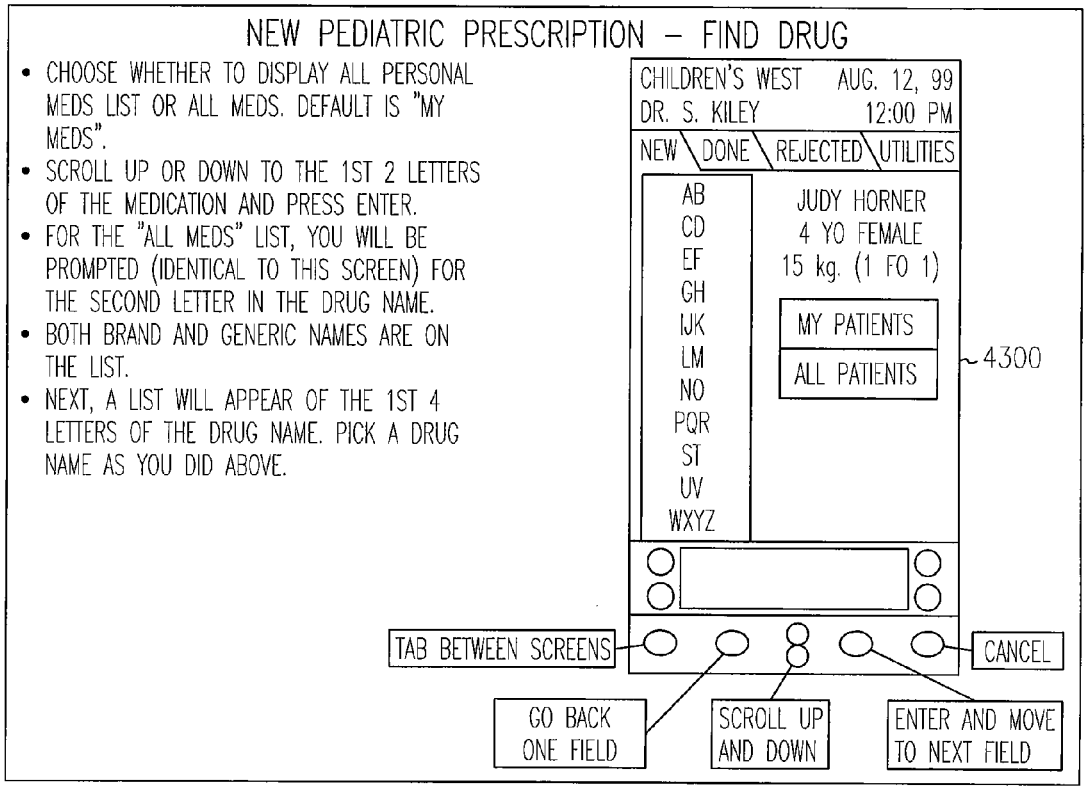
Figure 29D:
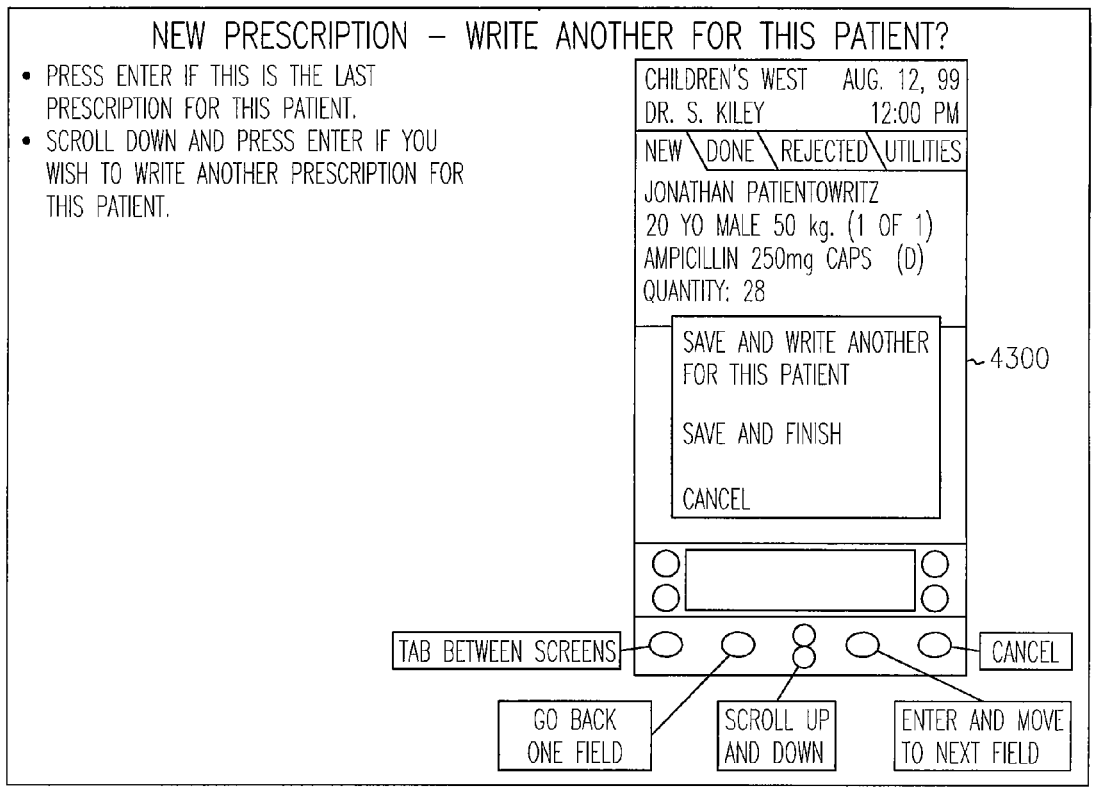
Figure 29E:
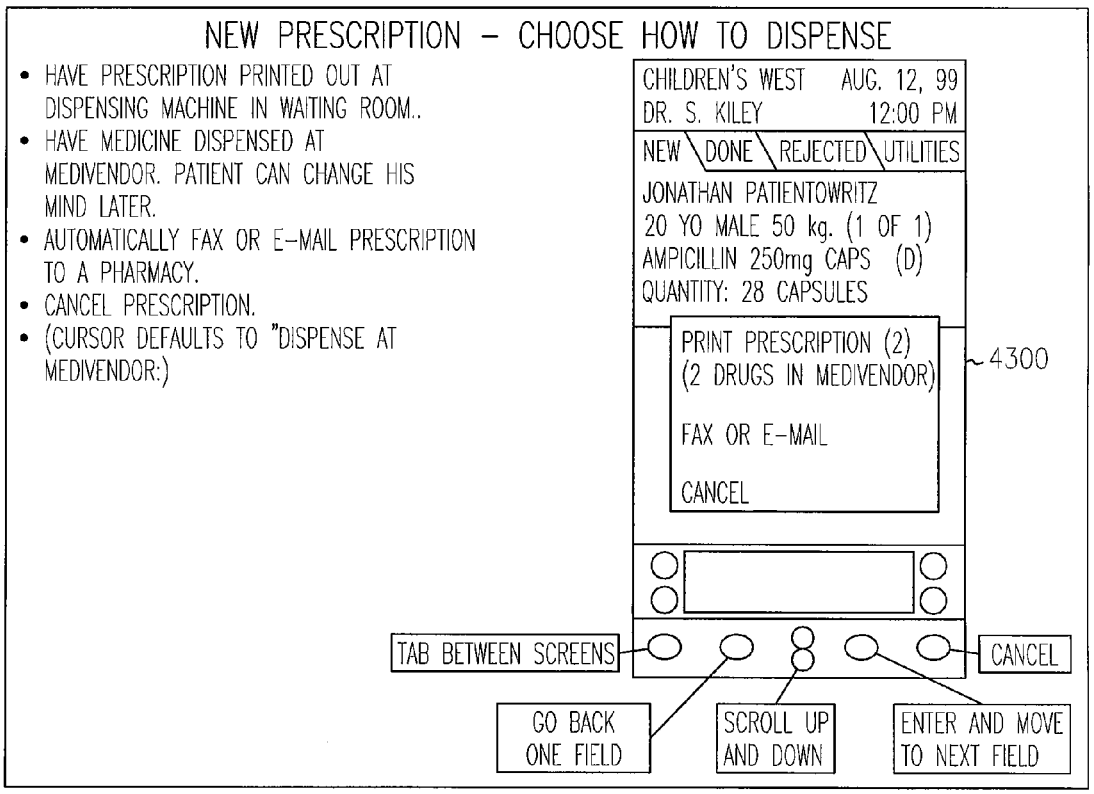
Figure 29F:
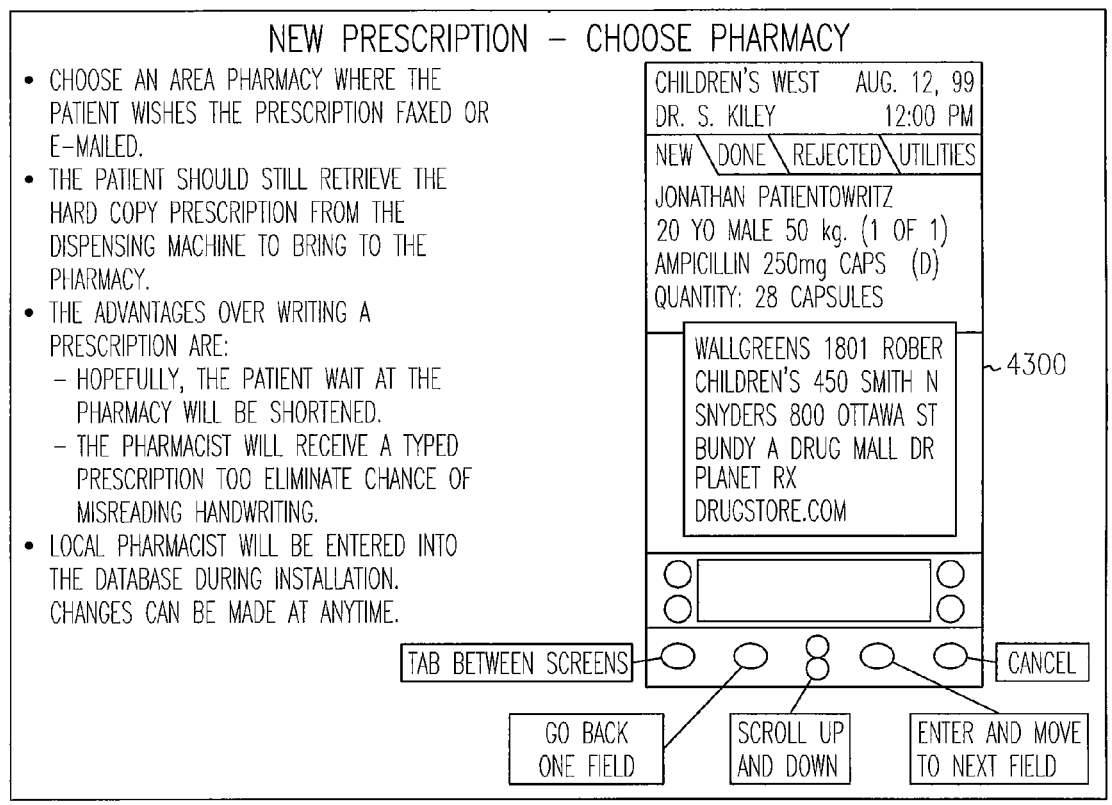
Figure 30:
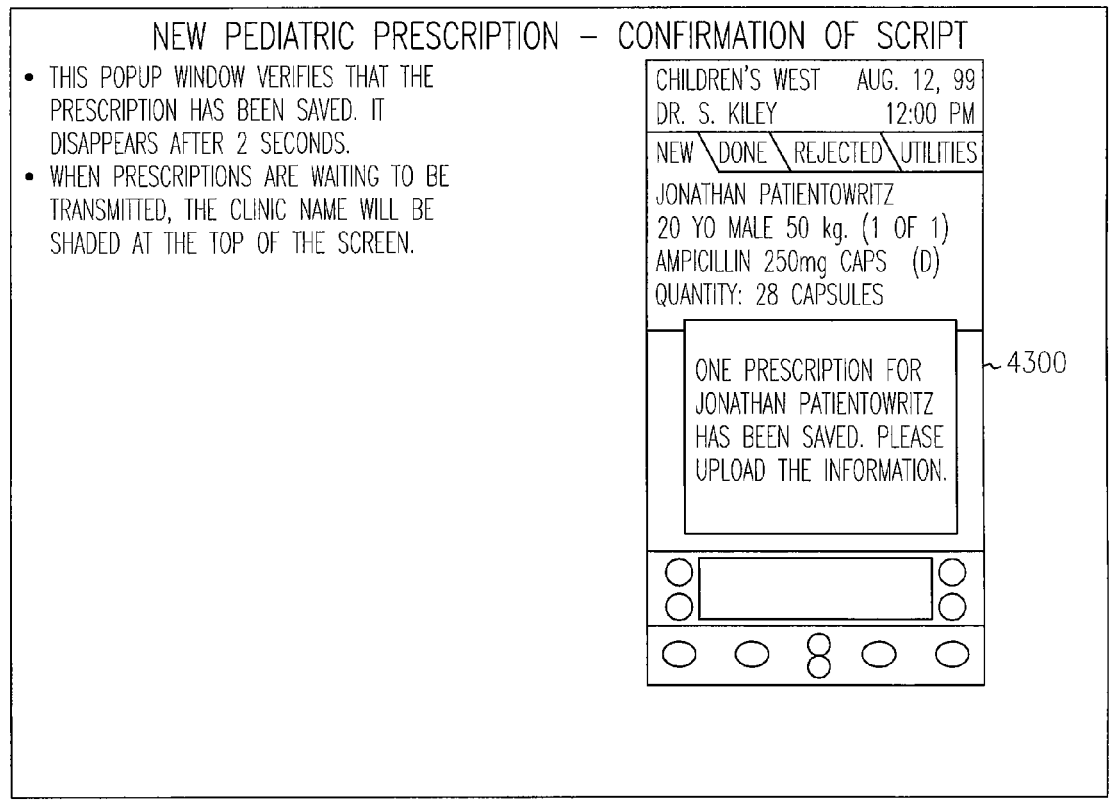

FIG. 28F and so on show one embodiment of pediatrics calculations mode. As noted above, in this mode the prescriber will be prompted to enter the patient's weight. After that, the daily dose is selected. As the prescriber adjusts the daily dosage, the system automatically calculates the exact dosage (in units per day). The prescriber then chooses the form and strength of the drug (if the prescriber selects a dose that exceeds the maximum recommended dose/m/k/day, they will be prompted to answer a question confirming their interest in selecting that dose. The prescriber then chooses the prescription instructions.

All these examples shown allow a user to write a prescription without using any writing input into the PDA (for example using the "Graffiti" text input function on a Palm PDA). The user can write a complete prescription just using the buttons on the bottom of the PDA to find and select the proper values for various parameters. This allows quick and painless prescription preparation. Also, the user does have the option of "graffiti" writing in some values if they want to make a change.

Additional Embodiments

Figure 31:
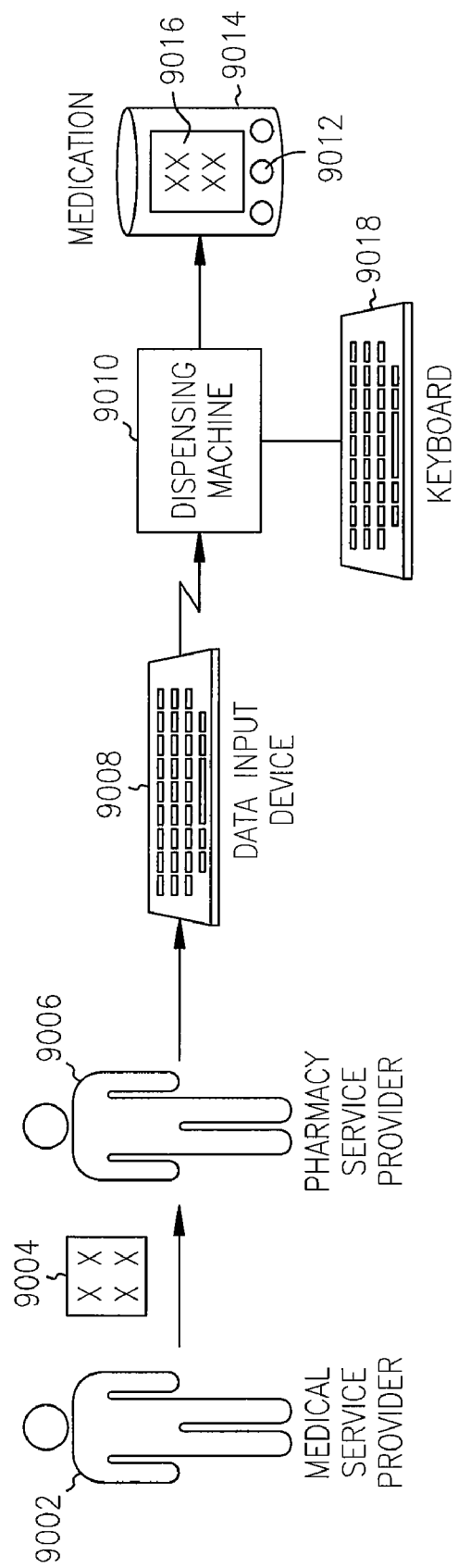
FIGS. 31-47 illustrate additional embodiments of systems, methods and configurations for use of medication dispensing machines according to the present invention.

Referring now to FIG. 31 there is illustrated still another example embodiment of a method according to the present invention. In this embodiment, a medical service provider 9002 prescribes a medication for a patient. Such prescription may be conveyed from the provider 9002 to a pharmacy service provider 9006 either as written instructions on a paper slip 9004, called into the pharmacy service provider 9006 by the provider 9002, or otherwise conveyed such as by facsimile or using an electronic medium like e-mail or other electronic transfer. The prescription is thus presented to the pharmacy service provider 9006 in oral or written (paper or electronic) form. The pharmacy service provider 9006 then enters data about the prescription into a data input device 9008 that relays the data to a medication dispensing machine 9010, for example, any one of the embodiments described with respect to FIGS. 1-30 hereinabove. The dispensing machine 9010 automatically prepares a medication 9012 by preparing a container 9014 holding the medication wherein the container is automatically labelled 9016 with information specific to the patient by the dispensing machine. Such information typically includes the patient's name and the medication dosing and schedule. Further according to this embodiment, the dispensing machine 9010 is located remotely from the location of the prescribing medical service provider 9002.

According to another example embodiment of this method, the medication is automatically labelled by the dispensing machine 9010 at the time that the patient picks up the medication. In particular, it is labelled after the patient arrives at the location of the dispensing machine. According to another example embodiment, the medication is automatically labelled by the dispensing machine 9010 prior to the time the patient arrives at the location of the dispensing machine to pick up the medication. According to another embodiment, prior to or after arrival at the site of the dispensing machine 9010 the patient is provided with a code (for example an alphanumeric code 4-10 digits long) and the patient enters the code into an input device 9018 on the dispensing machine to obtain the labelled container. In one example, this can happen if a patient calls to request a refill by phone or over the Internet. As discussed above, the user has payment options such as using a check reader, cash, credit, debit cards, insurance, etc. Also, in one example, if the machine is in a store, the user can pick up the dispensed product and pay at a cashier.

Figure 32:
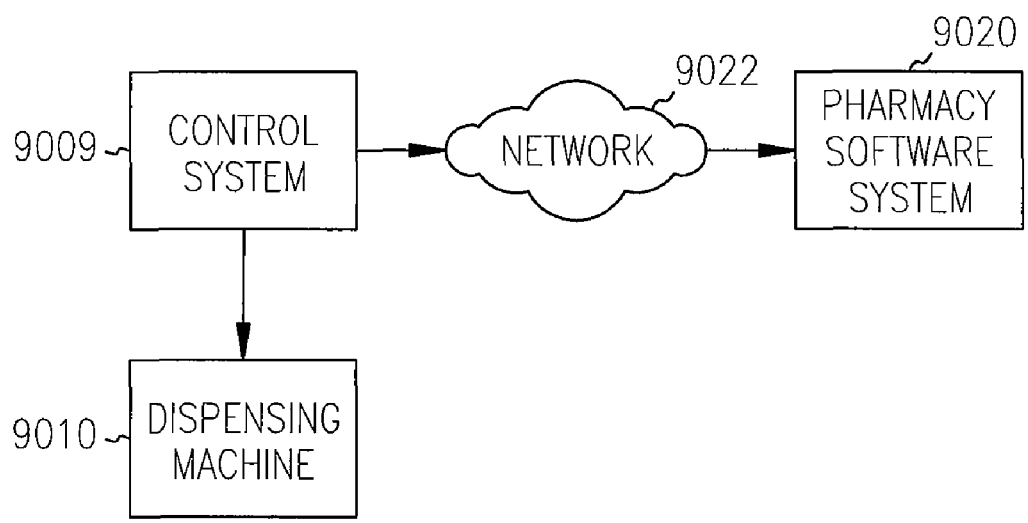

According to still another embodiment shown in FIG. 32, a control system 9009 for the dispensing machine 9010 is networked with a pharmacy management software system 9020 over a network 9022, which may include in part a local area network and a wide area network such as the Internet or a virtual private network, or satellite link, for example but not by way of limitation.

Figure 33:
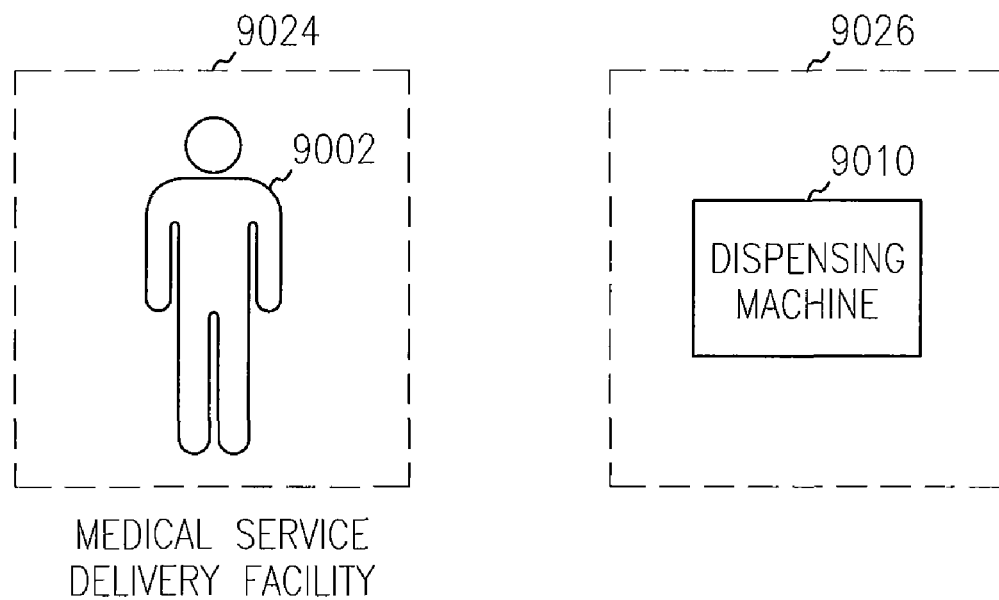

According to another example embodiment as illustrated in FIG. 33, the medical service provider 9002 is located in an HCF or medical service facility 9024, and the dispensing machine is in a location 9026 that is not co-located with the facility or at location 9024. The medical service facility may be, for instance but not by way of limitation, a doctor's office, medical HCF or hospital, and the location 9026 can be a pharmacy located, for example, off-site in the neighborhood or facility complex, or many miles away in a drive thru window or virtually any location.

Figure 34:
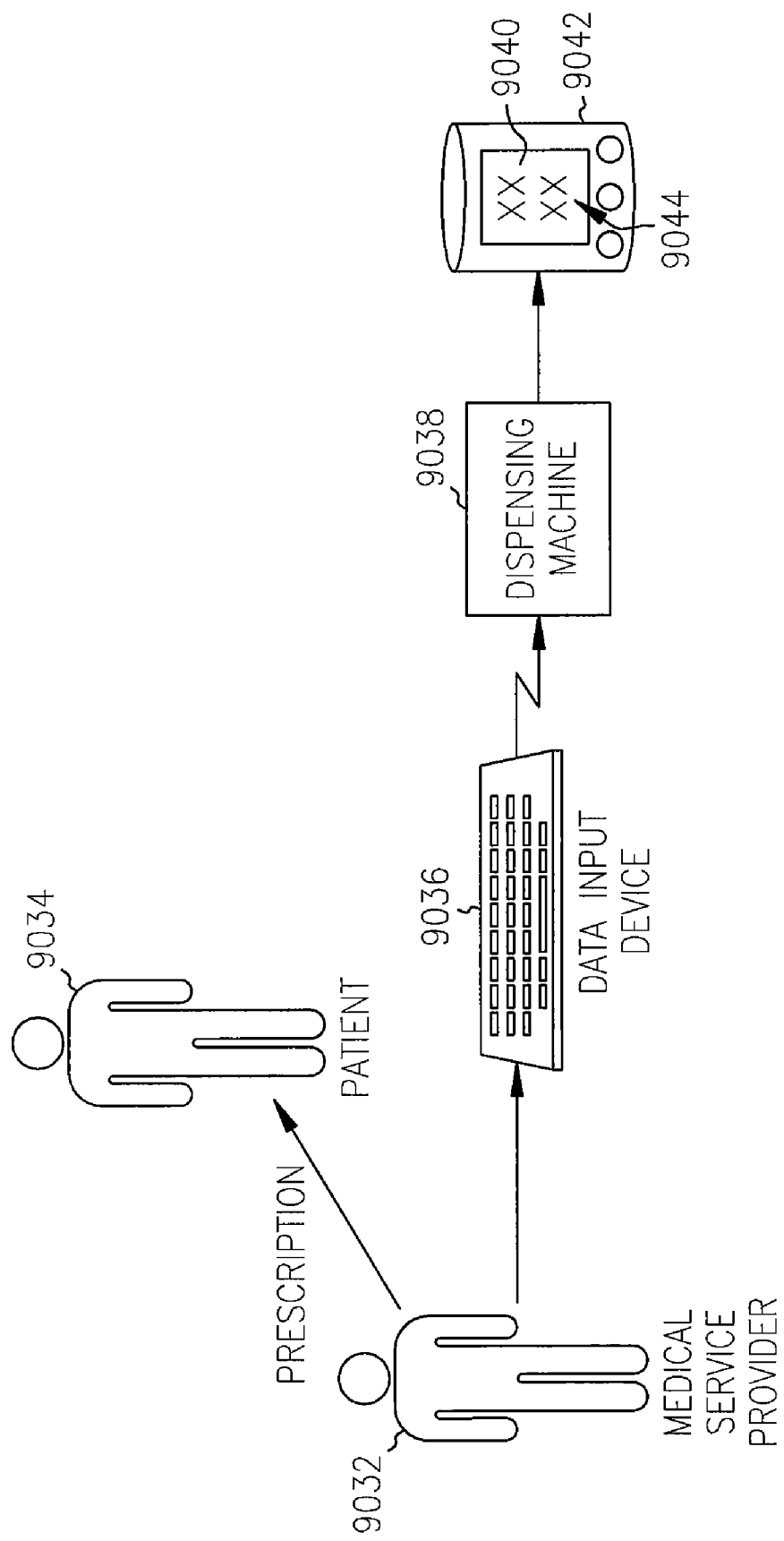

According to still another example embodiment of the invention illustrated in FIG. 34, there is provided a method for dispensing prescribed medications. In this embodiment, a prescribing medical service provider 9032 prescribes a medication for a patient 9034. Data about the prescription is entered into a data input device 9036 that relays the data to a medication dispensing machine 9038, for example, any one of the embodiments as described hereinabove in FIGS. 1-30. In one example, the dispensing machine 9038 can automatically prepare the medication for the patient by labelling 9040 a container 9042 of the medication with patient-specific information 9044. Alternatively, the labeling can take place after the patient enters the proper information and payment (if any) into the dispenser. In this embodiment, the dispensing machine 9038 is located remotely from the location 9036 of the prescribing medical service provider 9032.

Figure 35:
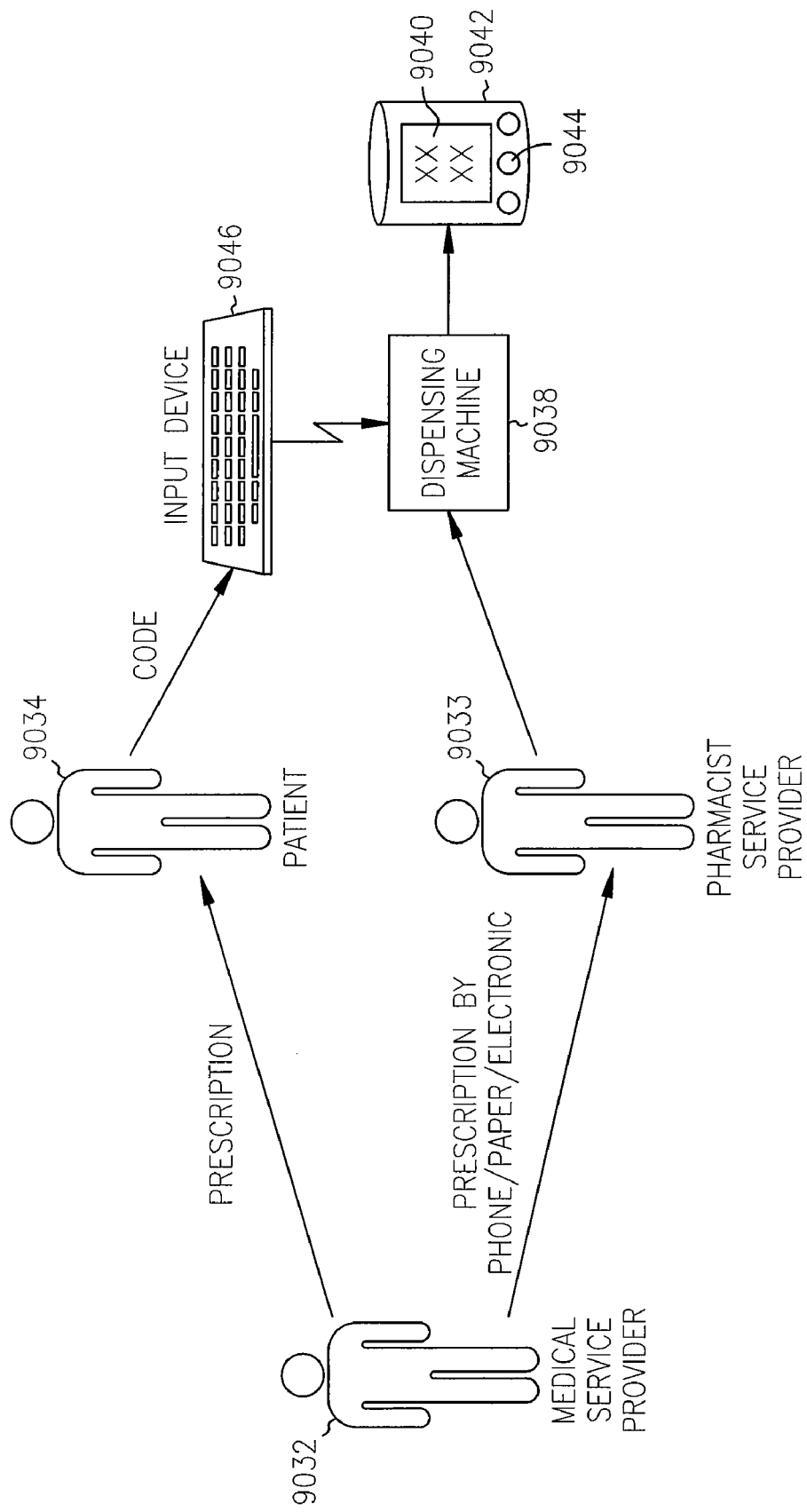

According to one alternate embodiment of the method of FIG. 35, the prescription is presented to the pharmacy service provider 9033 orally over the telephone, in written form by presenting it on paper, or in written form by an electronic delivery mechanism. The pharmacy service provider operates dispensing machine 9038 to enter the prescription.

According to another example embodiment of this method, the medication is automatically labelled by the dispensing machine 9038 at the time that the patient picks up the medication. In particular, it is labelled after the patient arrives at the location of the dispensing machine 9038. According to another example embodiment, the medication is automatically labelled by the dispensing machine 9038 prior to the time the patient arrives at the location of the dispensing machine to pick up the medication. According to another embodiment, the patient is provided with a code (for example an alphanumeric code 4-10 digits long) either prior to or at the time they arrive at the location of the dispensing machine 9038 and the patients enters the code into an input device 9046 on the dispensing machine to obtain the labelled container.

Figure 36:
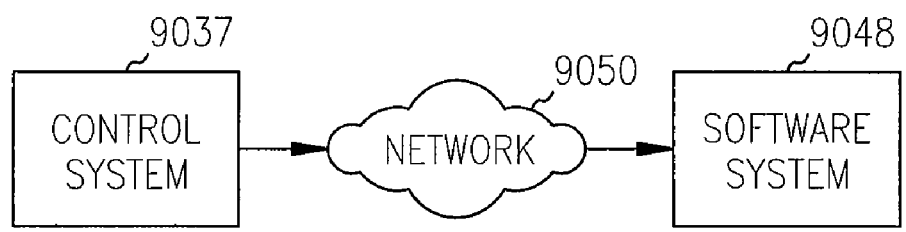

According to still another embodiment shown in FIG. 36, a control system 9037 for the dispensing machine 9038 is networked with a pharmacy management software system 9048 over a network 9050, which may include in part a local area network and a wide area network such as the Internet or a virtual private network, or satellite link, for example but not by way of limitation.

Figure 37:
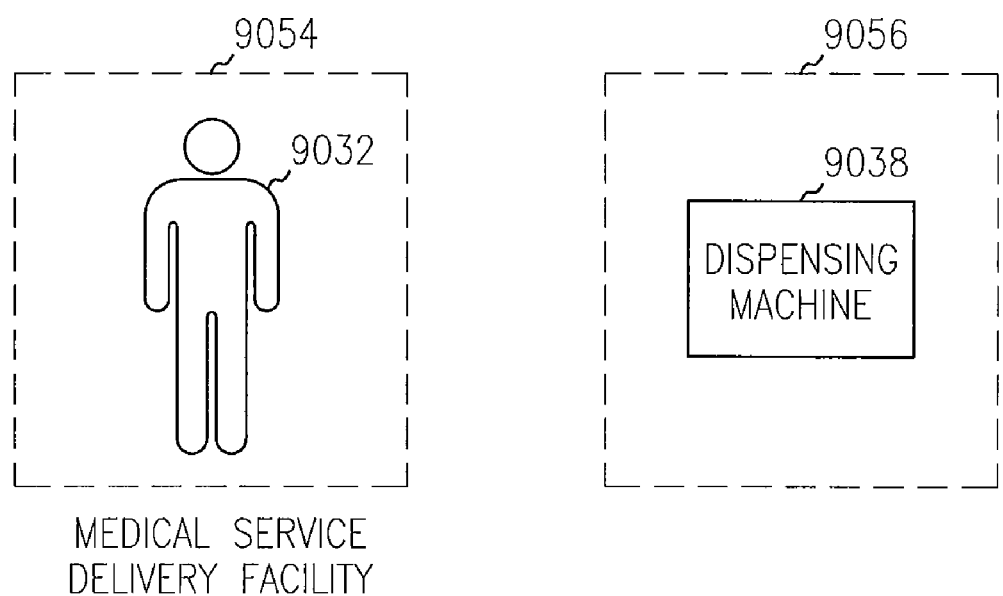

In yet another alternate embodiment as shown in FIG. 37, the medical service provider 9032 is located in a medical service delivery facility 9054, and the dispensing machine 9038 is in a pharmacy location 9056 that is not co-located with the medical service delivery facility 9054. According to this embodiment the medical service facility is, for example, but not limited to one of a doctor's office, medical HCF or hospital.

Figure 38:
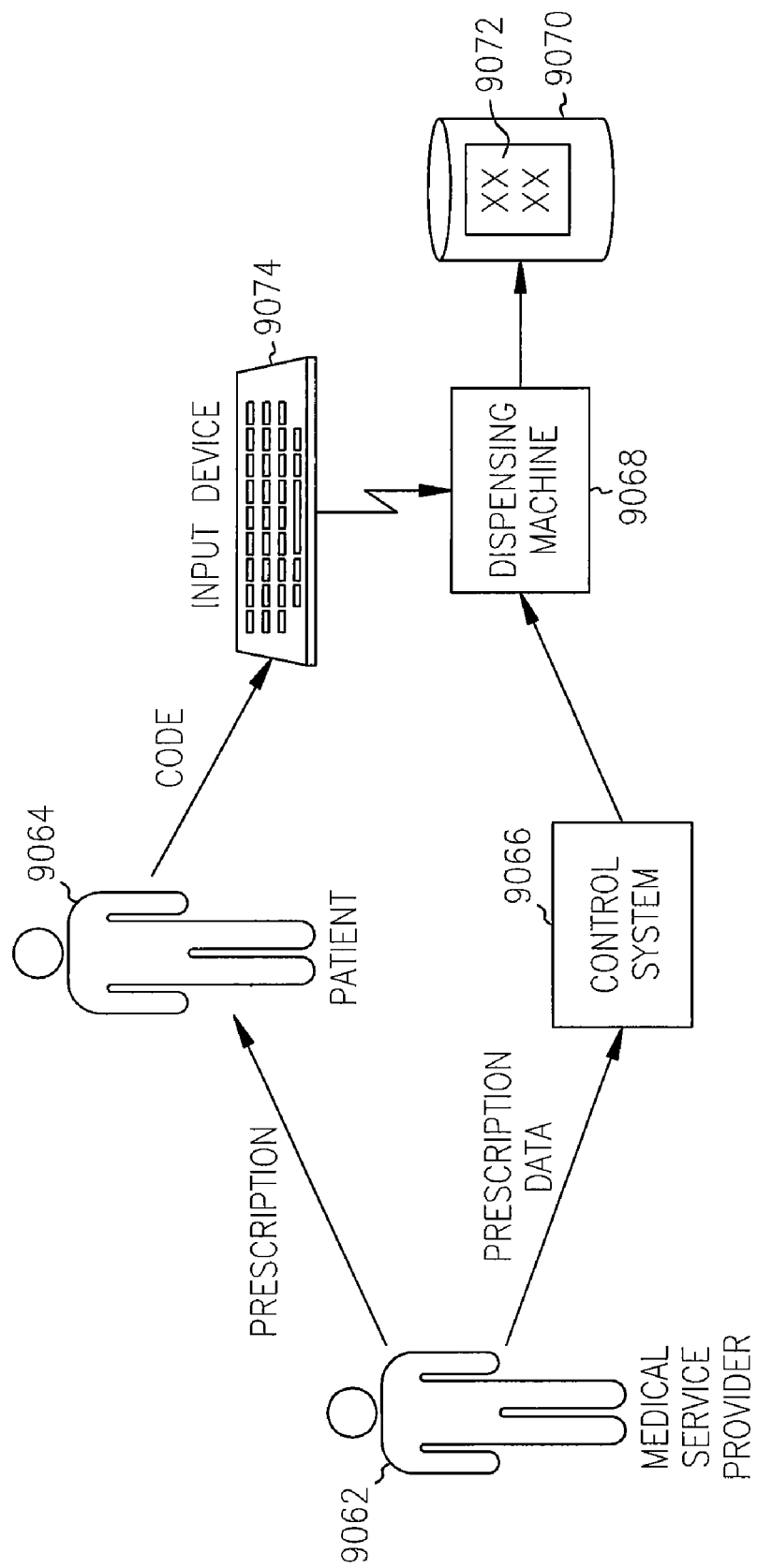

Still another example embodiment of a method according to the invention is illustrated FIG. 38. In this embodiment a medical service provider 9062 prescribes a medication for a patient 9064, and data about the prescription is entered into a control system 9066 for a medication dispensing machine 9068. The dispensing machine 9068 automatically prepares the medication by preparing a medication container 9070 holding the prescription medication wherein the container is automatically labelled 9072 with patient-specific information by the dispensing machine. Further according to this embodiment, the dispensing machine 9068 located remotely from the location of the prescribing medical service provider.

According to another example embodiment of this method, the medication is automatically labelled by the dispensing machine 9068 at the time that the patient picks up the medication. In particular, it is labelled after the patient arrives at the location of the dispensing machine. According to another example embodiment, the medication is automatically labelled by the dispensing machine 9068 prior to the time the patient arrives at the location of the dispensing machine to pick up the medication. According to another embodiment, the patient is provided with a code (for example an alphanumeric code 4-10 digits long, or a bar-code, or a written prescription, or a voucher) and the patient enters the code into an input device 9074 on the dispensing machine to obtain the labelled container.

Figure 39:
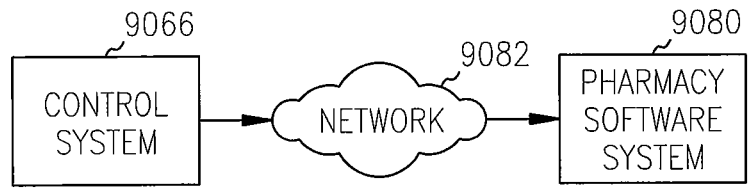

According to still another embodiment shown in FIG. 39, a control system 9066 for the dispensing machine 9068 is networked with a pharmacy management software system 9080 over a network 9082, which may include in part a local area network and a wide area network such as the Internet or a virtual private network, or a satellite link, for example but not by way of limitation.

Figure 40:
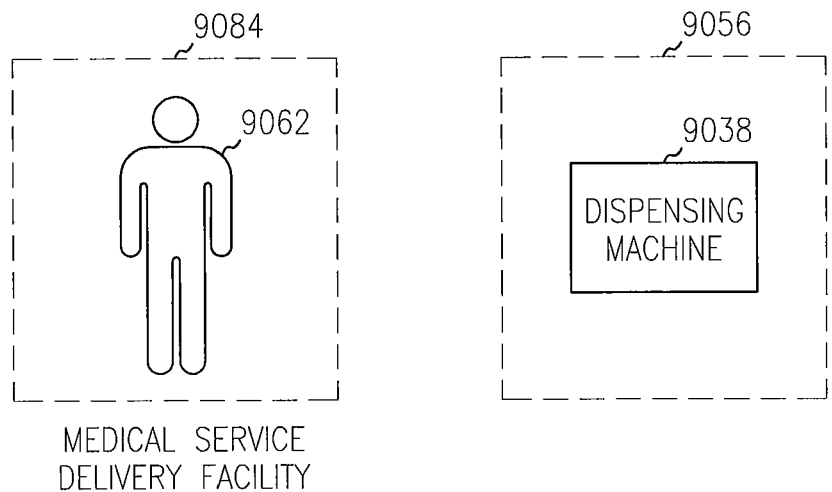

According to another example embodiment as illustrated in FIG. 40, the medical service provider 9062 is located in a medical service delivery facility 9084, and the dispensing machine 9068 is in a pharmacy, or other remote location 9086 that is not co-located with the medical service delivery facility 9084. The medical service facility may be, for instance but not by way of limitation, a doctor's office, medical HCF or hospital.

Figure 41:
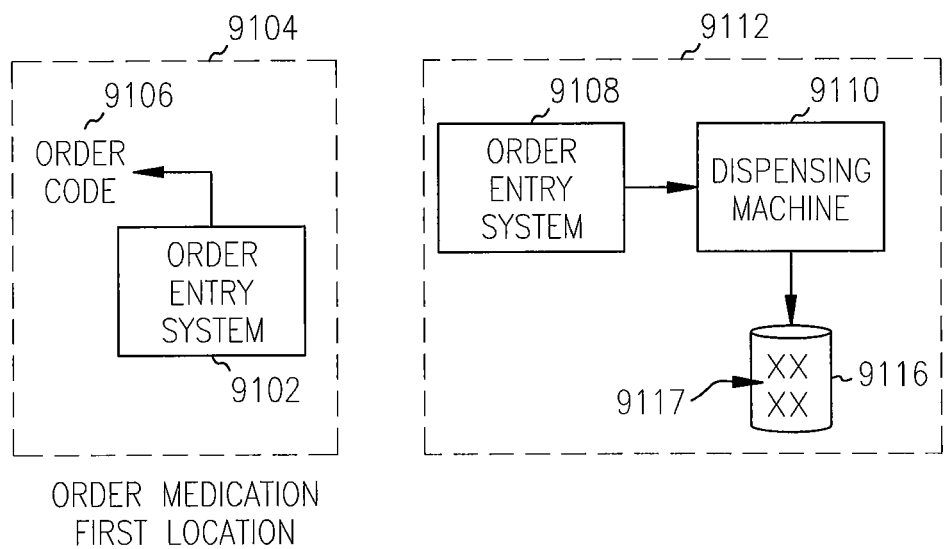

Yet still another embodiment of a method according to the present invention is illustrated in FIG. 41. In this embodiment, a medication is ordered using an automated order entry system 9102 from a first location 9104. An order code 9106 is obtained, for example by the patient or the patient's representative (which may be a family member or other care-giver). The order code 9106 is subsequently entered into a keyboard, keypad or other data entry mechanism 9108 (voice recognition for instance) in an automatic dispensing machine 9110 in a location 9112 geographically remote from the first location 9104. The dispensing machine 9110 automatically labels a container 9116 of the medication and presents it for pick-up, for example, with patient-specific information 9117. Dispensing machine 9110 may be, in one example embodiment, of the kind described above in FIGS. 1-30.

Figure 42:
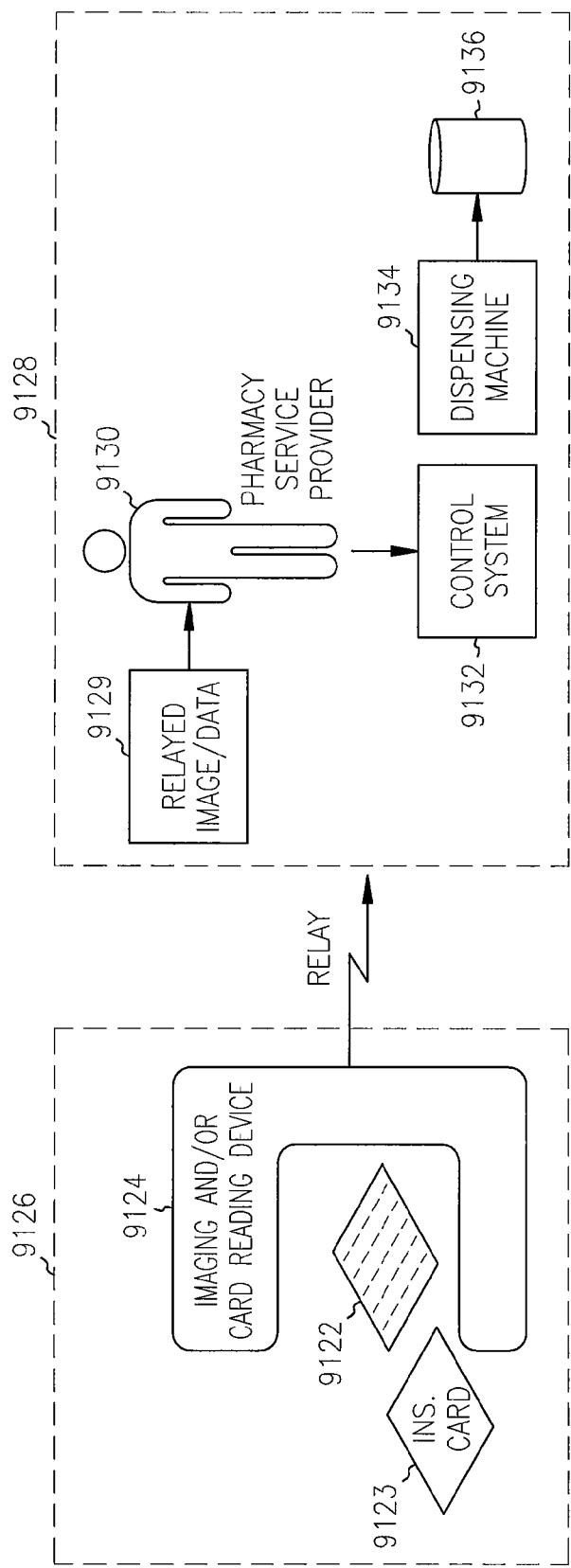

Still another example embodiment of a method according to the present invention is illustrated in FIG. 42. A written prescription, for example written or printed on a paper slip 9122, is imaged by an imaging and/or card reader device 9124 at a location 9126 and relayed (for example over a computer network or phone system) to a location 9128 remote from the location 9126 where the image is obtained. A pharmacy service provider 9130 at the remote location 9128 reads the relayed prescription image or data 9129 and enters the order into a control system 9132 for a dispensing machine 9134. The dispensing machine labels a container 9136 of the medication and presents it for pick-up.

In one embodiment, a regular prescription written on a prescription pad (or prepared using the system discussed above) can be prepared using the present system. For example, the imager can be located on the dispenser. The user puts the written prescription into the dispenser where it is imaged and the image is transferred to a pharmacy service provider located virtually anywhere. The pharmacy service provider may require the user to provide some ID. The pharmacy service provider then enters the relevant information, which is then transferred to the dispenser. The patient can enter any payment (if necessary) and the product is labeled and delivered, as discussed above. The dispenser then keeps the written prescription.

According to yet another example embodiment, the reading or imaging device 9124 is used in addition for reading or imaging an insurance card 9123 and the data from the card in an image or other electronic form is forwarded to a remote pharmacy service provider. According to yet another example embodiment, the insurance card reader may be the same or a different device from the device used to obtain an image or data from a prescription. According to yet another embodiment, a magnetic strip or other type of card reader is used to read an insurance card. Furthermore, in another embodiment, a user presents a credit card to be read by device 9024, and the credit card data is relayed both to the pharmacy service provider and to a credit card clearinghouse for approval of a payment for a medication to be dispensed by machine 9134.

Figure 43:
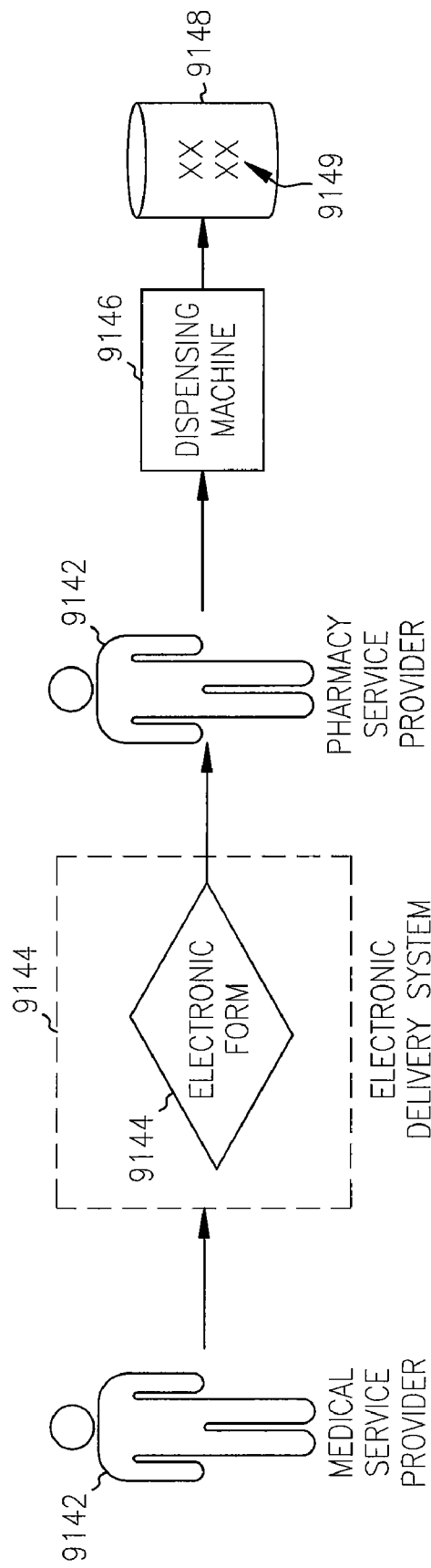

Another example embodiment of the method according to the invention is illustrated in FIG. 43. In this embodiment, a prescription is obtained in electronic form 9144 from a medical service provider 9142. The electronic prescription is presented to a pharmacy service provider 9142 using an electronic delivery system 9144. A dispensing machine 9146 prepares a container 9148 of the medication and presents it for pick-up, wherein the container is automatically labeled by the machine 9146 with patient-specific information 9149.

Figure 44:
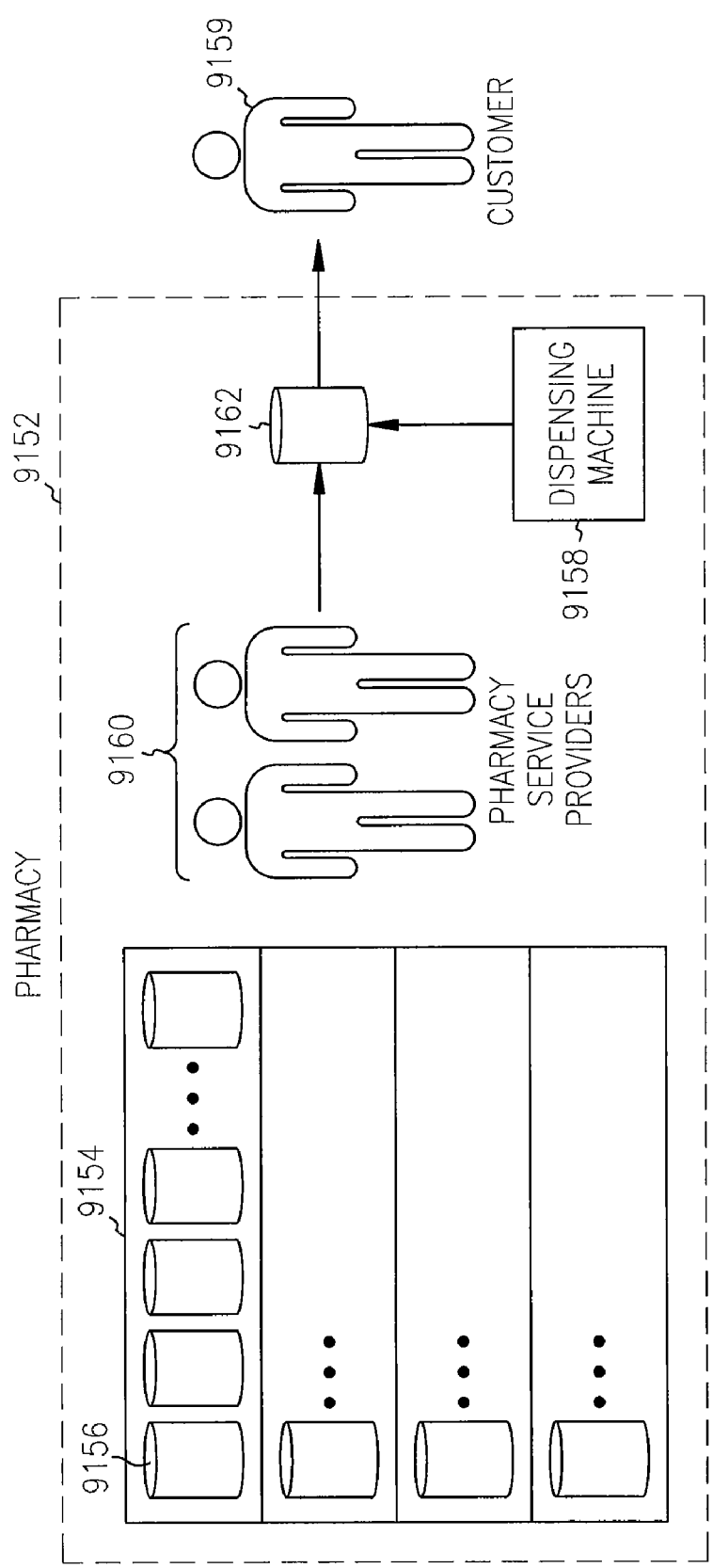

Another example embodiment of the method of the invention is illustrated in FIG. 44. A pharmacy 9152 is stocked 9154 with a variety of medications in containers 9156. An automatic dispensing machine 9158 is located at the pharmacy 9152. The pharmacy is staffed with pharmacy service providers 9160 during some but not all hours of a day. At least some prescriptions are filled for pharmacy customers at least in part by hand during the hours the pharmacy is open. At least some prescriptions are filled for pharmacy customers using the dispensing machine 9158 during hours in which there are no pharmacy staff available to dispense by hand. According to one alternate embodiment of the method, the pharmacy service providers 9160 retrieve labelled medication containers 9162 from the dispenser for customers during the service providers are working in the pharmacy, and after the pharmacy staff are no longer working, the customers 9159 themselves retrieve prescribed medication containers with the prescribed medications from the machine 9158. According to this embodiment, machine 9158 in one example embodiment takes the form of a machine as described above in FIGS. 1-30.

Figure 45:
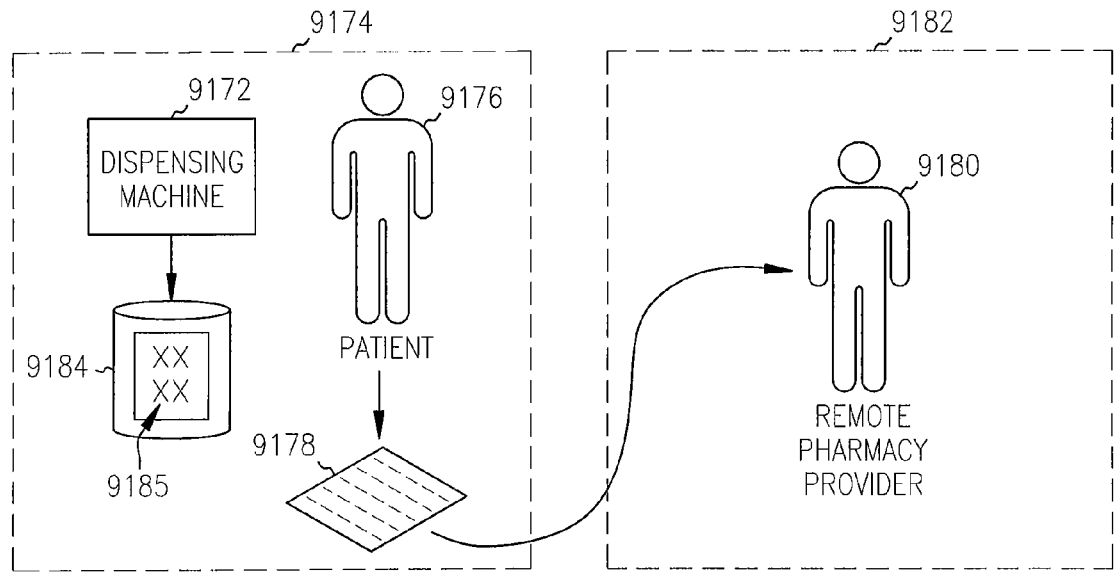

Still yet another example embodiment of a method according to the invention is illustrated in FIG. 45. In this embodiment, a dispensing machine 9172 is located at a dispensing location 9174. A patient 9176 presents a written prescription 9178 for a prescription medication at the dispensing location 9174. Information from or about the prescription is relayed to a pharmacist 9180 located remotely 9182 from the dispensing location 9174 where the pharmacist does not have immediate physical access to the dispensing location 9174. The pharmacist reads the prescription, checks the user's ID if necessary, and remotely operates the dispensing machine 9172 to cause it to automatically label a container 9184 of the medication with information 9185 specific to the patient. The patient 9176 obtains possession of the labeled medication at the dispensing location 9174. In one embodiment, the patient takes the medication from the machine.

According to yet another example embodiment of this system and method, a reading and/or imaging device is used for reading or imaging a patient insurance card or credit card and the data from the card in an image or other electronic form is forwarded to a remote pharmacy service provider. According to yet another example embodiment, the insurance card reader may be the same or a different device from the device used to obtain an image or data from a prescription.

Figure 46:
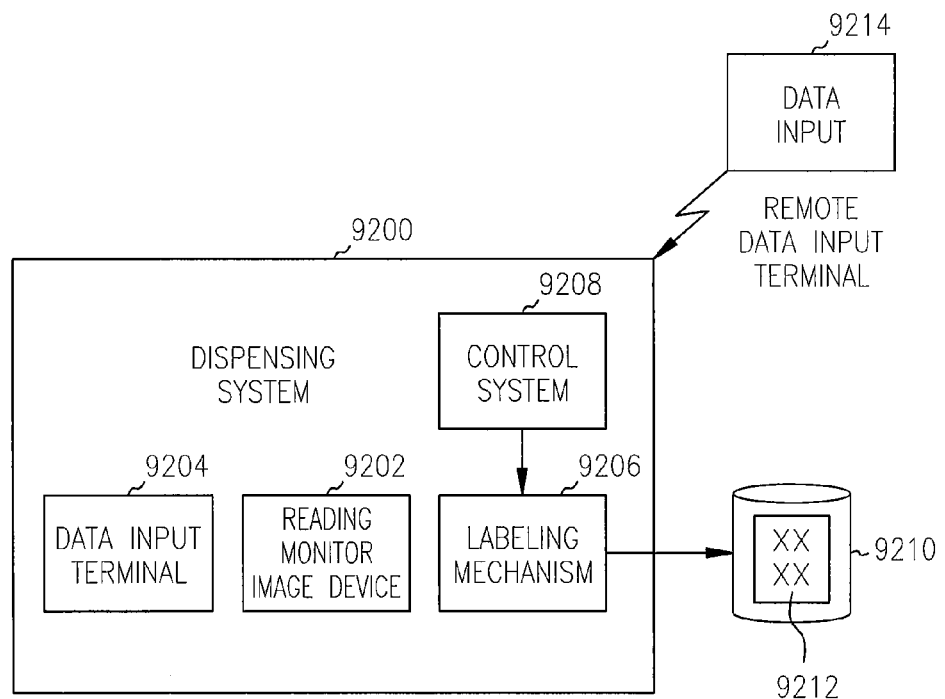

Referring now to FIG. 46, there is illustrated an alternate example embodiment of a medication dispensing system according to the present invention. The medication dispensing system 9200 includes a card reader and/or imaging device 9202 adapted to image or read a prescription presented by a patient or the patient's representative. A data input terminal 9204 receives information concerning the patient for whom the prescription is written. A medication labeling mechanism 9206 is responsive to a control system 9208 and produces labelled medication containers 9210 labeled with information 9212 specific to the patient. The control system 9208 receives instructions from an input terminal 9214 located remotely from the dispensing system. According to one example embodiment, mechanism 9206 is constructed in accordance with illustrated example mechanisms set forth hereinabove, with respect to FIGS. 1-30.

Figure 47:
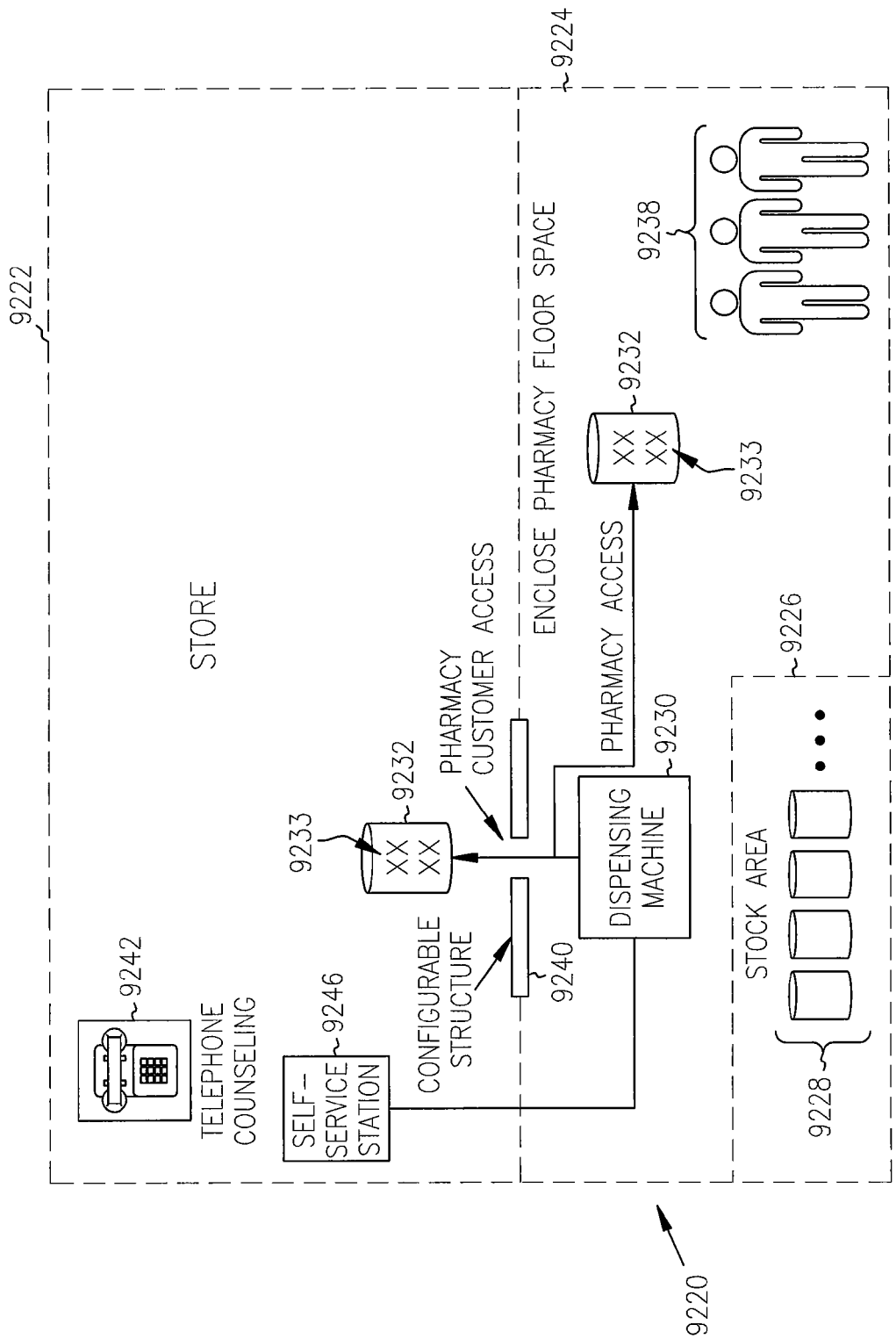

According to still another example embodiment of the invention illustrated in FIG. 47, there is provided a pharmacy configuration 9220. Configuration 9220 includes a store 9222 having an enclosed pharmacy floor space 9224 that is secured against unauthorized entry. The pharmacy floor space 9224 further includes a storage or stock area 9226 for a medication stock 9228, wherein the medication stock includes a variety of medications. An automatic medication dispensing machine 9230, for example, designed in accordance with any other above-described dispensing machine embodiment, is co-located with the pharmacy floor space and is accessible to pharmacy customers at least a portion of the operating hours of the store. The machine 9230 is adapted to dispense labelled containers 9232 of medications, wherein the label includes patient-specific information 9233. One or more pharmacy service providers 9238 work in the enclosed floor space 9224 during some but not all hours of a day.

According to an example embodiment of this configuration, the machine 9230 is positioned next to a configurable wall, gate, window or other structure 9240 that is an adapted so that pharmacy service providers can retrieve labelled medications from the dispenser for customers during the period of time the pharmacy is staffed, and so that when the pharmacy is not staffed the customers can retrieve prescribed medications directly from the machine 9230 without assistance from on-site pharmacy personnel.

According to still another example embodiment of this configuration, a remote counseling area 9242 with a telephone or other means of electronic communication such as e-mail or a chat room or a video link, is provided so that pharmacy customers may receive after hours counseling from a pharmacist in a remote location using the telephone or other means. According to still another embodiment, a system self-service station 9246 having a keyboard or keypad, for example, a printing device and an imaging and/or reading device is positioned outside the pharmacy floor space to allow a customer to submit a prescription or insurance card to a remote pharmacist as for example described with respect to FIG. 45, and also to enter a medication access code that may be printed for the customer and which causes the dispensing machine to dispense an appropriate medication for the patient.

According to still yet another example embodiment of the methods, systems and configurations illustrated in FIGS. 30-47, the dispensing machine is one of the designs described above with respect to FIGS. 1-47, and furthermore is adapted to hold approximately up to 1000 different medication options allowing a wide range of medication prescriptions to be filled using the machine. According still further to this example, any stock in any pharmacy floor space may have a greater variety of medication options, so that a wider variety of medication prescriptions can be filled from the floor stock than from the dispensing machine.

According to yet another example embodiment, the dispensing machine implemented for the systems, methods and configurations of FIGS. 30-47 include a mechanism for obtaining payment from a customer, as described above, for example by credit card, "blue tooth" payment technology, smart card cash card, cash bill changer, check reader, or any other mechanism to obtain payment from a patient. Alternatively, payment for medications may be received by pharmacy personnel or by other store personnel. Furthermore, the patient may use a card scanner or digital camera for I.D. (such as a driver's license).

Figure 48:
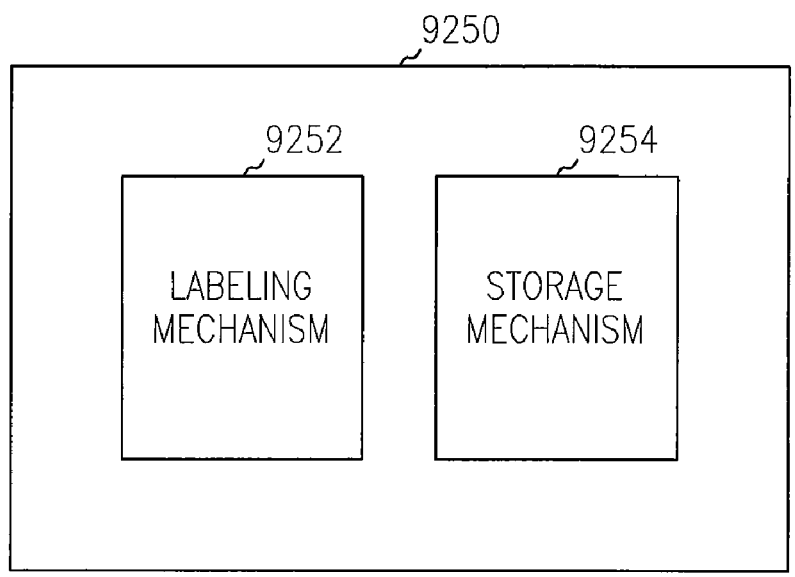
FIG. 48 illustrates an alternate embodiment of a dispensing machine according to the present invention.

Yet still another example embodiment of a dispenser of the invention is shown in schematic form in FIG. 48. This embodiment is useful, for example but not by way of limitation, with some or all of the systems, methods and configurations described with respect to FIGS. 30-47. Dispenser 9250 includes both a mechanism 9252 for labelling medications per the description provided with respect to FIGS. 1-30, but further includes an internal mechanical storage mechanism 9254, for example, a plurality of bins each holding one or more labeled medication container and having a dispensing mechanism, allowing labeled medication containers to be stored temporarily until such time as a patient or patient's representative enters an access code to retrieve the medication. According to this embodiment, prescriptions may be filled prior to the patient coming to the dispensing machine, so that the labelling is done in advance and therefore the pick up of the medication from the machine takes less time as the only mechanical function involves picking or selecting the pre-labelled medication for dispensing to the patient. Such storage mechanism, in one example embodiment, is a plurality of bins that the pre-labelled medications can be deposited in after they are labelled, with a picker or other dispensing mechanism such as a solenoid controlled container ejector device or screw mechanism for retrieving or dispensing the pre-labeled medications from the bins under computer control. The bar codes of the pre-labelled medications would again be checked prior to dispensing for quality assurance purposes.

Figure 49:
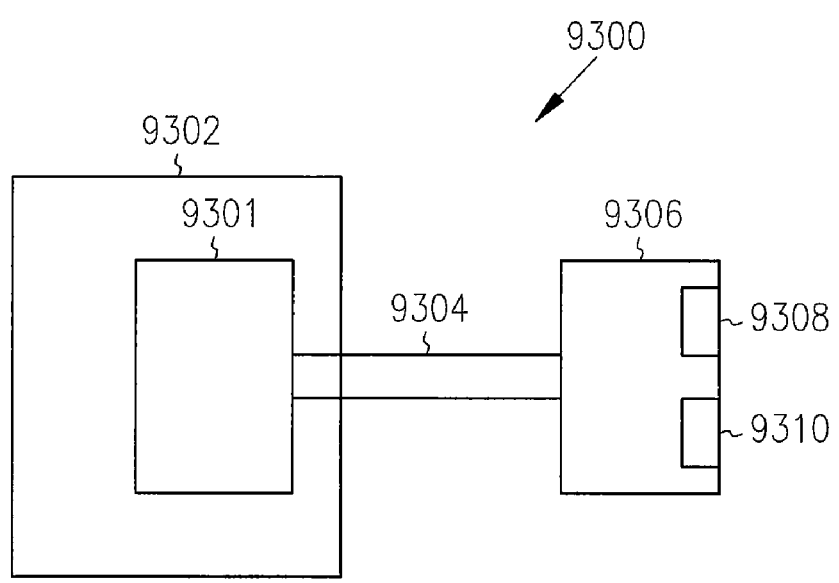
FIG. 49 illustrates a dispensing system according to one embodiment.

FIG. 49 illustrates a dispensing system 9300 according to one embodiment. System 9300 includes a dispensing machine 9301, for example any of the dispensing machines discussed herein. System 9300 also includes a feed mechanism 9304, such as a pneumatic tube device, as commonly known. In this embodiment, machine 9301 is in a first location 9302, which is inaccessible during some hours, for example a pharmacy, clinic, bank, etc. At a second location 9306, a user interface 9308 and a delivery point 9310 are provided. User interface 9308 can include an input device such as a touch-screen or keyboard. It can also include a telephone, two-way video, and other options discussed above for various user interfaces for dispensing machines. It can also include features for allowing payment, such as cash deposit, credit card readers, check readers, or an ATM interface, for example.

Feed mechanism 9304 connects dispensing machine 9301 to delivery point 9310 where the user can obtain possession of the product disposed from machine 9301.

In one example use, a user will enter their user information (such as voucher number or other authorization code) and financial information (if necessary) at user interface 9308. The dispenser will act as described above, preparing and labeling the product, then a robotic arm or other means will deliver the product to feed mechanism 9304 where it will be delivered to the user at delivery point 9310. In other example uses, a person can be inside location 9302 to facilitate the transaction. Other examples provide a remote pharmacist to facilitate the transaction from the remote location. For example, the pharmacist can talk to the patient via a telephone or two-way video and the pharmacist can control the machine 9301 and/or the feed mechanism 9304 remotely. In another example, a pharmacist located in location 9302 can receive a prescription from a patient via feed mechanism 9304, fill the prescription, and deliver the product to the patient via the feed mechanism.

One or more of the ideas discussed above are usable on virtually any dispensing machine. For example, the check reader can be utilized on a gas pump, or any vending or dispensing machine that is connected to a check authorization system.

CONCLUSION

The embodiments described above are intended only to illustrate and teach one or more ways of practicing or implementing the present invention, not to restrict its breadth or scope. The actual scope of the invention, which embraces all ways of practicing or implementing the teachings of the invention, is defined only by the following claims and their equivalents.

I claim:

1. A system comprising:
    a dispensing machine having a plurality of locations for holding a plurality of different medications;
    a scanner located within the dispensing machine and configured to scan each of the plurality of locations; and
    a control module to receive a signal from the scanner indicating the location of each of the different medications;
    wherein after the dispensing machine has been closed, the scanner automatically scans each of the locations within the dispensing machine to verify and update the location of each of the different medications in the dispenser.

2. The system of claim 1, wherein the system rescans each location after the medication has been loaded and performs an update of the position of each medication.

3. The system of claim 1, wherein the medications are stored in the dispensing machine in pre-filled magazines.

4. The system of claim 3, wherein each of the magazines includes a bar code located on an outboard end of the magazine.

5. The system of claim 4, wherein the bar code is used to identify the contents of the specific magazine.

6. The system of claim 1, wherein the control module is configured to receive the signal indicating the location of each of the medications and store the location in a memory.

7. A method comprising:
    stocking a plurality of different medications in a plurality of different locations within a dispensing machine;
    closing the dispensing machine; and
    after closing the dispensing door, the dispensing machine automatically scanning each of the plurality of different locations to verify and update the location of each of the different medications in the dispensing machine.

8. The method of claim 7, wherein stocking a plurality of different medications includes stocking a plurality of pre-filled magazines in a plurality of different locations within the dispensing machine.

9. The method of claim 8, wherein each of the pre-filled magazines includes a bar code located on an outboard end of the magazine, the bar code identifying the contents of the magazine.

10. The method of claim 7, further comprising sending a signal to a control module regarding the location of each of the medications within the dispensing machine.

11. A method comprising:
    opening a medication dispensing machine;
    removing empty magazines from the dispensing machine;
    placing filled magazines containing medications in a refill locations;
    closing the dispensing machine; and
    after closing the dispensing machine, automatically scanning each magazine to confirm placement and location.

12. The method of claim 11, wherein automatically scanning includes scanning barcodes located at the front of the magazine.

13. The method of claim 11, further comprising sending to a central server the scanned information so that inventory control is maintained.

\* \* \* \* \*